US009714232B2

(12) United States Patent
Zhang et al.

(10) Patent No.: US 9,714,232 B2
(45) Date of Patent: Jul. 25, 2017

(54) SUBSTITUTED PIPERAZINE COMPOUNDS AND METHODS OF USE THEREOF

(71) Applicant: Sunshine Lake Pharma Co., Ltd., Dongguan, Guangdong (CN)

(72) Inventors: Yingjun Zhang, Dongguan (CN); Chuanfei Jin, Dongguan (CN); Rongqi Zhou, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/026,250

(22) PCT Filed: Dec. 19, 2014

(86) PCT No.: PCT/CN2014/094430
§ 371 (c)(1),
(2) Date: Mar. 31, 2016

(87) PCT Pub. No.: WO2015/090235
PCT Pub. Date: Jun. 25, 2015

(65) Prior Publication Data

US 2016/0244429 A1 Aug. 25, 2016

(30) Foreign Application Priority Data

Dec. 20, 2013 (CN) .......................... 2013 1 0714973

(51) Int. Cl.

| | |
|---|---|
| *C07D 401/06* | (2006.01) |
| *C07D 401/10* | (2006.01) |
| *C07D 401/12* | (2006.01) |
| *C07D 471/04* | (2006.01) |
| *C07D 413/10* | (2006.01) |
| *C07D 403/12* | (2006.01) |
| *C07D 413/12* | (2006.01) |
| *C07D 491/048* | (2006.01) |
| *A61K 45/06* | (2006.01) |
| *A61K 31/496* | (2006.01) |
| *A61K 31/497* | (2006.01) |
| *A61K 31/513* | (2006.01) |
| *A61K 31/5377* | (2006.01) |

(52) U.S. Cl.
CPC .......... *C07D 401/12* (2013.01); *A61K 31/496* (2013.01); *A61K 31/497* (2013.01); *A61K 31/513* (2013.01); *A61K 31/5377* (2013.01); *A61K 45/06* (2013.01); *C07D 401/06* (2013.01); *C07D 403/12* (2013.01); *C07D 413/10* (2013.01); *C07D 413/12* (2013.01); *C07D 471/04* (2013.01); *C07D 491/048* (2013.01)

(58) Field of Classification Search
CPC .. C07D 401/06; C07D 413/10; C07D 413/12; C07D 471/04
See application file for complete search history.

(56) References Cited

U.S. PATENT DOCUMENTS

| | | | |
|---|---|---|---|
| 3,188,313 | A | 6/1965 | Archer |
| 3,562,278 | A | 2/1971 | Archer |
| 5,002,948 | A | 3/1991 | Perregaard et al. |
| 5,106,850 | A | 4/1992 | Butcher et al. |
| 5,418,237 | A | 5/1995 | Bottcher et al. |
| 5,532,241 | A | 7/1996 | Bottcher et al. |
| 5,681,954 | A | 10/1997 | Yamamoto et al. |
| 5,725,838 | A | 3/1998 | Pollak et al. |
| 6,262,056 | B1 | 7/2001 | Monge Vega et al. |
| 6,310,068 | B1 | 10/2001 | Bottcher et al. |
| 7,332,495 | B2 | 2/2008 | Li et al. |
| 7,576,086 | B2 | 8/2009 | Li et al. |
| 8,680,097 | B2 | 3/2014 | Li et al. |
| 2003/0083336 | A1 | 5/2003 | Ruhland et al. |
| 2006/0122191 | A1 | 6/2006 | Heinrich et al. |
| 2006/0148815 | A1 | 7/2006 | Bang-Andersen et al. |
| 2009/0238761 | A1 | 9/2009 | Campiani et al. |
| 2011/0059982 | A1 | 3/2011 | Heinrich et al. |
| 2013/0064770 | A1 | 3/2013 | Newington et al. |

FOREIGN PATENT DOCUMENTS

| | | | |
|---|---|---|---|
| CA | 972372 | A | 8/1975 |
| CN | 1101039 | A | 4/1995 |
| CN | 1844120 | A | 10/2006 |
| CN | 104725363 | A | 6/2015 |
| WO | 9414769 | A1 | 7/1994 |
| WO | 03076400 | A1 | 9/2003 |

OTHER PUBLICATIONS

Same Genes Suspected in Both Depression and Bipolar Illness. Science, Jan. 2010, po. 1-4.*
Pessoa-Mahana et al., Synthesis, 5-hydroxytryptamine1A receptor affinity and docking studies of 3-[3-(4-aryl-1-piperazinyl)-propyl]-1H-indole derivatives, Chemical and Pharmaceutical Bulletin, 2012, 60(5): 632-638.
Heinrich et al., Indolebutylamines as Selective 5-HT1A Agonists, Journal of Medicinal Chemistry, 2004, 47(19): 4677-4683.
International Search Report of PCT/CN2014/094430.
Written Opinion of PCT/CN2014/094430.

* cited by examiner

*Primary Examiner* — Samira Jean-Louis
(74) *Attorney, Agent, or Firm* — Kam W. Law; Squire Patton Boggs (US) LLP

(57) ABSTRACT

Provided herein are novel piperazine compounds and pharmaceutical compositions thereof comprising the piperazine compounds for inhibiting serotonin reuptake and/or acting as 5-HT1A receptor agonists. Also provided herein are methods for preparing the novel piperazine compounds and pharmaceutical compositions thereof, and uses of them in treating central nervous system (CNS) dysfunction.

21 Claims, No Drawings

SUBSTITUTED PIPERAZINE COMPOUNDS AND METHODS OF USE THEREOF

CROSS-REFERENCE TO RELATED APPLICATIONS

This is a U.S. national stage application of the International Patent Application No. PCT/CN2014/094430, filed 19 Dec. 2014, which claims priority to Chinese Patent Application No. 201310714973.7, filed 20 Dec. 2013, both of which are incorporated herein by reference in their entireties.

FIELD

The present invention belongs to the field of pharmaceutical technology, and more specifically relates to novel substituted piperazine compounds, compositions and methods of use thereof for treating central nervous system dysfunction. Particularly, provided herein are piperazine compounds acting as 5-serotonin reuptake inhibitors and/or $5\text{-HT}_{1A}$ receptor agonists.

BACKGROUND

Serotonin, a neurotransmitter that carries signal in the brain and nerves, plays a very important role in central nervous system (CNS) dysfunction, especially in anxiety, depression, aggression and impulsivity. Regulation of the central nervous system dysfunction is possible either by antagonistic or agonistic action on a certain type of the serotonin receptors. To date, at least 14 different serotonin receptors have been identified. These receptors can be divided into distinct families—denoted $5\text{-HT}_1$, $5\text{-HT}_2$, $5\text{-HT}_3$, $5\text{-HT}_4$, $5\text{-HT}_5$, $5\text{-HT}_6$ and $5\text{-HT}_7$, with subtypes in each family denoted by letters such as a, b and c. Central serotonergic neurons are located in the raphe nuclei in the brain stem. The $5\text{-HT}_{1A}$ receptor is a G-protein-coupled receptor widely distributed in regions that receive serotonergic input from the raphe nuclei: the frontal cortex, septum, amygdala, hippocampus, and hypothalamus. In these cortico-limbic regions, $5\text{-HT}_{1A}$ is distributed post-synaptically. The $5\text{-HT}_{1A}$ receptor also serves as the predominant (somatodendritic) autoreceptor of the raphe nuclei, reducing the firing rate of neurons (the amount of serotonin released per action potential), the synthesis of the neurotransmitter, and thus by implication, the serotonergic activity of its projection areas. Activation of the presynaptic $5\text{-HT}_{1A}$ receptor may also indirectly reduce serotonergic transmission through the inhibition of tyrosine hydroxylase synthesis, as well as the activity of glutamatergic pathway that originates in the medial prefrontal cortex and projects to the raphe nuclei (Jonathan Savitz et al., "$5\text{-HT}_{1A}$ receptor function in major depressive disorder," *Prog. Neurobiol.*, 2009, 88(1): 17-31).

Depression is the most important of all therapeutic indications related to 5-HT disorder since it is the fourth leading burdensome disease in the world according to the World Health Organization. By 2020, depression is projected to rank second in disability-adjusted life years (Bromet E et al., "Cross-national epidemiology of DSM-IV major depressive episode," *BMC Med.*, 2011, 9: 90).

Historically, tricyclic antidepressants (TCAs) and monoamine oxidase inhibitors (MAOIs) revolutionized the pharmacologic treatment of mood disorders in the 1950s, mostly by blocking neurotransmitter (dopamine, norepinephrine, and serotonin). However, the non-selectivity and undesirable side effect eventually limited their use. In 1980s, the discovery of selective serotonin reuptake inhibitors (SSRIs) changed the landscape. As a class, the SSRIs boast similar efficacy compared to the TCAs, and an improved AE profile with less tendency for toxicity in overdose (Sarko J, "Andidepressant, old and new. A review of their adverse effects and toxicity in overdose," *Emerg. Med. Clin North Am.*, 2000, 18 (4): 637-54).

Conventional SSRIs therapeutically increase available serotonin by inhibiting its reuptake and modulating its transmission. Administration of SSRIs also pleiotropically stimulates pre-synaptic $5\text{-HT}_{1A}$ autoreceptors, which acutely decreases the release of serotonin and subsequently reduces serotonin concentrations in the synapse. After chronic administration, the stimulation of the $5\text{-HT}_{1A}$ autoreceptors is overcome via desensitization and the SSRIs is able to normalize serotonergic transmission. It is postulated that this stimulation of the autoreceptor is the causative factor in the delayed therapeutic effect of the SSRIs (Celada P et al., "The therapeutic role of $5\text{-HT}_{1A}$ and $5\text{-HT}_{2A}$ receptors in depression," *J Psychiatry Neurosci.*, 2004, 29(4): 252-65). Thus, overriding the negative feedback effect of $5\text{-HT}_{1A}$ autoreceptors antagonists holds the promise of increasing and accelerating clinical antidepressant effects.

Compared to SSRIs, $5\text{-HT}_{1A}$ receptor agonists or partial agonists act directly on postsynaptic serotonin receptors to increase serotonin neurotransmission during the SSRI latency effect period. Feiger and Wilcox demonstrated that the buspirone and gepirone were clinically effective $5\text{-HT}_{1A}$ partial agonists (Feiger, A, *Psychopharmacol. Bull.*, 1996, 32: 659-65). The addition of buspirone to standard SSRI treatment produced a marked improvement in patients previously unresponsive to standard treatment for depression (Dimitriou, E. J., *Clin. Psychopharmacol.*, 1998, 18: 465-9).

Provided herein are novel compounds believed to have clinical use in treating CNS disorders through selectively inhibiting serotonin reuptake and/or acting as $5\text{-HT}_{1A}$ receptor agonists. The compounds disclosed herein are also believed to provide an improvement in potency, pharmacokinetic properties, and/or toxicity profile over certain counterparts found in the art.

SUMMARY

This section merely summarizes certain aspects disclosed herein and is not intended to be limiting in nature. These aspects and other aspects are described more fully below. All the documents cited in the present specification are hereby incorporated herein by reference in their entireties. Where the disclosure of the present specification is inconsistent with a patent, application, or publication incorporated by reference, the disclosure of the present specification shall prevail.

Provided herein are novel compounds acting as selective serotonin reuptake inhibitors and/or the $5\text{-HT}_{1A}$ receptor agonists. The compounds can be used to manufacture medicaments for the treatment of central nervous system (CNS) dysfunction, such as depression, anxiety disorder and bipolar disorder.

Provided herein also are methods for preparing the novel compounds disclosed herein and pharmaceutical compositions containing the compounds.

In one aspect, provided herein are compounds having Formula (I) or a stereoisomer, a tautomer, an N-oxide, a solvate, a metabolite, a pharmaceutically acceptable salt or a prodrug thereof, (I)

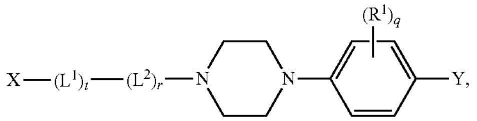

wherein

X is

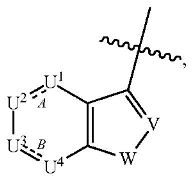

wherein each of $\overset{A}{=}$ and $\overset{B}{=}$ is independently a single bond or a double bond;

each of $U^1$, $U^2$, $U^3$ and $U^4$ is independently $CR^2$, N, —$CR^2R^{2a}$— or —$NR^{2b}$—;

or $U^1$ and $U^2$ together or $U^3$ and $U^4$ together independently form —$CR^2R^{2a}$—, —$NR^{2b}$—, —O— or —S—;

V is $CR^2$ or N;

W is $NR^{2b}$, —O— or —S—;

each $L^1$ is —$CR^3R^4$—;

each $L^2$ is —$CR^5R^6$—;

t is 0, 1 or 2;

r is 1, 2, 3, 4 or 5;

q is 1, 2, 3 or 4;

Y is

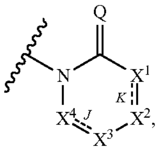

wherein Q is O, S or $N(R^7)$;

each of $\overset{J}{=}$ and $\overset{K}{=}$ is independently a single bond or a double bond;

each of $X^1$, $X^2$, $X^3$ and $X^4$ is independently —O—, —S—, $CR^8$, N, —$CR^8R^{8a}$— or —$NR^{8b}$—;

or $X^1$ and $X^2$ together or $X^3$ and $X^4$ together independently form —$CR^8R^{8a}$—, —$NR^{8b}$—, —O— or —S—;

each $R^1$ is independently H, D, F, Cl, Br, I, —CN, —$N_3$, —$NO_2$, —$NR^aR^b$, —$OR^c$, alkyl, alkenyl or alkynyl, wherein each of alkyl, alkenyl and alkynyl is optionally and independently substituted with one or more $R^9$;

each $R^2$, $R^{2a}$ and $R^{2b}$ is independently H, D, F, Cl, Br, I, —CN, —$N_3$, —$NO_2$, —$NR^aR^b$, —$S(=O)_mR^c$, —$C(=O)R^c$, —$C(=O)OR^c$, —$C(=O)NR^aR^b$, —$S(=O)_2NR^aR^b$, —$OC(=O)R^c$, —$N(R^a)C(=O)R^c$, alkyl, alkenyl or alkynyl, wherein each of alkyl, alkenyl and alkynyl is optionally and independently substituted with one or more $R^9$;

each $R^3$ and $R^4$ is independently H, D, F, Cl, Br, I, —CN, —$N_3$, —$NH_2$, —OH, alkyl, alkenyl, alkynyl, alkoxy, alkylamino, cycloalkyl, heterocyclyl, aryl or heteroaryl, or $R^3$ and $R^4$, together with the carbon atom to which they are attached, form a carbonyl group, a carbocyclic ring or a heterocyclic ring, wherein each of alkyl, alkenyl, alkynyl, alkoxy, alkylamino, cycloalkyl, heterocyclyl, aryl, heteroaryl, the carbocyclic ring and the heterocyclic ring is optionally and independently substituted with one or more $R^9$;

each $R^5$ and $R^6$ is independently H, D, F, Cl, Br, I, —CN, —$N_3$, —$NH_2$, —OH, alkyl, alkenyl, alkynyl, alkoxy, alkylamino, cycloalkyl, heterocyclyl, aryl or heteroaryl, or $R^5$ and $R^6$, together with the carbon atom to which they are attached, form a carbocyclic ring or a heterocyclic ring, wherein each of alkyl, alkenyl, alkynyl, alkoxy, alkylamino, cycloalkyl, heterocyclyl, aryl, heteroaryl, the carbocyclic ring and the heterocyclic ring is optionally and independently substituted with one or more $R^9$;

$R^7$ is H, —OH, —$NH_2$, $C_1$-$C_4$ alkyl, $C_1$-$C_4$ haloalkyl or $C_1$-$C_4$ alkylamino;

each $R^8$, $R^{8a}$ and $R^{8b}$ is independently H, D, F, Cl, Br, I, —CN, —$N_3$, —$NO_2$, —($C_0$-$C_6$ alkylene)-$NR^aR^b$, —($C_0$-$C_6$ alkylene)-$OR^c$, —($C_0$-$C_6$ alkylene)-$S(=O)_mR^c$, —$C(=O)R^c$, —$C(=O)OR^c$, —$C(=O)NR^aR^b$, —$S(=O)_2NR^aR^b$, —$OC(=O)R^c$, —$N(R^a)C(=O)R^c$, alkyl, alkenyl, alkynyl, cycloalkyl, heterocyclyl, aryl or heteroaryl;

or two $R^8$ on two adjacent ring atoms, or two $R^{8b}$ on two adjacent ring atoms, or $R^8$ and $R^{8b}$ on two adjacent ring atoms, together with the ring atoms to which they are attached, independently form a carbocyclic ring, a heterocyclic ring, an aryl ring or a heteroaryl ring, wherein each of the carbocyclic ring, the heterocyclic ring, the aryl ring and the heteroaryl ring is optionally and independently substituted with one or more substituents independently selected from $R^x$ and $R^y$;

each $R^9$ is independently F, Cl, Br, I, —CN, —$N_3$, —$NO_2$, —OH, —SH, —$NH_2$, alkyl, haloalkyl, alkoxy, alkylthio or alkylamino;

each $R^x$ and $R^y$ is independently H, D, F, Cl, Br, I, —CN, —$N_3$, —$NO_2$, —$NR^aR^b$, —$OR^c$, —$SR^c$, —$C(=O)NR^aR^b$, —$C(=O)OR^c$, —O—($C_0$-$C_6$ alkylene)-$C(=O)NR^aR^b$, —O—($C_0$-$C_6$ alkylene)-$C(=O)OR^c$, alkyl or haloalkyl;

each $R^a$ and $R^b$ is independently H, alkyl, alkenyl, alkynyl, haloalkyl, —($C_0$-$C_6$ alkylene)-cycloalkyl, —($C_0$-$C_6$ alkylene)-heterocyclyl, —($C_0$-$C_6$ alkylene)-aryl or —($C_0$-$C_6$ alkylene)-heteroaryl, or $R^a$ and $R^b$, together with the nitrogen atom to which they are attached, form a heterocyclic ring;

each $R^c$ is independently H, alkyl, alkenyl, alkynyl, haloalkyl, —($C_0$-$C_6$ alkylene)-cycloalkyl, —($C_0$-$C_6$ alkylene)-heterocyclyl, —($C_0$-$C_6$ alkylene)-aryl or —($C_0$-$C_6$ alkylene)-heteroaryl; and each m is independently 0, 1 or 2.

In one embodiment, each $R^1$ is independently H, D, F, Cl, Br, I, —CN, —$N_3$, —$NO_2$, —$NR^aR^b$, $C_1$-$C_6$ alkyl, $C_2$-$C_6$ alkenyl or $C_2$-$C_6$ alkynyl, wherein each of $C_1$-$C_6$ alkyl, $C_2$-$C_6$ alkenyl and $C_2$-$C_6$ alkynyl is optionally and independently substituted with one or more $R^9$.

In another embodiment, X is

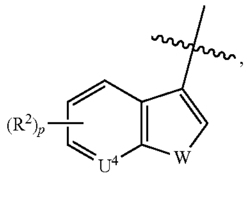

wherein $U^4$ is $CR^2$ or N;

p is 1, 2 or 3; and

W is —NH—, —O— or —S—.

In another embodiment, each $R^2$, $R^{2a}$ and $R^{2b}$ is independently H, D, F, Cl, Br, I, —CN, —$N_3$, —$NO_2$, —$NR^aR^b$, —$OR^c$, —$S(=O)_mR^c$, —$C(=O)R^c$, —$C(=O)OR^c$, —$C(=O)NR^aR^b$, —$S(=O)_2NR^aR^b$, —$OC(=O)R^c$, —$N(R^a)C(=O)R^c$, $C_1$-$C_6$ alkyl, $C_2$-$C_6$ alkenyl or $C_2$-$C_6$ alkynyl, wherein each of $C_1$-$C_6$ alkyl, $C_2$-$C_6$ alkenyl and $C_2$-$C_6$ alkynyl is optionally and independently substituted with one or more $R^9$.

In another embodiment, each $R^3$ and $R^4$ is independently H, D, F, Cl, Br, I, —CN, —$N_3$, —$NH_2$, —OH, $C_1$-$C_6$ alkyl, $C_2$-$C_6$ alkenyl, $C_2$-$C_6$ alkynyl, $C_1$-$C_6$ alkoxy, $C_1$-$C_6$ alkylamino, $C_3$-$C_{10}$ cycloalkyl, 3-10 membered heterocyclyl, $C_6$-$C_{10}$ aryl or 5-10 membered heteroaryl, or $R^3$ and $R^4$, together with the carbon atom to which they are attached, form a carbonyl group, a $C_3$-$C_8$ carbocyclic ring or a 3-7 membered heterocyclic ring, wherein each of $C_1$-$C_6$ alkyl, $C_2$-$C_6$ alkenyl, $C_2$-$C_6$ alkynyl, $C_1$-$C_6$ alkoxy, $C_1$-$C_6$ alkylamino, $C_3$-$C_{10}$ cycloalkyl, 3-10 membered heterocyclyl, $C_6$-$C_{10}$ aryl, 5-10 membered heteroaryl, the $C_3$-$C_8$ carbocyclic ring and the 3-7 membered heterocyclic ring is optionally and independently substituted with one or more $R^9$.

In another embodiment, each $R^5$ and $R^6$ is independently H, D, F, Cl, Br, I, —CN, —$N_3$, —$NH_2$, —OH, $C_1$-$C_6$ alkyl, $C_2$-$C_6$ alkenyl, $C_2$-$C_6$ alkynyl, $C_1$-$C_6$ alkoxy, $C_1$-$C_6$ alkylamino, $C_3$-$C_{10}$ cycloalkyl, 3-10 membered heterocyclyl, $C_6$-$C_{10}$ aryl or 5-10 membered heteroaryl, or $R^5$ and $R^6$, together with the carbon atom to which they are attached, form a $C_3$-$C_8$ carbocyclic ring or a 3-7 membered heterocyclic ring, wherein each of $C_1$-$C_6$ alkyl, $C_2$-$C_6$ alkenyl, $C_2$-$C_6$ alkynyl, $C_1$-$C_6$ alkoxy, $C_1$-$C_6$ alkylamino, $C_3$-$C_{10}$ cycloalkyl, 3-10 membered heterocyclyl, $C_6$-$C_{10}$ aryl, 5-10 membered heteroaryl, $C_3$-$C_8$ carbocyclic ring and 3-7 membered heterocyclic ring is optionally and independently substituted with one or more $R^9$.

In another embodiment, each $R^8$, $R^{8a}$ and $R^{8b}$ is independently H, D, F, Cl, Br, I, —CN, —$N_3$, —$NO_2$, —($C_0$-$C_6$ alkylene)_$NR^aR^b$, —($C_0$-$C_6$ alkylene)-$OR^c$, —($C_0$-$C_6$ alkylene)-$S(=O)_mR^c$, —$C(=O)R^c$, —$C(=O)OR^c$, —$C(=O)NR^aR^b$, —$S(=O)_2NR^aR^b$, —$OC(=O)R^c$, —$N(R^a)C(=O)R^c$, $C_1$-$C_6$ alkyl, $C_2$-$C_6$ alkenyl, $C_2$-$C_6$ alkynyl, $C_3$-$C_{10}$ cycloalkyl, 3-10 membered heterocyclyl, $C_6$-$C_{10}$ aryl or 5-10 membered heteroaryl; and or two $R^8$ on two adjacent ring atoms, or two $R^{8b}$ on two adjacent ring atoms, or $R^8$ and $R^{8b}$ on two adjacent ring atoms, together with the ring atoms to which they are attached, independently form a $C_3$-$C_{10}$ carbocyclic ring, a 3-10 membered heterocyclic ring, a $C_6$-$C_{10}$ aryl ring or a 5-10 membered heteroaryl ring, wherein each of the $C_3$-$C_{10}$ carbocyclic ring, the 3-10 membered heterocyclic ring, the $C_6$-$C_{10}$ aryl ring and the 5-10 membered heteroaryl ring is optionally and independently substituted with one or more substituents independently selected from $R^x$ and $R^y$.

In another embodiment, each $R^9$ is independently F, Cl, Br, I, —CN, —$N_3$, —$NO_2$, —OH, —SH, —$NH_2$, $C_1$-$C_6$ alkyl, $C_1$-$C_6$ haloalkyl, $C_1$-$C_6$ alkoxy, $C_1$-$C_6$ alkylthio or $C_1$-$C_6$ alkylamino.

In another embodiment, each $R^x$ and $R^y$ is independently H, D, F, Cl, Br, I, —CN, —$N_3$, —$NO_2$, —$NR^aR^b$, —$OR^c$, —$SR^c$, —$C(=O)NR^aR^b$, —$C(=O)OR^c$, —O—($C_0$-$C_6$ alkylnene)-$C(=O)NR^aR^b$, —O—($C_0$-$C_6$ alkylene)-$C(=O)OR^c$, $C_1$-$C_6$ alkyl or $C_1$-$C_6$ haloalkyl.

In another embodiment, the compounds disclosed herein have Formula (II) or a stereoisomer, a tautomer, an N-oxide, a solvate, a metabolite, a pharmaceutically acceptable salt or a prodrug thereof, (II)

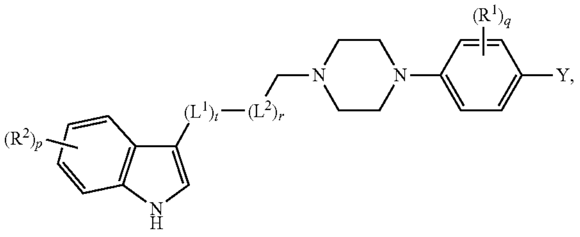

wherein p is 1, 2 or 3; and r is 1, 2, 3 or 4.

In another embodiment, each $R^1$ is independently H, D, F, Cl, Br, —CN, —$NO_2$, —$OR^c$ or $C_1$-$C_4$ alkyl, wherein the $C_1$-$C_4$ alkyl is optionally substituted with one or more $R^9$.

In another embodiment, each $R^1$ is independently H, D, F, Cl, Br, —CN, —$NO_2$, -Me, —$CF_3$ or —OMe.

In another embodiment, each $R^2$, $R^{2a}$ and $R^{2b}$ is independently H, D, F, Cl, Br, —CN, —$NO_2$, —$NR^aR^b$, —$C(=O)OR^c$, —$C(=O)NR^aR^b$ or $C_1$-$C_4$ alkyl, wherein the $C_1$-$C_4$ alkyl is optionally substituted with one or more $R^9$.

In another embodiment, each $R^2$, $R^{2a}$ and $R^{2b}$ is independently H, D, F, Cl, Br, —CN, —$NO_2$, —$NH_2$, —$NMe_2$, —OH, —OMe, —O(i-Pr), -Me, -Et, -(i-Pr), —$CF_3$, —C(=O)OH, —C(=O)OMe or —$CONH_2$.

In another embodiment, each $L^1$ is —$CH_2$—, —C(=O)— or —CH(OH)—.

In another embodiment, each $L^2$ is —$CH_2$—.

In another embodiment, Y is

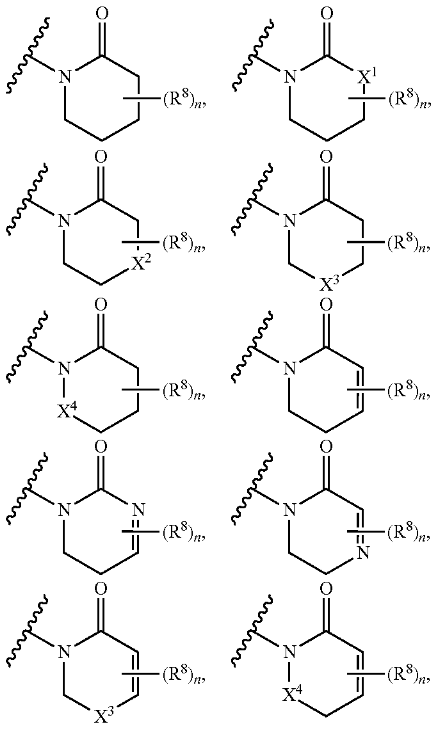

-continued

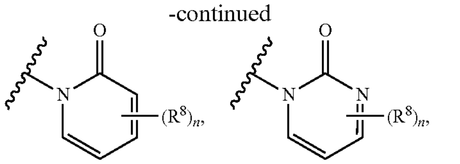

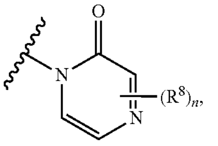

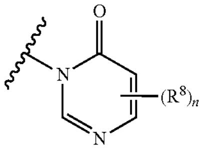

or

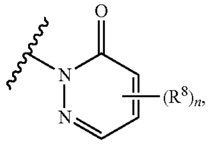

wherein each $X^1$, $X^2$, $X^3$ and $X^4$ is independently —O—, —S— or —$NR^{8b}$—; and each n is independently 1, 2, 3 or 4.

In another embodiment, Y is

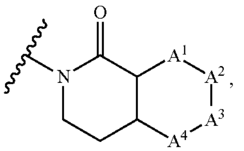

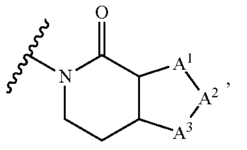

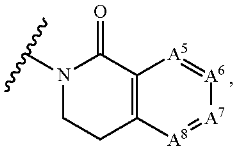

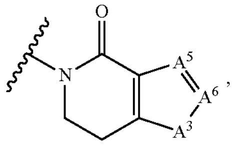

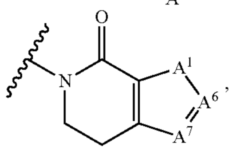

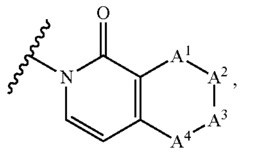

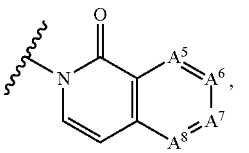

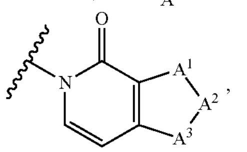

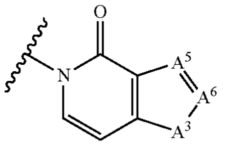

or

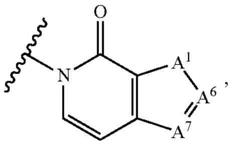

wherein each $A^1$, $A^2$, $A^3$ and $A^4$ is independently —O—, —S—, —$NR^y$— or —$CHR^x$—; and each $A^5$, $A^6$, $A^7$ and $A^8$ is independently N or $CR^x$.

In another embodiment, each $R^8$, $R^{8a}$ and $R^{8b}$ is independently H, D, F, Cl, Br, —CN, —$NO_2$, —($C_0$-$C_4$ alkylene)-$OR^c$, —($C_0$-$C_4$ alkylene)-$NR^aR^b$, —C(═O)$OR^c$, —C(═O)$NR^aR^b$, $C_1$-$C_4$ alkyl, $C_2$-$C_4$ alkenyl or $C_2$-$C_4$ alkynyl; and or two $R^8$ on two adjacent ring atoms, or two $R^{8b}$ on two adjacent ring atoms, or $R^8$ and $R^{8b}$ on two adjacent ring atoms, together with the ring atoms to which they are attached, independently form a $C_3$-$C_8$ carbocyclic ring, a 3-7 membered heterocyclic ring, a benzene ring or a 5-6 membered heteroaryl ring, wherein each of the $C_3$-$C_8$ carbocyclic ring, the 3-7 membered heterocyclic ring, the benzene ring and the 5-6 membered heteroaryl ring is optionally and independently substituted with one or more substituents independently selected from $R^x$ and R.

In another embodiment, each $R^8$, $R^{8a}$ and $R^{8b}$ is independently H, D, F, Cl, Br, —CN, —$NO_2$, —OH, —$NH_2$, —C(═O)OMe, —C(═O)OEt, —C(═O)$NH_2$, -Me, -Et, -(i-Pr), —OMe, —O(i-Pr) or —$NMe_2$.

In another embodiment, each $R^x$ and $R^y$ is independently H, D, F, Cl, Br, —CN, —$NO_2$, —$NR^aR^b$, —SW, —C(═O)$NR^aR^b$, —C(═O)$OR^c$, —O—($C_0$-$C_4$ alkylnene)-C(═O)$NR^aR^b$, —O—($C_0$-$C_4$ alkylene)-C(═O)$OR^c$, $C_1$-$C_4$ alkyl or $C_1$-$C_4$ haloalkyl.

In another embodiment, each $R^x$ and $R^y$ is independently H, D, F, Cl, Br, —CN, —$NO_2$, —OH, —OMe, —$NH_2$, —$NMe_2$, —COOH, —C(═O)OMe, —C(═O)OEt, —C(═O)$NH_2$, —$OCH_2COOH$, —$OCH_2C$(═O)OMe, —$OCH_2C$(═O)OEt, —$OCH_2C$(═O)$NH_2$, -Me, -Et, -(i-Pr) or —$CF_3$.

In another embodiment, each $R^a$ and $R^b$ is independently H, $C_1$-$C_4$ alkyl, $C_2$-$C_4$ alkenyl, $C_2$-$C_4$ alkynyl, $C_1$-$C_4$ haloalkyl, —($C_0$-$C_4$ alkylene)-($C_3$-$C_8$ cycloalkyl), —($C_0$-$C_4$ alkylene)-(3-7 membered heterocyclyl), —($C_0$-$C_4$ alkylene)-(phenyl) or —($C_0$-$C_4$ alkylene)-(5-6 membered heteroaryl), or $R^a$ and $R^b$, together with the nitrogen atom to which they are attached, form a 3-7 membered heterocyclic ring; and each $R^c$ is independently H, $C_1$-$C_4$ alkyl, $C_2$-$C_4$ alkenyl, $C_2$-$C_4$ alkynyl, $C_1$-$C_4$ haloalkyl, —($C_0$-$C_4$ alkylene)-($C_3$-$C_8$ cycloalkyl), —($C_0$-$C_4$ alkylene)-(3-7 membered heterocyclyl), —($C_0$-$C_4$ alkylene)-(phenyl) or —($C_0$-$C_4$ alkylene)-(5-6 membered heteroaryl).

In another aspect, provided herein is a pharmaceutical composition containing the compound disclosed herein.

In one embodiment, the pharmaceutical composition disclosed herein further comprises a pharmaceutically acceptable excipient, carrier, adjuvant or a combination thereof.

In another embodiment, the pharmaceutical composition disclosed herein further comprises an additional therapeutic agent for central nervous system dysfunction, wherein the additional therapeutic agent for central nervous system dysfunction is an antidepressant, an antianxiety agent, a lithium agent of mood stabilizer, an atypical antipsychotic agent, an antiepileptic agent, an anti-Parkinson agent, a selective serotonin reuptake inhibitor, a 5-$HT_{1A}$ receptor agonist, a central nervous system stimulant, a nicotine antagonist or a combination thereof.

In another embodiment, the additional therapeutic agent is amitriptyline, desipramine, mirtazapine, bupropion, reboxetine, fluoxetine, trazodone, sertraline, duloxetine, fluvoxamine, milnacipran, levomilnacipran, desvenlafaxine, vilazodone, venlafaxine, dapoxetine, nefazodone, femoxetine, clomipramine, citalopram, escitalopram, paroxetine, lithium carbonate, buspirone, olanzapine, quetiapine, risperidone, ziprasidone, aripiprazole, perospirone, clozapine, modafinil, mecamylamine, cabergoline, adamantane, imipramine, pramipexole, thyroxine, dextromethorphan, quinidine, naltrexone, samidorphan, buprenorphine, melatonin, alprazolam, pipamperone, vestipitant, chlordiazepoxide, perphenazine or a combination thereof.

In another aspect, provided herein is use of the compound or the pharmaceutical composition disclosed herein in the manufacture of a medicament for preventing, treating or lessening the severity of a central nervous system dysfunction in a subject. In one embodiment, the subject is a mammal, and in another embodiment, the subject is a human being.

In another aspect, provided herein is a method of preventing, treating or lessening the severity of a central nervous system dysfunction in a subject comprising administrating a therapeutically effective amount of the compound or the pharmaceutical composition disclosed herein to the subject. In one embodiment, the subject is a mammal, and in another embodiment, the subject is a human being.

In another aspect, provided herein is the compound or the pharmaceutical composition disclosed herein for use in preventing, treating or lessening the severity of a central nervous system dysfunction in a subject. In one embodiment, the subject is a mammal, and in another embodiment, the subject is a human being.

In one embodiment, the central nervous system dysfunction is depression, anxiety, mania, schizophrenia, bipolar disorder, sleep disorder, obsessive compulsive disorder, panic disorder, post-traumatic stress disorder, movement disorder, sexual dysfunction, musculoskeletal pain disorder, cognitive disorder, memory disorder, Parkinson's disease, Huntington's disease, phobia, substance abuse or addiction, drug addiction withdrawal symptom or premenstrual tension syndrome.

In another aspect, provided herein is use of the compound or the pharmaceutical composition disclosed herein in the manufacture of a medicament for inhibiting serotonin reuptake.

In another aspect, provided herein is a method of inhibiting serotonin reuptake with the compound or the pharmaceutical composition disclosed herein.

In another aspect, provided herein is the compound or the pharmaceutical composition disclosed herein for use in inhibiting serotonin reuptake.

In another aspect, provided herein is use of the compound or the pharmaceutical composition disclosed herein in the manufacture of a medicament for partially activating 5-$HT_{1A}$ receptor.

In another aspect, provided herein is a method of partially activating 5-$HT_{1A}$ receptor with the compound or the pharmaceutical composition disclosed herein.

In another aspect, provided herein is the compound or the pharmaceutical composition disclosed herein for use in partially activating 5-$HT_{1A}$ receptor.

In another aspect, provided herein are methods for preparation, separation and purification of the compounds represented by Formula (I) or (II).

Biological test results indicate that the compounds provided herein can be used as preferred selective serotonin reuptake inhibitors and/or 5-$HT_{1A}$ receptor agonists.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects and embodiments are described more fully below.

DETAILED DESCRIPTION

Definitions and General Terminology

Reference will now be made in detail to certain embodiments of the invention, examples of which are illustrated in the accompanying structures and formulas. The invention is intended to cover all alternatives, modifications and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

Unless defined otherwise, all technical and scientific terms used herein have the same meaning as is commonly understood by one skilled in the art to which this invention belongs. All patents and publications referred to herein are incorporated by reference in their entireties.

As used herein, the following definitions shall apply unless otherwise indicated. For purposes of this invention, the chemical elements are identified in accordance with the Periodic Table of the Elements, CAS version, and *the Handbook of Chemistry and Physics,* $75^{th}$ Ed. 1994. Additionally, general principles of organic chemistry are described in "*Organic Chemistry*", Thomas Sorrell, University Science Books, Sausalito: 1999, and "*March's Advanced Organic Chemistry*" by Michael B. Smith and Jerry March, John Wiley & Sons, New York: 2007, all of which are incorporated herein by reference in their entireties.

The grammatical articles "one", "a", "an" and "the", as used herein, are intended to include "at least one" or "one or more" unless otherwise indicated herein or clearly contradicted by the context. Thus, the articles are used herein to refer to one or more than one (i.e., to at least one) of the grammatical objects of the article. By way of example, "a component" means one or more components, and thus, possibly, more than one component is contemplated and may be employed or used in an implementation of the described embodiments.

The term "optional" or "optionally" refers to that a subsequently described event or circumstance may but need not occur, and that the description includes instances where the event or circumstance occurs and instances in which it does not. For example, "optional bond" means that the bond may or may not be present, and that the description includes single, double or triple bonds.

As described herein, compounds disclosed herein may optionally be substituted with one or more substituents, such as those illustrated above, or as exemplified by particular classes, subclasses and species of the invention.

The term "substituted" refers to the replacement of one or more hydrogen groups in a given structure with the group of a specified substituent. Unless otherwise indicated, a substituted group may have a substituent at each substitutable position of the group. When more than one position in a given structure may be substituted with more than one substituent selected from a specified group, the substituent may be either the same or different at each position.

The term "unsubstituted" refers to a specified group without substituents.

The term "optionally substituted with . . . " is used interchangeably with the term "unsubstituted or substituted with . . . ", i.e., the given structure is unsubstituted or substituted with one or more substituents described herein. Some non-limiting examples of the substituents include D, F, Cl, $—N_3$, —CN, —OH, —SH, $—NH_2$, alkyl, alkoxy, alkylthio, alkylamino, cycloalkyl, heterocyclyl, aryl, heteroaryl, and the like.

Furthermore, what need to be explained is that the phrase "each . . . is independently" and "each of . . . and . . . is independently", unless otherwise stated, should be broadly understood, i.e., the specific options expressed by the same symbol are independent of each other in different groups; or the specific options expressed by the same symbol are independent of each other in same groups.

The term "comprising" is an open-ended expression, which includes the content specified in the invention, but does not exclude other aspects.

The term "unsaturated" refers to a moiety having one or more units of unsaturation.

At various places in the present specification, substituents of the compounds disclosed herein are disclosed in groups or in ranges. It is specifically intended that the invention includes each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "halogen" or "halo", which may be used interchangeably herein, refers to F, Cl, Br or I.

The term "alkyl" or "alkyl group" refers to a saturated linear or branched-chain monovalent hydrocarbon group of 1-20 carbon atoms, wherein the alkyl group is optionally substituted with one or more substituents described herein. Unless otherwise specified, the alkyl group contains 1-20 carbon atoms. In one embodiment, the alkyl group contains 1-12 carbon atoms. In another embodiment, the alkyl group contains 1-6 carbon atoms. In still another embodiment, the alkyl group contains 1-4 carbon atoms. In yet another embodiment, the alkyl group contains 1-3 carbon atoms. The alkyl group is optionally substituted with one or more substituents described herein.

Some non-limiting examples of the alkyl group include methyl (Me, $—CH_3$), ethyl (Et, $—CH_2CH_3$), n-propyl (n-Pr, $—CH_2CH_2CH_3$), isopropyl (i-Pr, $—CH(CH_3)_2$), n-butyl (n-Bu, $—CH_2CH_2CH_2CH_3$), isobutyl (i-Bu, $—CH_2CH(CH_3)_2$), sec-butyl (s-Bu, $—CH(CH_3)CH_2CH_3$), tert-butyl (t-Bu, $—C(CH_3)_3$), n-pentyl ($—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), n-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$), n-heptyl, n-octyl, and the like.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In one embodiment, the alkylene group contains 1-6 carbon atoms. In another embodiment, the alkylene group contains 1-4 carbon atoms. In still another embodiment, the alkylene group contains 1-3 carbon atoms. In yet another embodiment, the alkylene group contains 1-2 carbon atoms. The alkylene group is exemplified by methylene ($—CH_2—$), ethylene ($—CH_2CH_2—$), isopropylene ($—CH(CH_3)CH_2—$), and the like. The alkylene group is optionally substituted with one or more substituents described herein.

The term "alkenyl" refers to a linear or branched chain monovalent hydrocarbon group of 2-12 carbon atoms with at least one site of unsaturation, i.e., a carbon-carbon, $sp^2$ double bond, wherein the alkenyl group is optionally substituted with one or more substituents described herein, and includes groups having "cis" and "trans" orientations, or alternatively, "E" and "Z" orientations. In one embodiment, the alkenyl group contains 2-8 carbon atoms. In another embodiment, the alkenyl group contains 2-6 carbon atoms. In still another embodiment, the alkenyl group contains 2-4 carbon atoms. Some non-limiting examples of the alkenyl group include ethenyl or vinyl ($—CH{=}CH_2$), allyl ($—CH_2CH{=}CH_2$), and the like. The alkenyl group is optionally substituted with one or more substituents described herein.

The term "alkynyl" refers to a linear or branched-chain monovalent hydrocarbon group of 2-12 carbon atoms with at least one site of unsaturation, i.e., a carbon-carbon, sp triple bond, wherein the alkynyl group is optionally substituted with one or more substituents described herein. In one embodiment, the alkynyl group contains 2-8 carbon atoms. In another embodiment, the alkynyl group contains 2-6 carbon atoms. In still another embodiment, the alkynyl group contains 2-4 carbon atoms. Some non-limiting examples of the alkynyl group include ethynyl ($—C{\equiv}CH$), propargyl ($—CH_2C{\equiv}CH$), 1-propynyl ($—C{\equiv}C—CH_3$), and the like. The alkynyl group is optionally substituted with one or more substituents described herein.

The term "alkoxy" refers to an alkyl group, as previously defined, attached to the parent molecular moiety through an oxygen atom, wherein the alkyl group is as defined herein. Unless otherwise specified, the alkoxy group contains 1-12 carbon atoms. In one embodiment, the alkoxy group contains 1-6 carbon atoms. In another embodiment, the alkoxy group contains 1-4 carbon atoms. In still another embodiment, the alkoxy group contains 1-3 carbon atoms. The alkoxy group is optionally substituted with one or more substituents described herein.

Some non-limiting examples of the alkoxy group include methoxy (MeO, $—OCH_3$), ethoxy (EtO, $—OCH_2CH_3$), 1-propoxy (n-PrO, n-propoxy, $—OCH_2CH_2CH_3$), 2-propoxy i-propoxy, $—OCH(CH_3)_2$), 1-butoxy (n-BuO, n-butoxy, $OCH_2CH_2CH_2CH_3$), 2-methyl-1-propoxy i-butoxy, $—OCH_2CH(CH_3)_2$), 2-butoxy (s-BuO, s-butoxy, $—OCH(CH_3)CH_2CH_3$), 2-methyl-2-propoxy (t-BuO, t-butoxy, $—OC(CH_3)_3$), 1-pentoxy (n-pentoxy, $—OCH_2CH_2CH_2CH_2CH_3$), 2-pentoxy ($—OCH(CH_3)CH_2CH_2CH_3$), 3-pentoxy ($—OCH(CH_2CH_3)_2$), 2-methyl-2-butoxy ($—OC(CH_3)_2CH_2CH_3$), 3-methyl-2-butoxy ($—OCH(CH_3)CH(CH_3)_2$), 3-methyl-1-butoxy ($—OCH_2CH_2CH(CH_3)_2$), 2-methyl-1-butoxy ($—OCH_2CH(CH_3)CH_2CH_3$), and the like.

The term "haloalkyl" or "haloalkoxy" refers to an alkyl or alkoxy group substituted with one or more halogen atoms, wherein the alkyl group and alkoxy group are as defined herein. Some non-limiting examples of the haloalkyl group and the haloalkoxy group include chloromethyl, trifluoromethyl, trifluoroethyl, trifluoromethoxy, and the like. The haloalkyl group or the haloalkoxy group is optionally substituted with one or more substituents described herein.

The term "aminoalkyl" refers to a linear or branched alkyl group of 1-10 carbon atoms substituted with one or more amino groups. In one embodiment, the aminoalkyl group is lower aminoalkyl group having 1-6 carbon atoms and one or more amino groups. Some non-limiting examples of the aminoalkyl group include aminomethyl, aminoethyl, aminopropyl, and the like. The aminoalkyl group is optionally substituted with one or more substituents described herein.

The term "alkylamino" embraces "N-alkylamino" and "N,N-dialkylamino", wherein the amino group is independently substituted with one or two alkyl groups, respectively. In one embodiment, the alkylamino group is lower alkylamino group having one or two alkyl groups of 1-6 carbon atoms, which are attached to a nitrogen atom. In another embodiment, the alkylamino group is lower alkylamino group having 1-4 carbon atoms. Some non-limiting examples of the alkylamino group include monoalkylamino or dialkylamino such as N-methylamino, N-ethylamino, N,N-dimethylamino, N,N-diethylamino, and the like. The alkylamino group is optionally substituted with one or more substituents described herein.

The term "alkylthio" refers to a group in which a linear or branched alkyl group of 1-10 carbon atoms is attached to a divalent sulfur atom. In one embodiment, the alkylthio group is lower alkylthio group having 1-4 carbon atoms. Some non-limiting examples of the alkylthio group include methylthio ($CH_3S—$). The alkylthio group is optionally substituted with one or more substituents described herein.

The term "carbocycle", "carbocyclyl" or "carbocyclic ring" refers to a monovalent or multivalent non-aromatic, saturated or partially unsaturated ring having 3 to 12 carbon atoms as a monocyclic, bicyclic or tricyclic ring system. A carbobicyclyl system includes a spiro carbobicyclyl or fused carbobicyclyl. Suitable carbocyclyl groups include, but are not limited to, cycloalkyl, cycloalkenyl and cycloalkynyl. Further non-limiting examples of the carbocyclyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. The carbocyclyl group is optionally substituted with one or more substituents described herein.

The term "cycloalkyl" refers to a monovalent or multivalent saturated ring having 3 to 12 carbon atoms as a monocyclic, bicyclic or tricyclic ring system, wherein the bicyclic or tricyclic ring system may include fused ring, bridged ring and spiro ring. In one embodiment, the cycloalkyl contains 3-10 carbon atoms. In another embodiment, the cycloalkyl contains 3-8 carbon atoms. In still another embodiment, the cycloalkyl contains 3-6 carbon atoms. The cycloalkyl group is optionally substituted with one or more substituents described herein.

The term "heteroatom" refers to one or more of oxygen (O), sulfur (S), nitrogen (N), phosphorus (P) or silicon (Si), including any oxidized form of nitrogen (N), sulfur (S) or phosphorus (P); the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "heterocycle", "heterocyclyl" or "heterocyclic ring" as used interchangeably herein refers to a monocyclic, bicyclic or tricyclic ring system containing 3-12 ring atoms of which one or more ring members are an independently selected heteroatom as defined herein and that is completely saturated or that contains one or more units of unsaturation, but which is not aromatic. In one embodiment, the "heterocycle", "heterocyclyl" or "heterocyclic ring" group is a monocycle having 3 to 8 ring members (e.g., 2 to 6 carbon atoms and 1 to 3 heteroatoms selected from N, O, P and S, wherein the S or P is optionally substituted with one or more oxo to provide the group SO or $SO_2$, or PO or $PO_2$, with the proviso that when the ring is a 3-membered ring, there is only one heteroatom) or a bicycle having 7 to 12 ring members (e.g., 4 to 9 carbon atoms and 1 to 3 heteroatoms selected from N, O, P and S, wherein the S or P is optionally substituted with one or more oxo to provide the group SO or $SO_2$, or PO or $PO_2$). The heterocyclyl group is optionally substituted with one or more substituents described herein.

The heterocyclyl group may be a carbon radical or a heteroatom radical, of which a $—CH_2—$ group can optionally be replaced by a —C(═O)— group. Ring sulfur atoms may be optionally oxidized to form S-oxides, and ring nitrogen atoms may be optionally oxidized to form N-oxides. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, 2-oxa-5-azabicyclo[2.2.1]hept-5-yl, and the like. Some non-limiting examples of the heterocyclyl group of which the $—CH_2—$ group is replaced by —C(═O)— moiety include 2-oxopyrrolidinyl, oxo-1,3-thiazolidinyl, 2-piperidonyl, 3,5-dioxopiperidinyl, pyrimidindionyl, and the like. Some non-limiting examples of the heterocyclyl group of which the ring sulfur atom is oxidized include sulfolanyl, thiomorpholinyl 1,1-dioxide, and the like. The heterocyclyl group is optionally substituted with one or more substituents described herein.

In one embodiment, the heterocyclyl group may be 3-7 membered heterocyclyl. Some non-limiting examples of the 3-7 membered heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, 2-oxa-5-azabicyclo[2.2.1]hept-5-yl, and the like. Some non-limiting examples of the heterocyclyl group of which the $—CH_2—$ group is replaced by —C(═O)— moiety include 2-oxopyrrolidinyl, oxo-1,3-thiazolidinyl, 2-piperidonyl, 3,5-dioxopiperidinyl, pyrimidindionyl, and the like. Some non-limiting examples of the heterocyclyl group of which the ring sulfur atom is oxidized include sulfolanyl, thiomorpholinyl 1,1-dioxide, and the like. The 3-7 membered heterocyclyl group is optionally substituted with one or more substituents described herein.

In another embodiment, the heterocyclyl group may be 4-6 membered heterocyclyl. Some non-limiting examples of the 4-6 membered heterocyclyl group include azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, and the like. Some non-limiting examples of the heterocyclyl group of the —$CH_2$— group is replaced by —C(═O)— moiety include 2-oxopyrrolidinyl, oxo-1,3-thiazolidinyl, 2-piperidonyl, 3,5-dioxopiperidinyl, pyrimidindionyl, and the like. Some non-limiting examples of the heterocyclyl group of which the ring sulfur atom is oxidized include sulfolanyl, thiomorpholinyl 1,1-dioxide, and the like. The 4-6 membered heterocyclyl group is optionally substituted with one or more substituents described herein.

In still another embodiment, the heterocyclyl group refers to a 7-12 membered heterocyclyl. Some non-limiting examples of the 7-12 membered heterocyclyl include 2-oxa-5-azabicyclo[2.2.1]hept-5-yl, and the like. The 7-12 membered heterocyclyl group is optionally substituted with one or more substituents described herein.

The term "heterocycloalkyl" refers to a monovalent or multivalent saturated ring having 3 to 12 ring atoms as a monocyclic, bicyclic or tricyclic ring system of which at least one ring atom is selected from nitrogen, sulfur and oxygen.

The term "aryl" refers to a monocyclic, bicyclic or tricyclic carbocyclic ring system having a total of 6 to 14 ring members, preferably, 6 to 12 ring members, and more preferably 6 to 10 ring members, wherein at least one ring in the system is aromatic, and wherein each ring in the system contains 3 to 7 ring members. The aryl group is generally, but not necessarily bonded to the parent molecule through an aromatic ring of the aryl group. The term "aryl" may be used interchangeably with the term "aryl ring". Some non-limiting examples of the aryl group include phenyl, naphthyl, anthracene, and the like. The aryl group is optionally substituted with one or more substituents described herein.

The term "arylamino" refers to an amino group substituted with one or two aryl groups. Some non-limiting examples of the arylamino group include N-phenylamino, and the like. In one embodiment, the arylamino group may be further substituted on the aryl ring portion of the group.

The term "heteroaryl" refers to a monocyclic, bicyclic or tricyclic ring system having a total of 5 to 12 ring members, preferably, 5 to 10 ring members, and more preferably 5 to 6 ring members, wherein at least one ring in the system is aromatic, and at least one ring in the system contains one or more heteroatoms, and wherein each ring in the system contains 5 to 7 ring members. The heteroaryl group is generally, but not necessarily bonded to the parent molecule through an aromatic ring of the heteroaryl group. The term "heteroaryl" may be used interchangeably with the term "heteroaryl ring" or the term "heteroaromatic ring". The heteroaryl group is optionally substituted with one or more substituents described herein. In one embodiment, a 5-10 membered heteroaryl comprises 1, 2, 3 or 4 heteroatoms independently selected from O, S and N.

Some non-limiting examples of the heteroaryl group include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the like; and the following bicycles: benzimidazolyl, benzofuryl, benzothiophenyl, indolyl (e.g., 2-indolyl), purinyl, quinolinyl (e.g., 2-quinolinyl, 3-quinolinyl and 4-quinolinyl), isoquinolinyl (e.g., 1-isoquinolinyl, 3-isoquinolinyl and 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, triazolo[1,5-a]pyridyl, and the like.

The term "x membered" where x is an integer typically describes the number of ring-forming atoms in a moiety where the number of ring-forming atoms is x. For example, piperidinyl is an example of a 6 membered heterocyclo alkyl.

The term "azido" or "$N_3$" refers to an azide moiety. This radical may be attached, for example, to a methyl group to form azidomethane (methyl azide, $MeN_3$), or attached to a phenyl group to form phenyl azide ($PhN_3$).

The term "carboxy" or "carboxyl", whether used alone or with other terms, such as "carboxyalkyl", refers to —$CO_2H$.

The term "carbonyl", whether used alone or with other terms, such as "aminocarbonyl" or "carbonyloxy", denotes —(C═O)—.

The term "fused bicyclic ring", "fused cyclic", "fused bicyclyl" or "fused cyclyl" as used interchangeably herein refers to a monovalent or multivalent saturated or partially unsaturated bridged ring system, which refers to a bicyclic ring system that is not aromatic. For example, as depicted below in Figure a, Figure b and Figure c, two five-membered rings (Figure a), two six-membered rings (Figure b), and a five-membered ring and a six-membered ring (Figure c) are a bridged ring system shared a common C—C bond. Such a ring system may contain isolated or conjugated unsaturation, but not aromatic or heteroaromatic rings in its core structure (but may have aromatic substitution thereon). Each ring in the fused bicyclic ring system is independently carbocyclic ring or heterocyclic ring.

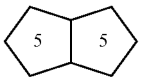

a

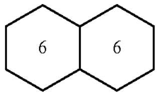

b

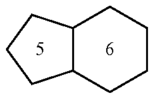

c

Some non-limiting examples of the fused bicyclyl group include hexahydrofuro[2,3-b]furan-3-yl, hexahydrofuro[3,2-b]furan-3-yl, octahydrocyclopenta[c]pyrrol-5-yl, octahydropentalen-2-yl, octahydro-1H-isoindol-5-yl, and the like. The fused bicyclyl group is optionally substituted with one or more substituents described herein.

The term "spirocyclyl", "spirocyclic", "spiro bicyclyl" or "spiro bicyclic" as used interchangeably herein refers to a monovalent or multivalent, saturated or partially unsaturated ring system wherein a ring originating from a particular annular carbon of another ring. For example, as depicted below in Figure d and Figure f, ring A and ring B share a carbon atom between the two saturated ring system, which terms as a "spirocyclyl" or "spiro bicyclyl". Each ring in the spiro bicyclyl can be either a carbocyclyl or a heterocyclyl. Some non-limiting examples of the spiro bicyclyl group include 4-oxaspiro[2.4]hept-6-yl, and (R)-4-azaspiro[2.4]hept-6-yl. The spiro bicyclyl group is optionally substituted with one or more substituents described herein.

d

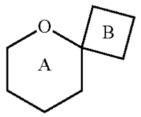

e

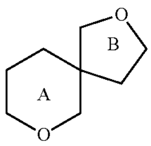

As described herein, a bond drawn from a substituent R to the center of one ring within a ring system represents substitution of the substituent R at any substitutable position on the ring. For example, Figure f represents possible substitution of the substituent R in any of the position on ring A or ring B, as shown in Formula g, Formula h, and Formula i, Formula j, Formula k, Formula l and Formula m.

f

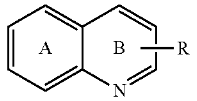

g

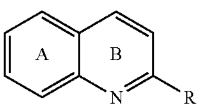

h

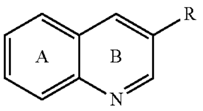

i

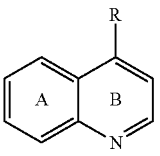

-continued j

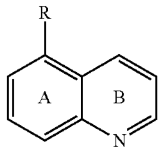

k

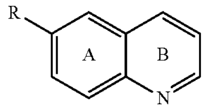

l

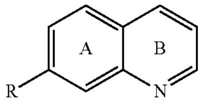

m

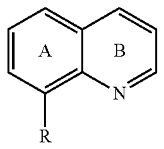

As used herein, the term "subject" refers to an animal Typically the animal is a mammal including a human. A subject also refers to for example, primates (e.g., humans, male or female), cows, sheep, goats, horses, dogs, cats, rabbits, rats, mice, fish, birds, and the like. In a embodiment, the subject is a primate. In another embodiment, the subject is a human.

As used herein, the term "patient" refers to a human (including adults and children) or other animal. In one embodiment, "patient" refers to a human.

The term "Stereoisomer" refers to compounds which have identical chemical constitution, but differ with regard to the arrangement of the atoms or groups in space. Stereoisomers include enantiomers, diastereomers, conformers (rotamers), geometric (cis/trans) isomers, atropisomers, and the like.

The term "Chiral" refers to molecules which have the property of non-superimposability of the mirror image partner, while the term "achiral" refers to molecules which are superimposable on their mirror image partner.

The term "Enantiomer" refers to two stereoisomers of a compound which are non-superimposable mirror images of one another.

The term "Diastereomer" refers to a stereoisomer with two or more centers of chirality and whose molecules are not mirror images of one another. Diastereomers have different physical properties, e.g., melting points, boiling points, spectral properties or biological activities. Mixture of diastereomers may separate under high resolution analytical procedures such as electrophoresis and chromatography such as HPLC.

Stereochemical definitions and conventions used herein generally follow Parker et al., McGraw-Hill Dictionary of Chemical Terms (1984) McGraw-Hill Book Company, New York and Eliel et al., "*Stereochemistry of Organic Compounds*", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−)

or l meaning that the compound is levorotatory. A compound prefixed with (+) or d is dextrorotatory. A specific stereoisomer may be referred to as an enantiomer, and a mixture of such isomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compounds disclosed herein can be present in racemic or enantiomerically enriched, for example the (R)-, (S)- or (R, S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible isomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of isomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., *Enantiomers, Racemates and Resolutions* (Wiley Interscience, New York, 1981); *Principles of Asymmetric Synthesis* ($2^{nd}$ Ed. Robert et al., Elsevier, Oxford, UK, 2012); Eliel et al., *Stereochemistry of Carbon Compounds* (McGraw-Hill, NY, 1962); and Wilen et al., *Tables of Resolving Agents and Optical Resolutions* p. 268 (E. L. Eliel, Ed., Univ. of Notre Dame Press, Notre Dame, Ind., 1972). *Chiral Separation Techniques: A Practical Approach* (Subramanian, G. Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

The term "pharmaceutically acceptable" refers to compounds, materials, compositions and/or dosage forms which are, within the scope of sound medical judgement, suitable for use in contact with the tissues of a subject without excessive toxicity, irritation, allergic response or other problem or complication commensurate with a reasonable benefit/risk ratio, and effective for their intended purpose.

Unless otherwise stated, structures depicted herein are also meant to include all isomeric (e.g., enantiomeric, diastereomeric, and geometric (or conformational)) forms of the structure, for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope of the invention.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Examples of suitable amino-protecting groups include acetyl, trifluoroacetyl, benzoyl, ethoxycarbonyl, t-butoxycarbonyl (BOC), benzyloxycarbonyl (CBZ), 9-fluorenylmethylenoxycarbonyl (Fmoc) and benzyl. Similarly, a "hydroxy-protecting group" refers to a substituent of a hydroxy group that blocks or protects the hydroxy functionality. Examples of suitable hydroxy-protecting groups include trialkylsilyl, acetyl, benzoyl and benzyl. A "carboxy-protecting group" refers to a substituent of the carboxy group that blocks or protects the carboxy functionality. Examples of the carboxy-protecting group include $—CH_2CH_2SO_2Ph$, cyanoethyl, 2-(trimethylsilyl)ethyl, 2-(trimethylsilyl)ethoxymethyl, 2-(p-toluene sulfonyl)ethyl, 2-(p-nitrophenylsulfonyl)ethyl, 2-(diphenylphosphino)ethyl, nitroethyl, and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

The term "prodrug" refers to a compound that is transformed in vivo into a compound of Formula (I) or Formula (II). Such a transformation can be affected, for example, by hydrolysis of the prodrug form in blood or enzymatic transformation of the prodrug form in blood or tissue to the parent form. Prodrugs of the compounds disclosed herein may be, for example, esters. Some common esters which have been utilized as prodrugs are phenyl esters, aliphatic ($C_1$-$C_{24}$) esters, acyloxymethyl esters, carbonates, carbamates and amino acid esters. For example, a compound disclosed herein that contains an OH group may be acylated at this position in its prodrug form. Other prodrug forms include phosphates such as those phosphate compounds derived from the phosphonation of an OH group on the parent compound. A thorough discussion of prodrugs is provided in Higuchi et al., *Pro-drugs as Novel Delivery Systems*, Vol. 14, A.C.S. Symposium Series; Roche et al., ed., *Bioreversible Carriers in Drug Design*, American Pharmaceutical Association and Pergamon Press, 1987; Rautio et al, Prodrugs: Design and Clinical Applications, *Nature*

*Reviews Drug Discovery,* 2008, 7, 255-270, and Hecker et al., Prodrugs of Phosphates and Phosphonates, *J Med. Chem.,* 2008, 51, 2328-2345, all of which are incorporated herein by reference in their entireties.

A "metabolite" is a product produced through metabolism in the body of a specified compound or salt thereof. The metabolite of a compound may be identified using routine techniques known in the art and their activities determined using tests such as those described herein. Such products may result for example from oxidation, reduction, hydrolysis, amidation, deamidation, esterification, deesterification, enzymatic cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salt" refers to organic or inorganic salts of a compound disclosed herein. The pharmaceutically acceptable salts are well known in the art. For example, Berge et al., describe pharmaceutically acceptable salts in detail in *J. Pharm. Sci.,* 1977, 66, 1-19, which is incorporated herein by reference. Some non-limiting examples of the pharmaceutically acceptable salt include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid, or by using other methods used in the art such as ion exchange. Other examples of the pharmaceutically acceptable salt include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Pharmaceutically acceptable salts derived from appropriate bases include alkali metal, alkaline earth metal, ammonium and $N^+(C_1\text{-}C_4\ alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further examples of the pharmaceutically acceptable salt include, when appropriate, nontoxic ammonium, quaternary ammonium, and amine cations formed using counterions such as halide, hydroxide, carboxylate, sulfate, phosphate, nitrate, $C_1$-$C_8$ sulfonate and aryl sulfonate.

A "solvate" refers to an association or complex of one or more solvent molecules and a compound disclosed herein. Some non-limiting examples of solvents that form the solvate include water, isopropanol, ethanol, methanol, DMSO, ethyl acetate, acetic acid, ethanolamine or mixtures thereof.

The term "hydrate" can be used when said solvent is water. In one embodiment, one solvent molecule is associated with one molecule of the compounds disclosed herein, such as a hydrate. In another embodiment, more than one solvent molecule may be associated with one molecule of the compounds disclosed herein, such as a dihydrate. In still another embodiment, less than solvent one molecule may be associated with one molecule of the compounds disclosed herein, such as a hemihydrate. Furthermore, all the solvates of the invention retain the biological effectiveness of the non-hydrate form of the compounds disclosed herein.

The term "preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

The term "therapeutically effective amount" refers to the amount of a compound that, when administered to a subject for treating a disease, is sufficient to effect such treatment for the disease. The "therapeutically effective amount" can vary depending on the compound, the disease and its severity, and the condition, age, weight, gender etc. of the subject to be treated.

"Treating" or "treatment" of a disease state includes: (i) preventing the disease state, i.e., causing the clinical symptoms of the disease state not to develop in a subject that may be exposed to or predisposed to the disease state, but does not yet experience or display symptoms of the disease state, (ii) inhibiting the disease state, i.e., arresting the development of the disease state or its clinical symptoms, or (iii) relieving the disease state, i.e., causing temporary or permanent regression of the disease state or its clinical symptoms.

An "effective amount" or "effective dose" is that amount effective for treating or lessening the severity of one or more of the diseases or disorders disclosed herein. The compounds and compositions, according to the method disclosed herein, may be administered using any amount and any route of administration effective for treating or lessening the severity of the disorder or disease. The exact amount required will vary from subject to subject, depending on the species, age, and the general condition of the subject, the severity of the infection, the particular agent, its mode of administration, and the like. A compound or composition can also be administered with one or more other therapeutic agents, as discussed above.

DESCRIPTION OF COMPOUNDS OF THE INVENTION

Discoursed herein are piperazine compounds, pharmaceutically acceptable salt thereof, pharmaceutical formulations and compositions thereof, which are acting as selective serotonin reuptake inhibitors and/or 5-$HT_{1A}$ receptor agonists and have potential therapeutic uses for the treatment of central nervous system (CNS) dysfunction, such as depression, anxiety disorder or bipolar disorder.

In one aspect, provided herein are compounds having Formula (I) or a stereoisomer, a tautomer, an N-oxide, a solvate, a metabolite, a pharmaceutically acceptable salt or a prodrug thereof, (I)

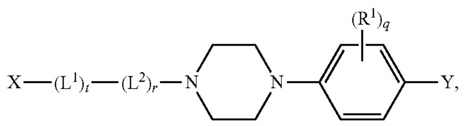

wherein

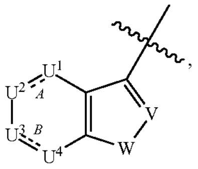

X is wherein each of $\overset{A}{=\!=}$ and $\overset{B}{=\!=}$ is independently a single bond or a double bond;

each of $U^1$, $U^2$, $U^3$ and $U^4$ is independently $CR^2$, N, —$CR^2R^{2a}$— or —$NR^{2b}$—;

or $U^1$ and $U^2$ together or $U^3$ and $U^4$ together independently form —$CR^2R^{2a}$—, —$NR^{2b}$—, —O— or —S—;

V is $CR^2$ or N;

W is $NR^{2b}$, —O— or —S—;

each $L^1$ is —$CR^3R^4$—;

each $L^2$ is —$CR^5R^6$—;

t is 0, 1 or 2;

r is 1, 2, 3, 4 or 5;

q is 1, 2, 3 or 4;

Y is

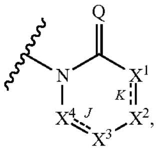

wherein Q is O, S or N($R^7$);

each of $\overset{J}{=\!=}$ and $\overset{K}{=\!=}$ is independently a single bond or a double bond;

each of $X^1$, $X^2$, $X^3$ and $X^4$ is independently —O—, —S—, $CR^8$, N, —$CR^8R^{8a}$— or —$NR^{8b}$—;

or $X^1$ and $X^2$ together or $X^3$ and $X^4$ together independently form —$CR^8R^{8a}$—, —$NR^{8b}$—, —O— or —S—;

each $R^1$ is independently H, D, F, Cl, Br, I, —CN, —$N_3$, —$NO_2$, —$NR^aR^b$, —$OR^c$, alkyl, alkenyl or alkynyl, wherein each of alkyl, alkenyl and alkynyl is optionally and independently substituted with one or more $R^9$;

each $R^2$ and $R^{2a}$ is independently H, D, F, Cl, Br, I, —CN, —$N_3$, —$NO_2$, —$NR^aR^b$, —S(═O)$_m$$R^c$, —C(═O)$R^c$, —C(═O)$OR^c$, —C(═O)$NR^aR^b$, —S(═O)$_2$$NR^aR^b$, —OC(═O)$R^c$, —N($R^a$)C(═O)$R^c$, alkyl, alkenyl or alkynyl, wherein each of alkyl, alkenyl and alkynyl is optionally and independently substituted with one or more $R^9$;

each $R^{2b}$ is independently H, D, F, Cl, Br, I, —CN, —$N_3$, —$NO_2$, —$NR^aR^b$, —S(═O)$_m$$R^c$, —C(═O)$R^c$, —C(═O)$OR^c$, —C(═O)$NR^aR^b$, —S(═O)$_2$$NR^aR^b$, —OC(═O)$R^c$, —N($R^a$)C(═O)$R^c$, alkyl, alkenyl or alkynyl, wherein each of alkyl, alkenyl and alkynyl is optionally and independently substituted with one or more $R^9$;

each $R^3$ and $R^4$ is independently H, D, F, Cl, Br, I, —CN, —$N_3$, —$NH_2$, —OH, alkyl, alkenyl, alkynyl, alkoxy, alkylamino, cycloalkyl, heterocyclyl, aryl or heteroaryl, or $R^3$ and $R^4$, together with the carbon atom to which they are attached, form a carbonyl group, a carbocyclic ring or a heterocyclic ring, wherein each of alkyl, alkenyl, alkynyl, alkoxy, alkylamino, cycloalkyl, heterocyclyl, aryl, heteroaryl, the carbocyclic ring and the heterocyclic ring is optionally and independently substituted with one or more $R^9$;

each $R^5$ and $R^6$ is independently H, D, F, Cl, Br, I, —CN, —$N_3$, —$NH_2$, —OH, alkyl, alkenyl, alkynyl, alkoxy, alkylamino, cycloalkyl, heterocyclyl, aryl or heteroaryl, or $R^5$ and $R^6$, together with the carbon atom to which they are attached, form a carbocyclic ring or a heterocyclic ring, wherein each of alkyl, alkenyl, alkynyl, alkoxy, alkylamino, cycloalkyl, heterocyclyl, aryl, heteroaryl, the carbocyclic ring and the heterocyclic ring is optionally and independently substituted with one or more $R^9$;

$R^7$ is H, —OH, —$NH_2$, $C_1$-$C_4$ alkyl, $C_1$-$C_4$ haloalkyl or $C_1$-$C_4$ alkylamino;

each $R^8$ and $R^{8a}$ is independently H, D, F, Cl, Br, I, —CN, —$N_3$, —$NO_2$, —($C_0$-$C_6$ alkylene)-$NR^aR^b$, —($C_0$-$C_6$ alkylene)-$OR^c$, —($C_0$-$C_6$ alkylene)-S(═O)$_m$$R^c$, —C(═O)$R^c$, —C(═O)$OR^c$, —C(═O)$NR^aR^b$, —S(═O)$_2$$NR^aR^b$, —OC(═O)$R^c$, —N($R^a$)C(═O)$R^c$, alkyl, alkenyl, alkynyl, cycloalkyl, heterocyclyl, aryl or heteroaryl;

each $R^{8b}$ is independently H, D, F, Cl, Br, I, —CN, —$N_3$, —$NO_2$, —($C_0$-$C_6$ alkylene)-$NR^aR^b$, —($C_0$-$C_6$ alkylene)-$OR^c$, —($C_0$-$C_6$ alkylene)-S(═O)$_m$$R^c$, —C(═O)$R^c$, —C(═O)$OR^c$, —C(═O)$NR^aR^b$, —S(═O)$_2$$NR^aR^b$, —OC(═O)$R^c$, —N($R^a$)C(═O)$R^c$, alkyl, alkenyl, alkynyl, cycloalkyl, heterocyclyl, aryl or heteroaryl;

or two $R^8$ on two adjacent ring atoms, or two $R^{8b}$ on two adjacent ring atoms, or $R^8$ and $R^{8b}$ on two adjacent ring atoms, together with the ring atoms to which they are attached, independently form a carbocyclic ring, a heterocyclic ring, an aryl ring or a heteroaryl ring, wherein each of the carbocyclic ring, the heterocyclic ring, the aryl ring and the heteroaryl ring is optionally and independently substituted with one or more substituents independently selected from $R^x$ and $R^y$;

each $R^9$ is independently F, Cl, Br, I, —CN, —$N_3$, —$NO_2$, —OH, —SH, —$NH_2$, alkyl, haloalkyl, alkoxy, alkylthio or alkylamino;

each $R^x$ is independently H, D, F, Cl, Br, I, —CN, —$N_3$, —$NO_2$, —$NR^aR^b$, —$SR^c$, —C(═O)$NR^aR^b$, —C(═O)$OR^c$, —O—($C_0$-$C_6$ alkylnene)-C(═O)$NR^aR^b$, —O—($C_0$-$C_6$ alkylene)-C(═O)$OR^c$, alkyl or haloalkyl;

each $R^y$ is independently H, D, F, Cl, Br, I, —CN, —$N_3$, —$NO_2$, —$NR^aR^b$, —$SR^c$, —C(═O)$NR^aR^b$, —C(═O)$OR^c$, —O—($C_0$-$C_6$ alkylnene)-C(═O)$NR^aR^b$, —O—($C_0$-$C_6$ alkylene)-C(═O)$OR^c$, alkyl or haloalkyl;

each $R^a$ and $R^b$ is independently H, alkyl, alkenyl, alkynyl, haloalkyl, —($C_0$-$C_6$ alkylene)-cycloalkyl, —($C_0$-$C_6$ alkylene)-heterocyclyl, —($C_0$-$C_6$ alkylene)-aryl or —($C_0$-$C_6$ alkylene)-heteroaryl, or $R^a$ and $R^b$, together with the nitrogen atom to which they are attached, form a heterocyclic ring;

each $R^c$ is independently H, alkyl, alkenyl, alkynyl, haloalkyl, —($C_0$-$C_6$ alkylene)-cycloalkyl, —($C_0$-$C_6$ alkylene)-heterocyclyl, —($C_0$-$C_6$ alkylene)-aryl or —($C_0$-$C_6$ alkylene)-heteroaryl; and each m is independently 0, 1 or 2.

In one embodiment, each $R^1$ is independently H, D, F, Cl, Br, I, —CN, —$N_3$, —$NO_2$, —$NR^aR^b$, $C_1$-$C_6$ alkyl, $C_2$-$C_6$ alkenyl or $C_2$-$C_6$ alkynyl, wherein each of $C_1$-$C_6$ alkyl, $C_2$-$C_6$ alkenyl and $C_2$-$C_6$ alkynyl is optionally and independently substituted with one or more $R^9$.

In another embodiment, X is

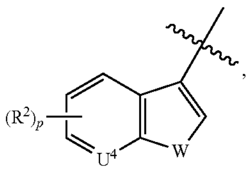

wherein $U^4$ is $CR^2$ or N;

p is 1, 2 or 3; and

W is —NH—, —O— or —S—.

In another embodiment, each $R^2$ and $R^{2a}$ is independently H, D, F, Cl, Br, I, —CN, —$N_3$, —$NO_2$, —$NR^aR^b$, —$OR^c$, —$S(=O)_mR^c$, —$C(=O)R^c$, —$C(=O)OR^c$, —$C(=O)NR^aR^b$, —$S(=O)_2NR^aR^b$, —$OC(=O)R^c$, —$N(R^a)C(=O)R^c$, $C_1$-$C_6$ alkyl, $C_2$-$C_6$ alkenyl or $C_2$-$C_6$ alkynyl, wherein each of $C_1$-$C_6$ alkyl, $C_2$-$C_6$ alkenyl and $C_2$-$C_6$ alkynyl is optionally and independently substituted with one or more $R^9$; and each $R^{2b}$ is independently H, D, F, Cl, Br, I, —CN, —$N_3$, —$NO_2$, —$NR^aR^b$, —$S(=O)_mR^c$, —$C(=O)R^c$, —$C(=O)OR^c$, —$C(=O)NR^aR^b$, —$S(=O)_2NR^aR^b$, —$OC(=O)R^c$, —$N(R^a)C(=O)R^c$, $C_1$-$C_6$ alkyl, $C_2$-$C_6$ alkenyl or $C_2$-$C_6$ alkynyl, wherein each of $C_1$-$C_6$ alkyl, $C_2$-$C_6$ alkenyl and $C_2$-$C_6$ alkynyl is optionally and independently substituted with one or more $R^9$.

In another embodiment, each $R^3$ and $R^4$ is independently H, D, F, Cl, Br, I, —CN, —$N_3$, —$NH_2$, —OH, $C_1$-$C_6$ alkyl, $C_2$-$C_6$ alkenyl, $C_2$-$C_6$ alkynyl, $C_1$-$C_6$ alkoxy, $C_1$-$C_6$ alkylamino, $C_3$-$C_{10}$ cycloalkyl, 3-10 membered heterocyclyl, $C_6$-$C_{10}$ aryl or 5-10 membered heteroaryl, or $R^3$ and $R^4$, together with the carbon atom to which they are attached, form a carbonyl group, a $C_3$-$C_8$ carbocyclic ring or a 3-7 membered heterocyclic ring, wherein each of $C_1$-$C_6$ alkyl, $C_2$-$C_6$ alkenyl, $C_2$-$C_6$ alkynyl, $C_1$-$C_6$ alkoxy, $C_1$-$C_6$ alkylamino, $C_3$-$C_{10}$ cycloalkyl, 3-10 membered heterocyclyl, $C_6$-$C_{10}$ aryl, 5-10 membered heteroaryl, the $C_3$-$C_8$ carbocyclic ring and the 3-7 membered heterocyclic ring is optionally and independently substituted with one or more $R^9$.

In another embodiment, each $R^5$ and $R^6$ is independently H, D, F, Cl, Br, I, —CN, —$N_3$, —$NH_2$, —OH, $C_1$-$C_6$ alkyl, $C_2$-$C_6$ alkenyl, $C_2$-$C_6$ alkynyl, $C_1$-$C_6$ alkoxy, $C_1$-$C_6$ alkylamino, $C_3$-$C_{10}$ cycloalkyl, 3-10 membered heterocyclyl, $C_6$-$C_{10}$ aryl or 5-10 membered heteroaryl, or $R^5$ and $R^6$, together with the carbon atom to which they are attached, form a $C_3$-$C_8$ carbocyclic ring or a 3-7 membered heterocyclic ring, wherein each of $C_1$-$C_6$ alkyl, $C_2$-$C_6$ alkenyl, $C_2$-$C_6$ alkynyl, $C_1$-$C_6$ alkoxy, $C_1$-$C_6$ alkylamino, $C_3$-$C_{10}$ cycloalkyl, 3-10 membered heterocyclyl, $C_6$-$C_{10}$ aryl, 5-10 membered heteroaryl, $C_3$-$C_8$ carbocyclic ring and 3-7 membered heterocyclic ring is optionally and independently substituted with one or more $R^9$.

In another embodiment, each $R^8$ and $R^{8a}$ is independently H, D, F, Cl, Br, I, —CN, —$N_3$, —$NO_2$, —($C_0$-$C_6$ alkylene)-$NR^aR^b$, —($C_0$-$C_6$ alkylene)-$OR^c$, —($C_0$-$C_6$ alkylene)-$S(=O)_mR^c$, —$C(=O)R^c$, —$C(=O)OR^c$, —$C(=O)NR^aR^b$, —$S(=O)_2NR^aR^b$, —$OC(=O)R^c$, —$N(R^a)C(=O)R^c$, $C_1$-$C_6$ alkyl, $C_2$-$C_6$ alkenyl, $C_2$-$C_6$ alkynyl, $C_3$-$C_{10}$ cycloalkyl, 3-10 membered heterocyclyl, $C_6$-$C_{10}$ aryl or 5-10 membered heteroaryl;

each $R^{8b}$ is independently H, D, F, Cl, Br, I, —CN, —$N_3$, —$NO_2$, —($C_0$-$C_6$ alkylene)-$NR^aR^b$, —($C_0$-$C_6$ alkylene)-$OR^c$, —($C_0$-$C_6$ alkylene)-$S(=O)_mR^c$, —$C(=O)R^c$, —$C(=O)OR^c$, —$C(=O)NR^aR^b$, —$S(=O)_2NR^aR^b$, —$OC(=O)R^c$, —$N(R^a)C(=O)R^c$, $C_1$-$C_6$ alkyl, $C_2$-$C_6$ alkenyl, $C_2$-$C_6$ alkynyl, $C_3$-$C_{10}$ cycloalkyl, 3-10 membered heterocyclyl, $C_6$-$C_{10}$ aryl or 5-10 membered heteroaryl; and or two $R^8$ on two adjacent ring atoms, or two $R^{8b}$ on two adjacent ring atoms, or $R^8$ and $R^{8b}$ on two adjacent ring atoms, together with the ring atoms to which they are attached, independently form a $C_3$-$C_{10}$ carbocyclic ring, a 3-10 membered heterocyclic ring, a $C_6$-$C_{10}$ aryl ring or a 5-10 membered heteroaryl ring, wherein each of the $C_3$-$C_{10}$ carbocyclic ring, the 3-10 membered heterocyclic ring, the $C_6$-$C_{10}$ aryl ring and the 5-10 membered heteroaryl ring is optionally and independently substituted with one or more substituents independently selected from $R^x$ and $R^y$.

In another embodiment, each $R^9$ is independently F, Cl, Br, I, —CN, —$N_3$, —$NO_2$, —OH, —SH, —$NH_2$, $C_1$-$C_6$ alkyl, $C_1$-$C_6$ haloalkyl, $C_1$-$C_6$ alkoxy, $C_1$-$C_6$ alkylthio or $C_1$-$C_6$ alkylamino.

In another embodiment, each $R^x$ is independently H, D, F, Cl, Br, I, —CN, —$N_3$, —$NO_2$, —$NR^aR^b$, —SW, —$C(=O)NR^aR^b$, —$C(=O)OR^c$, —O—($C_0$-$C_6$ alkylnene)-$C(=O)NR^aR^b$, —O—($C_0$-$C_6$ alkylene)-$C(=O)OR^c$, $C_1$-$C_6$ alkyl or $C_1$-$C_6$ haloalkyl;

each $R^y$ is independently H, D, F, Cl, Br, I, —CN, —$N_3$, —$NO_2$, —$NR^aR^b$, —$SR^c$, —$C(=O)NR^aR^b$, —$C(=O)OR^c$, —O—($C_0$-$C_6$ alkylnene)-$C(=O)NR^aR^b$, —O—($C_0$-$C_6$ alkylene)-$C(=O)OR^c$, $C_1$-$C_6$ alkyl or $C_1$-$C_6$ haloalkyl.

In another embodiment, the compounds disclosed herein have Formula (II) or a stereoisomer, a tautomer, an N-oxide, a solvate, a metabolite, a pharmaceutically acceptable salt or a prodrug thereof, (II)

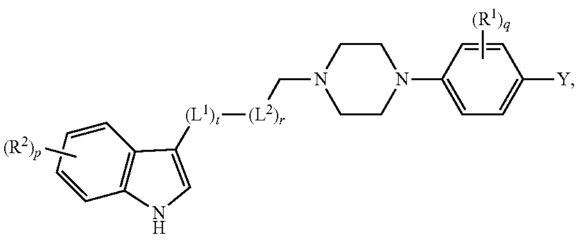

wherein p is 1, 2 or 3; and r is 1, 2, 3 or 4.

In another embodiment, each $R^1$ is independently H, D, F, Cl, Br, —CN, —$NO_2$, —$OR^c$ or $C_1$-$C_4$ alkyl, wherein $C_1$-$C_4$ alkyl is optionally substituted with one or more $R^9$.

In another embodiment, each $R^1$ is independently H, D, F, Cl, Br, —CN, —$NO_2$, -Me, —$CF_3$ or —OMe.

In another embodiment, each $R^2$ and $R^{2a}$ is independently H, D, F, Cl, Br, —CN, —$NO_2$, —$NR^aR^b$, —$C(=O)OR^c$, —$C(=O)NR^aR^b$ or $C_1$-$C_4$ alkyl, wherein the $C_1$-$C_4$ alkyl is optionally substituted with one or more $R^9$; and each $R^{2b}$ is independently H, D, F, Cl, Br, —CN, —$NO_2$, —$NR^aR^b$, —$OR^c$, —$C(=O)OR^c$, —$C(=O)NR^aR^b$ or $C_1$-$C_4$ alkyl, wherein the $C_1$-$C_4$ alkyl is optionally substituted with one or more $R^9$.

In another embodiment, each $R^2$ and $R^{2a}$ is independently H, D, F, Cl, Br, —CN, —$NO_2$, —$NH_2$, —$NMe_2$, —OH, —OMe, —O(i-Pr), -Me, -Et, -(i-Pr), —$CF_3$, —C(═O)OH, —C(═O)OMe or —$CONH_2$; and each $R^{2b}$ is independently H, D, F, Cl, Br, —CN, —$NO_2$, —$NH_2$, —$NMe_2$, —OH, —OMe, —O(i-Pr), -Me, -Et, -(i-Pr), —$CF_3$, —C(═O)OH, —C(═O)OMe or —$CONH_2$.

In another embodiment, each $L^1$ is —$CH_2$—, —C(═O)— or —CH(OH)—.

In another embodiment, each $L^2$ is —$CH_2$—.

In another embodiment, Y is

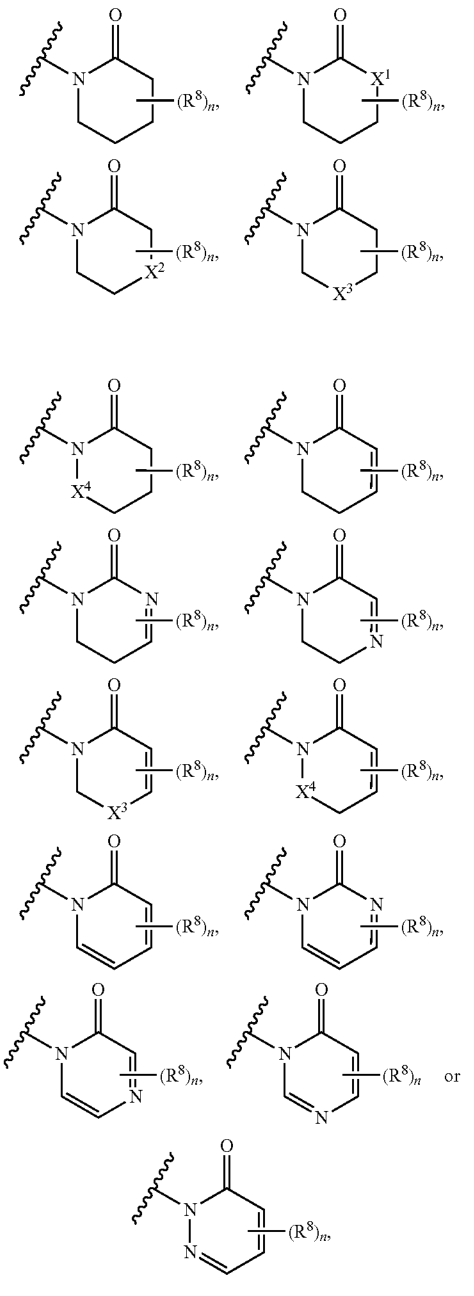

wherein each $X^1$, $X^2$, $X^3$ and $X^4$ is independently —O—, —S— or —$NR^{8b}$—; and each n is independently 1, 2, 3 or 4.

In another embodiment, Y is

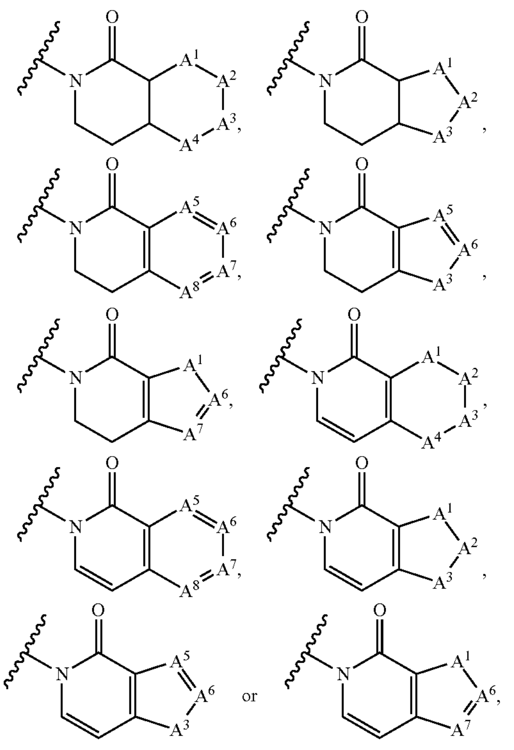

wherein each $A^1$, $A^2$, $A^3$ and $A^4$ is independently —O—, —S—, —$NR^y$— or —$CHR^x$—; and each $A^5$, $A^6$, $A^7$ and $A^8$ is independently N or $CR^x$.

In another embodiment, each $R^8$ and $R^{8a}$ is independently H, D, F, Cl, Br, —CN, —$NO_2$, —($C_0$-$C_4$ alkylene)-$OR^c$, —($C_0$-$C_4$ alkylene)-$NR^aR^b$, —C(═O)$OR^c$, —C(═O)$NR^aR^b$, $C_1$-$C_4$ alkyl, $C_2$-$C_4$ alkenyl or $C_2$-$C_4$ alkynyl;

each $R^{8b}$ is independently H, D, F, Cl, Br, —CN, —$NO_2$, —($C_0$-$C_4$ alkylene)-$OR^c$, —($C_0$-$C_4$ alkylene)-$NR^aR^b$, —C(═O)$OR^c$, —C(═O)$NR^aR^b$, $C_1$-$C_4$ alkyl, $C_2$-$C_4$ alkenyl or $C_2$-$C_4$ alkynyl; and or two $R^8$ on two adjacent ring atoms, or two $R^{8b}$ on two adjacent ring atoms, or $R^8$ and $R^{8b}$ on two adjacent ring atoms, together with the ring atoms to which they are attached, independently form a $C_3$-$C_8$ carbocyclic ring, a 3-7 membered heterocyclic ring, a benzene ring or a 5-6 membered heteroaryl ring, wherein each of the $C_3$-$C_8$ carbocyclic ring, the 3-7 membered heterocyclic ring, the benzene ring and the 5-6 membered heteroaryl ring is optionally and independently substituted with one or more substituents independently selected from $R^x$ and R.

In another embodiment, each $R^8$ and $R^{8a}$ is independently H, D, F, Cl, Br, —CN, —$NO_2$, —OH, —$NH_2$, —C(═O)OMe, —C(═O)OEt, —C(═O)$NH_2$, -Me, -Et, -(i-Pr), —OMe, —O(i-Pr) or —$NMe_2$; and each $R^{8b}$ is independently H, D, F, Cl, Br, —CN, —$NO_2$, —OH, —$NH_2$, —C(═O)OMe, —C(═O)OEt, —C(═O)$NH_2$, -Me, -Et, -(i-Pr), —OMe, —O(i-Pr) or —$NMe_2$.

In another embodiment, each $R^x$ is independently H, D, F, Cl, Br, —CN, —$NO_2$, —$NR^aR^b$, —SW, —C(═O)$NR^aR^b$, —C(═O)$OR^c$, —O—($C_0$-$C_4$ alkylnene)-C(═O)$NR^aR^b$, —O—($C_0$-$C_4$ alkylene)-C(═O)$OR^c$, $C_1$-$C_4$ alkyl or $C_1$-$C_4$ haloalkyl; and each $R^y$ is independently H, D, F, Cl, Br, —CN, —$NO_2$, —$NR^aR^b$, —$SR^c$, —C(═O)$NR^aR^b$, —C(═O)$OR^c$, —O—($C_0$-$C_4$ alkylnene)-C(═O)NR$^a$R$^b$, —O—($C_0$-$C_4$ alkylene)-C(═O)OR$^c$, $C_1$-$C_4$ alkyl or $C_1$-$C_4$ haloalkyl.

In another embodiment, each R$^x$ is independently H, D, F, Cl, Br, —CN, —$NO_2$, —OH, —OMe, —$NH_2$, —$NMe_2$, —COOH, —C(═O)OMe, —C(═O)OEt, —C(═O)$NH_2$, —$OCH_2COOH$, —$OCH_2$C(═O)OMe, —$OCH_2$C(═O)OEt, —$OCH_2$C(═O)$NH_2$, -Me, -Et, -(i-Pr) or —$CF_3$; and each R$^y$ is independently H, D, F, Cl, Br, —CN, —$NO_2$, —OH, —OMe, —$NH_2$, —$NMe_2$, —COOH, —C(═O)OMe, —C(═O)OEt, —C(═O)$NH_2$, —$OCH_2COOH$, —$OCH_2$C(═O)OMe, —$OCH_2$C(═O)OEt, —$OCH_2$C(═O)$NH_2$, -Me, -Et, -(i-Pr) or —$CF_3$.

In another embodiment, each R$^a$ and R$^b$ is independently H, $C_1$-$C_4$ alkyl, $C_2$-$C_4$ alkenyl, $C_2$-$C_4$ alkynyl, $C_1$-$C_4$ haloalkyl, —($C_0$-$C_4$ alkylene)-($C_3$-$C_8$ cycloalkyl), —($C_0$-$C_4$ alkylene)-(3-7 membered heterocyclyl), —($C_0$-$C_4$ alkylene)-(phenyl) or —($C_0$-$C_4$ alkylene)-(5-6 membered heteroaryl), or R$^a$ and R$^b$, together with the nitrogen atom to which they are attached, form a 3-7 membered heterocyclic ring; and each R$^c$ is independently H, $C_1$-$C_4$ alkyl, $C_2$-$C_4$ alkenyl, $C_2$-$C_4$ alkynyl, $C_1$-$C_4$ haloalkyl, —($C_0$-$C_4$ alkylene)-($C_3$-$C_8$ cycloalkyl), —($C_0$-$C_4$ alkylene)-(3-7 membered heterocyclyl), —($C_0$-$C_4$ alkylene)-(phenyl) or —($C_0$-$C_4$ alkylene)-(5-6 membered heteroaryl).

In another embodiment, the compounds disclosed herein have one of the following structures:

(1)

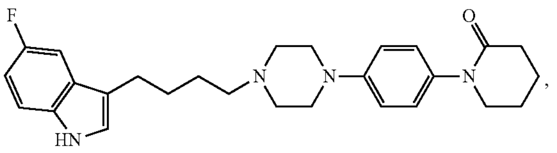

(2)

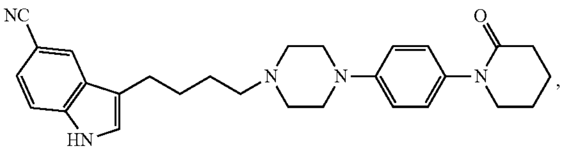

(3)

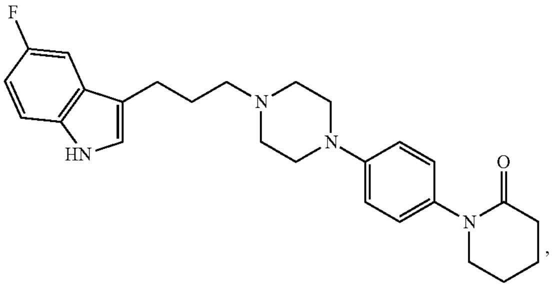

(4)

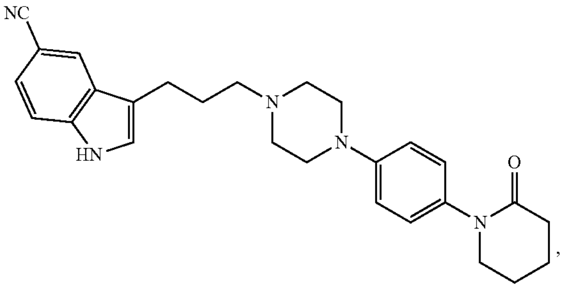

(5)

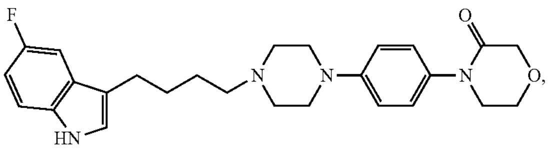

(6)

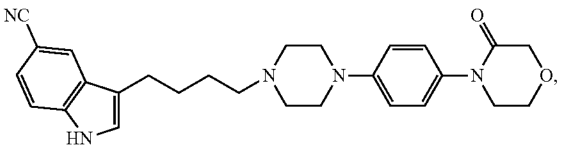

(7)

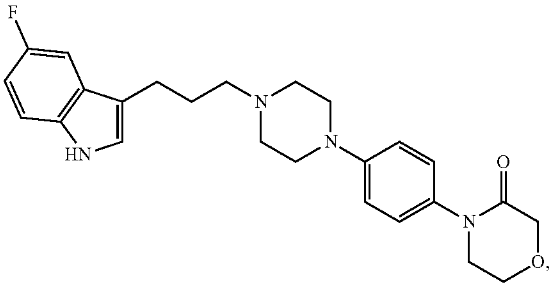

(8)

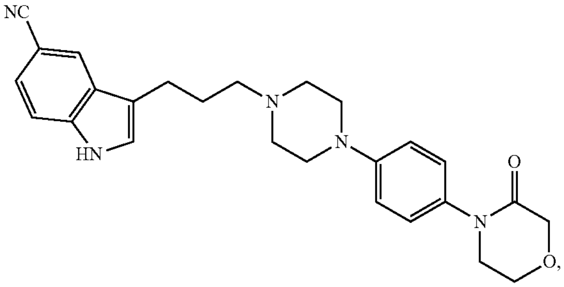

(9)

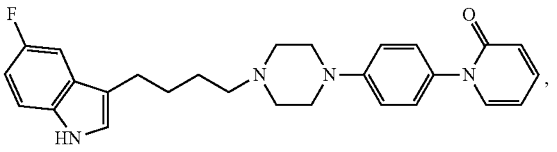

(10)

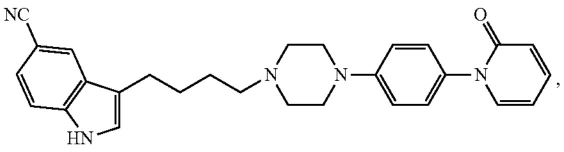

-continued
(11)
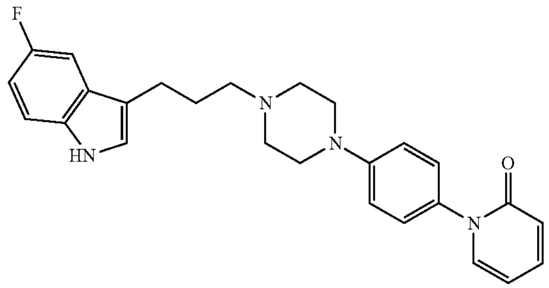
,
(12)
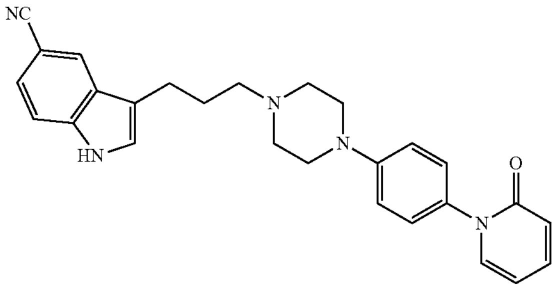
,
(13)
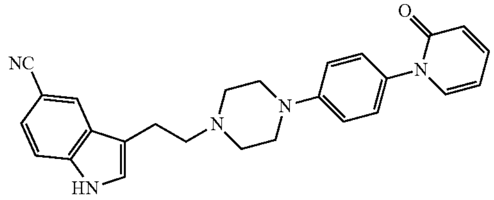
,
(14)
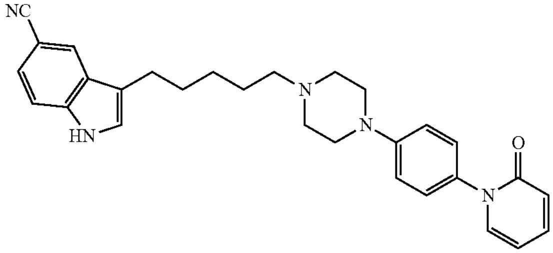
,
(15)
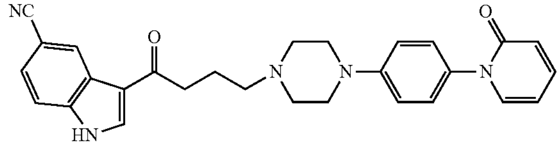
,
(16)
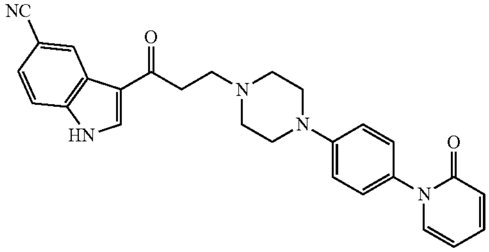
,
(17)
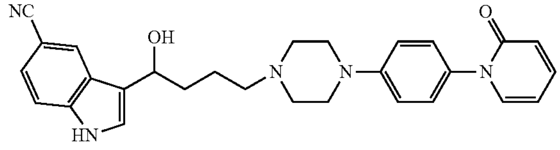
,
(18)
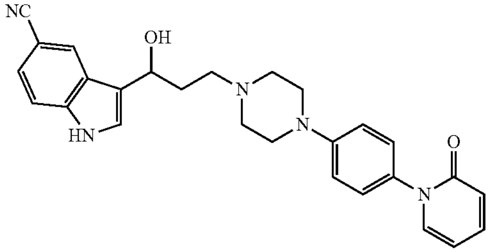
,
(19)
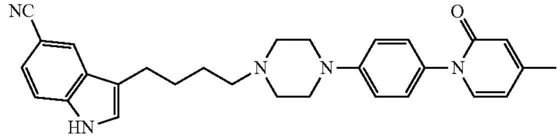
,
(20)
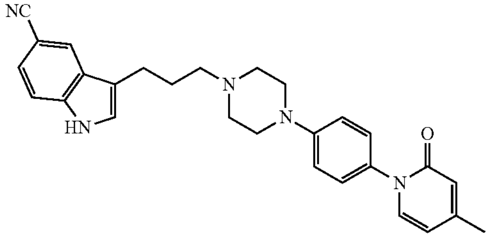
, -continued
(21)
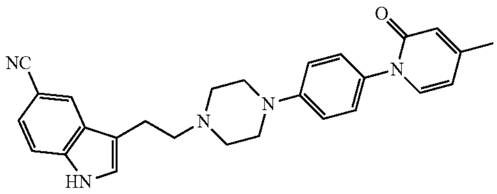
,
(22)
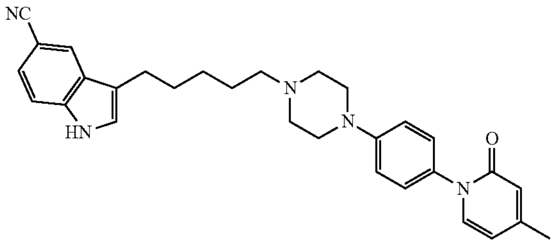
,
(23)
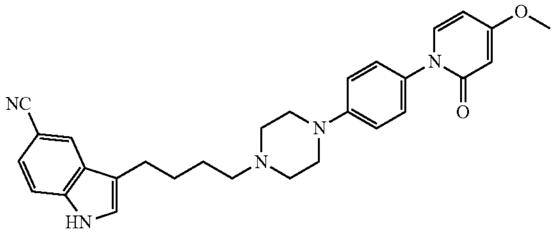
,
(24)
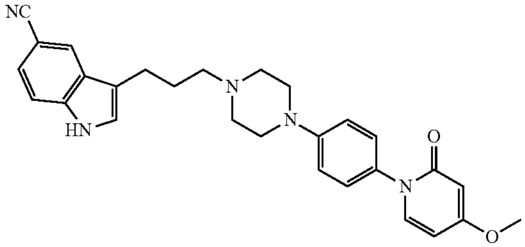
,
(25)
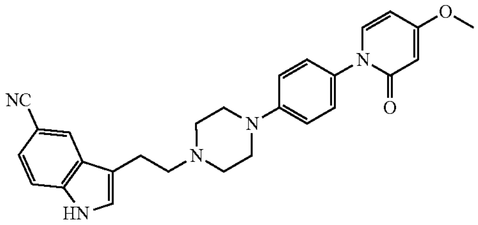
,
(26)
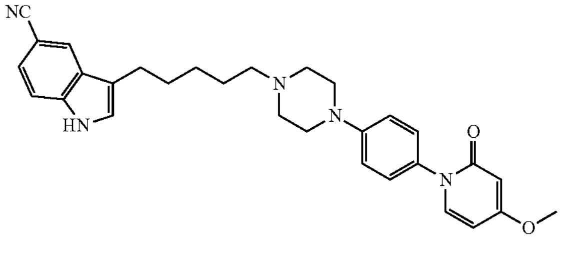
,
(27)
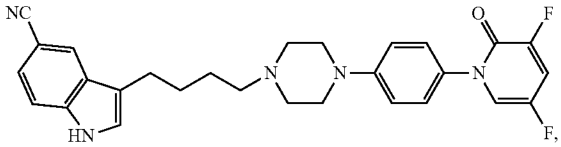
,
(28)
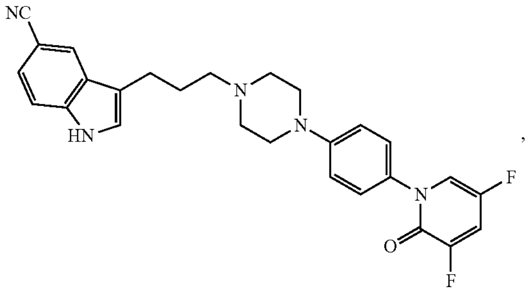
,
(29)
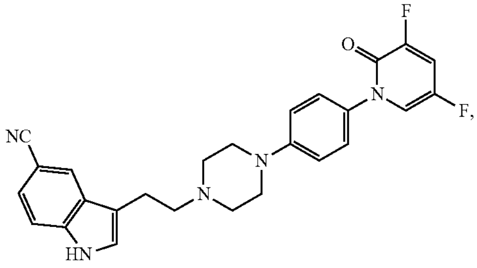
,
(30)
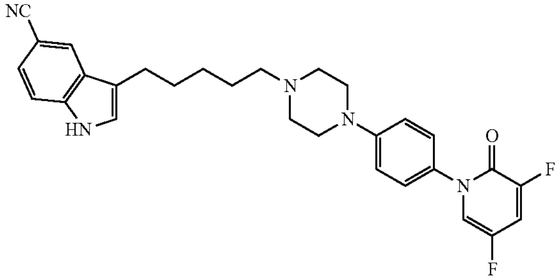
, -continued
(31)
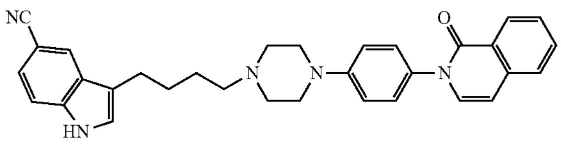
,
(32)
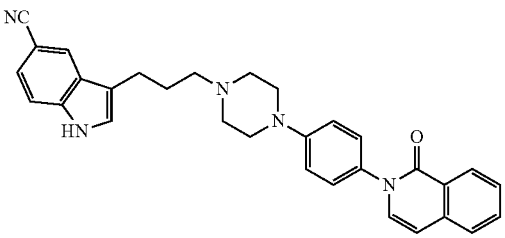
,
(33)
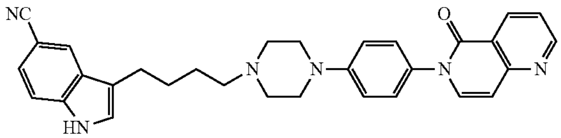
,
(34)
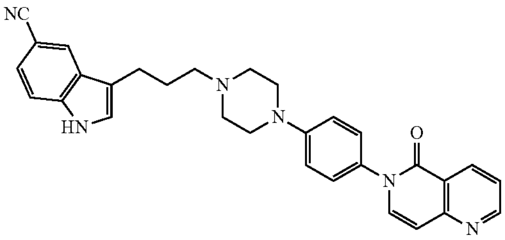
,
(35)
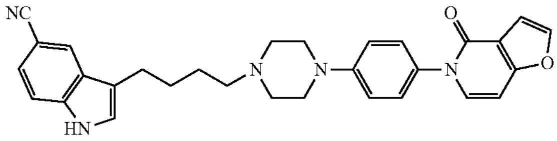
,
(36)
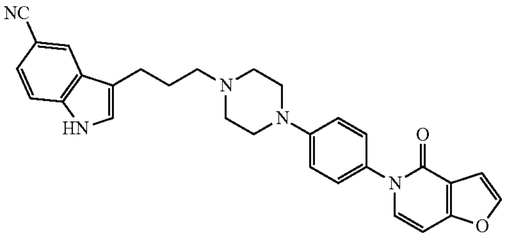
,
(37)
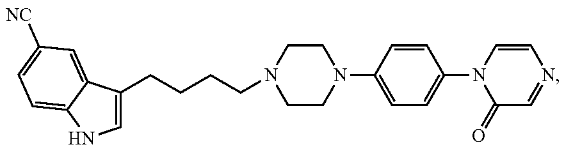
,
(38)
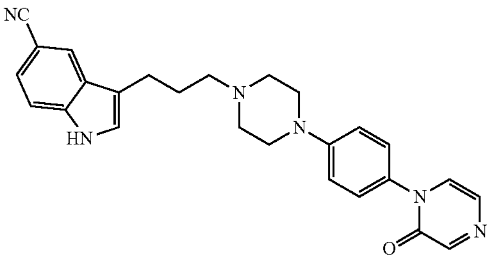
,
(39)
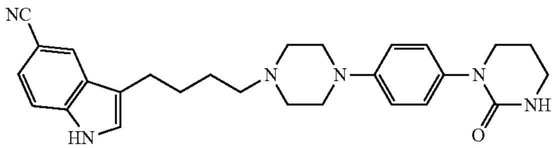
,
(40)
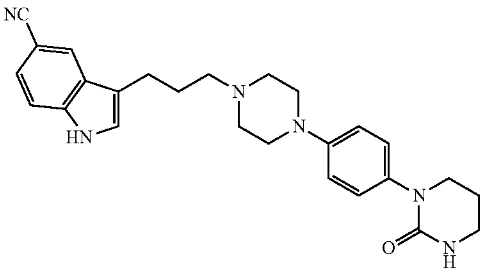
,
(41)
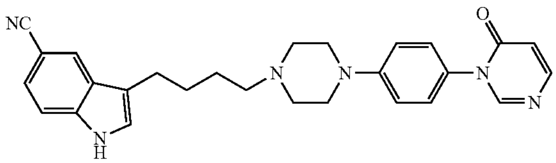
,
(42)
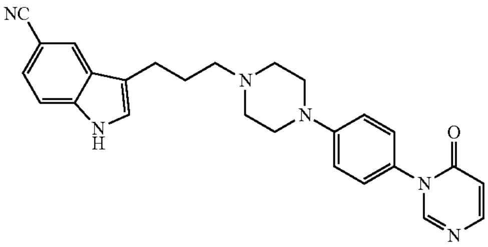
, -continued
(43)
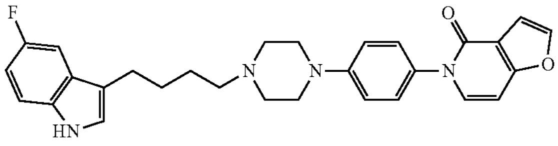,
(44)
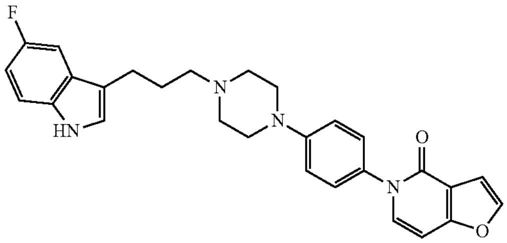,
(45)
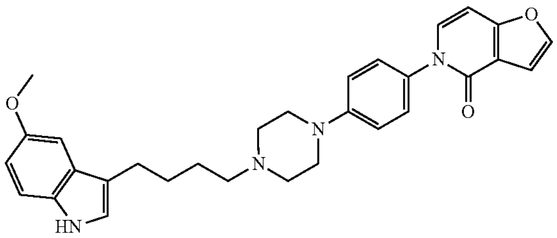,
(46)
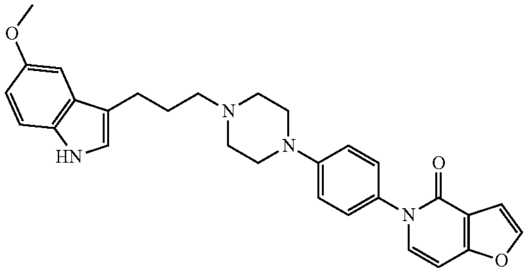,
(47)
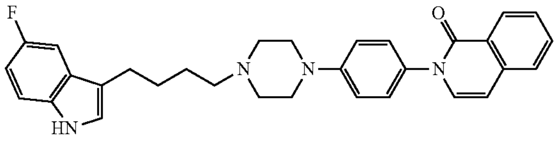,
(48)
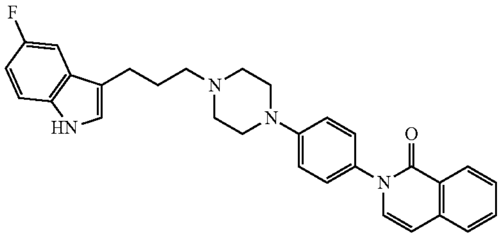,
(49)
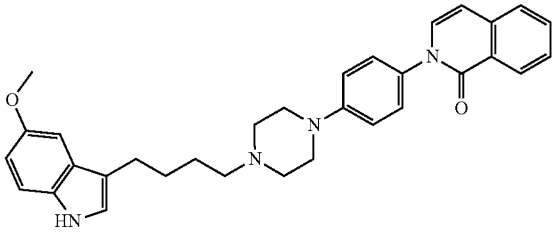,
(50)
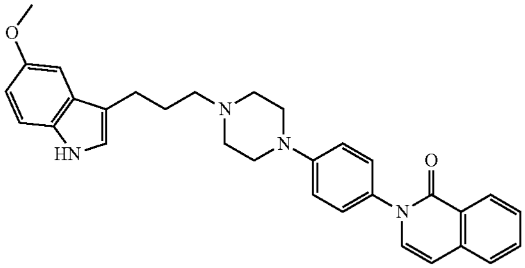,
(51)
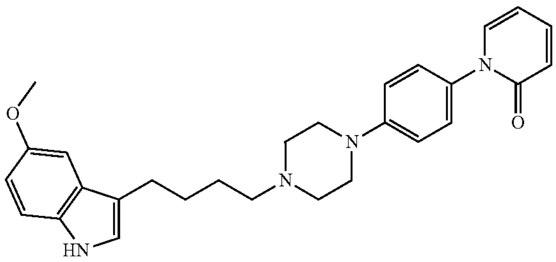,
(52)
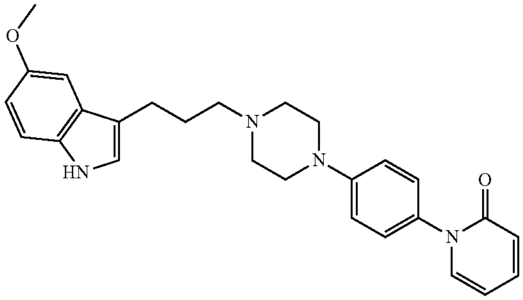, -continued
(53)
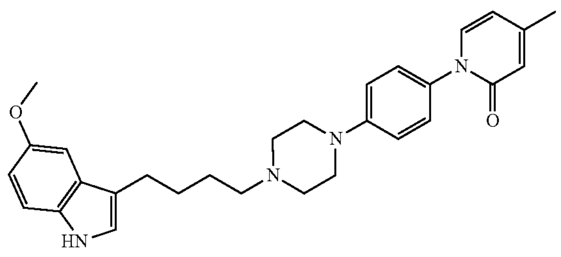
,
(54)
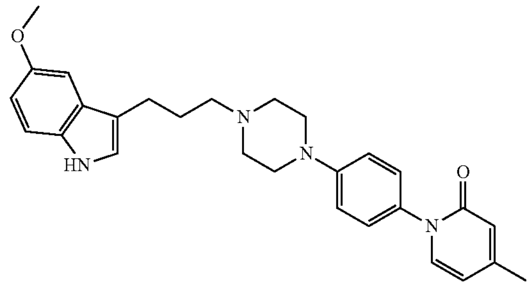
,
(55)
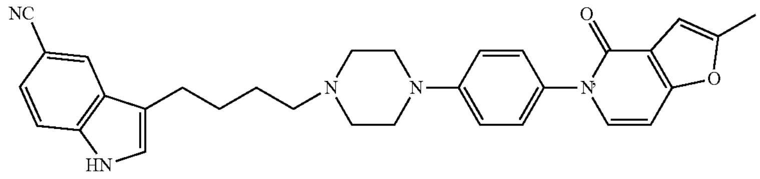
,
(56)
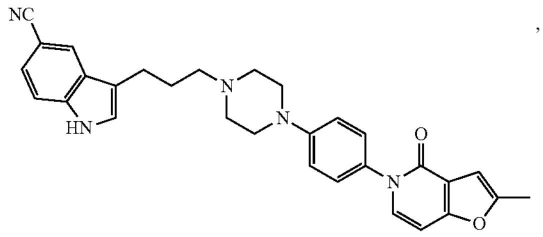
,
(57)
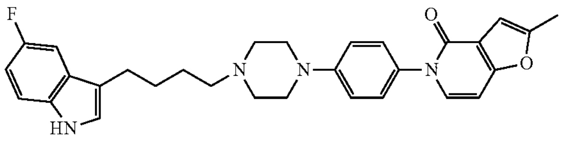
,
(58)
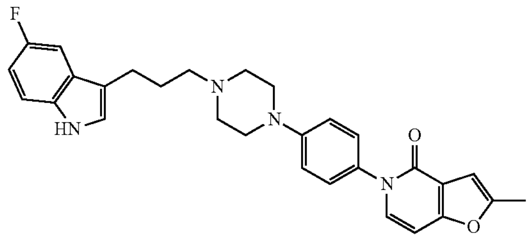
,
(59)
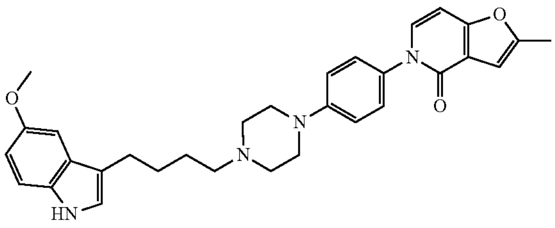
,
(60)
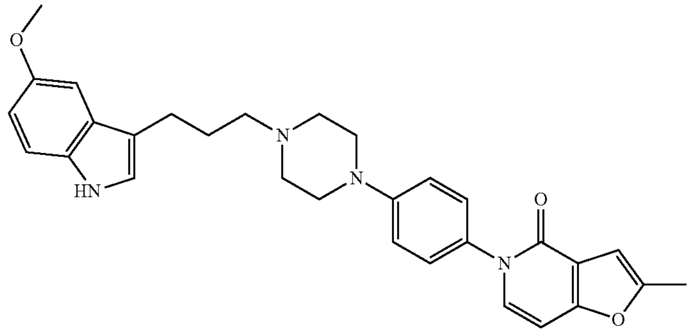
, -continued
(61)
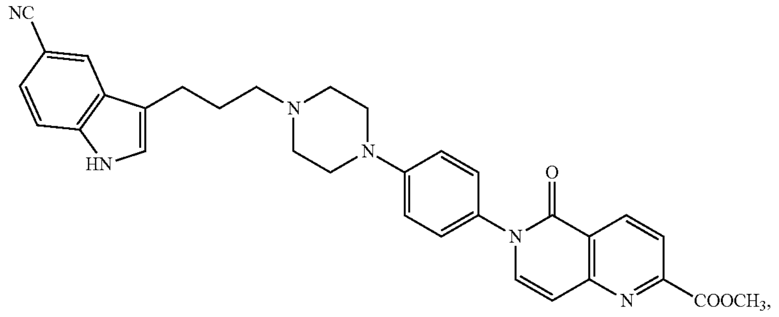
(62)
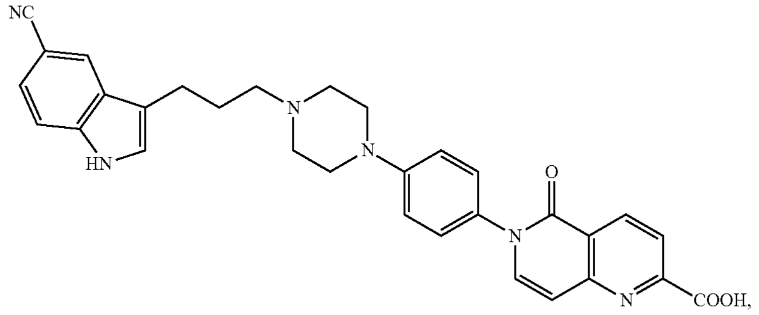
(63)
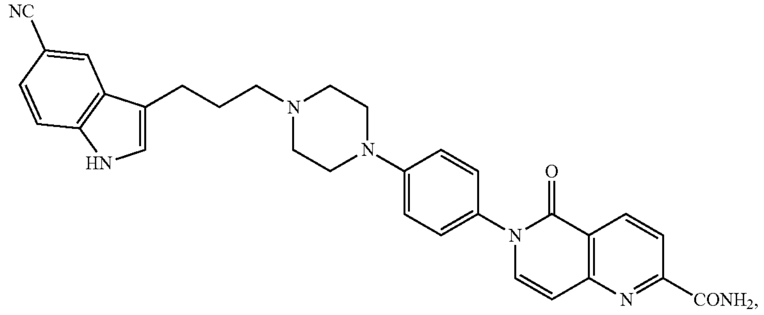
(64)
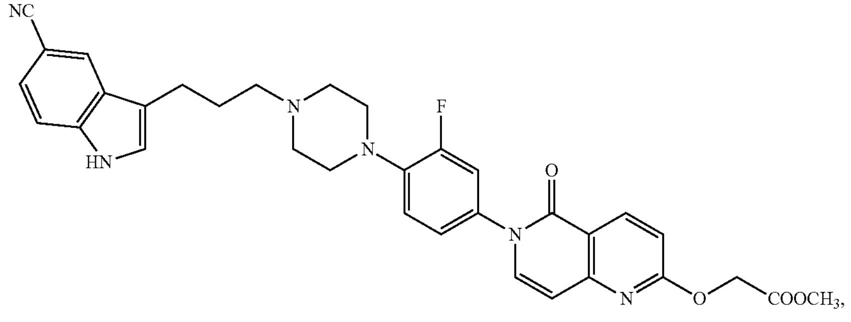
(65)
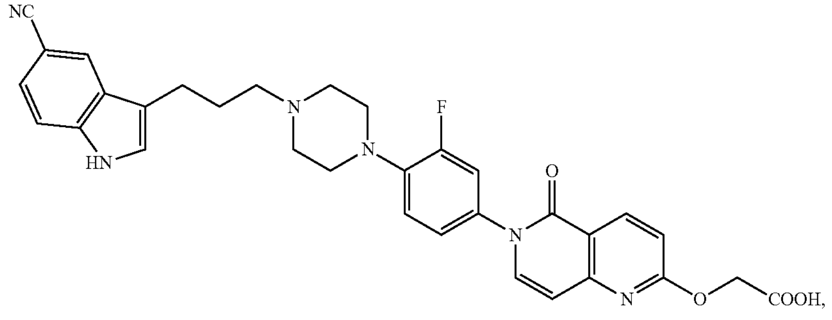

-continued (66)

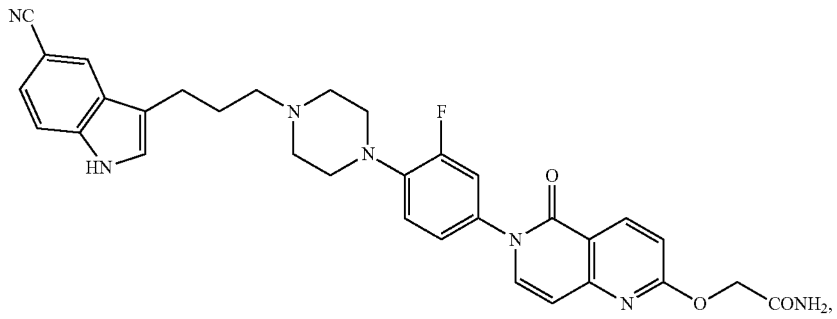

, (67)

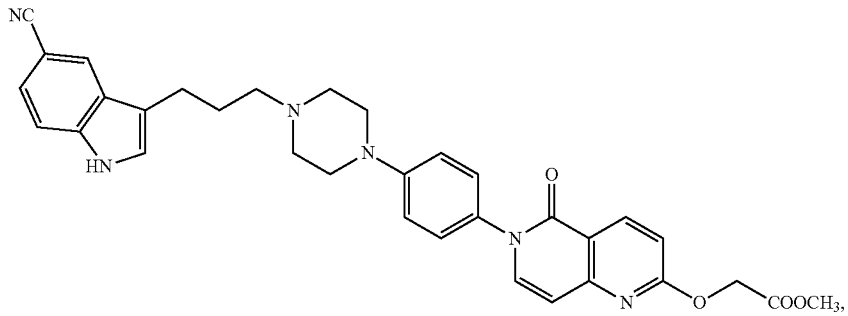

, (68)

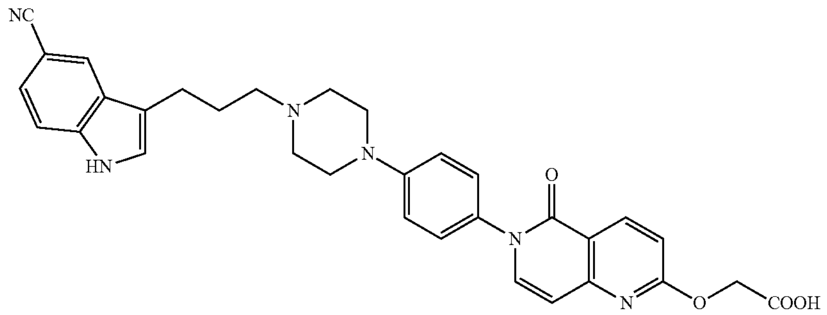

and (69)

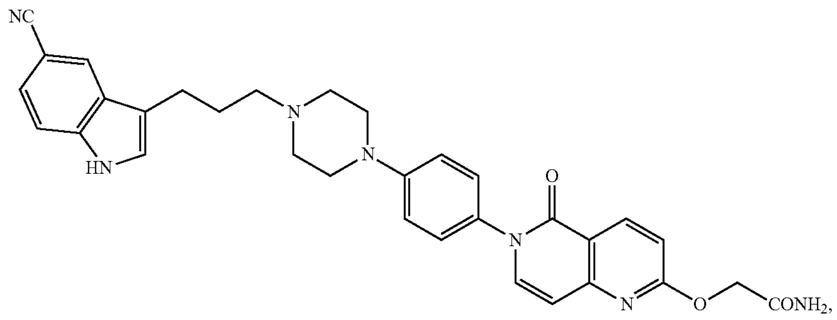

, or a stereoisomer, a tautomer, an N-oxide, a solvate, a metabolite, a pharmaceutically acceptable salt or a prodrug thereof.

Unless otherwise stated, all suitable isotopic variations, all stereoisomers, tautomers, solvates, metabolites, salts and pharmaceutically acceptable prodrugs of the compounds disclosed herein are within the scope of the invention.

The compounds disclosed herein may contain asymmetric or chiral centers, and therefore exist in different stereoisomeric forms. It is intended that all stereoisomeric forms of the compounds of Formula (I) or (II), including but not limited to, diastereomers, enantiomers, atropisomers and geometric (conformational) isomers as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of Formula (I) or (II) may exist in different tautomeric forms, and all such forms are embraced within the scope of the invention, as defined by the claims.

N-oxides of the compounds disclosed herein are also within the scope of the invention and may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

The compounds of Formula (I) or (II) can be in the form of salts. In one embodiment, the salts are pharmaceutically acceptable salts. The phrase "pharmaceutically acceptable" indicates that the substance or composition must be compatible chemically and/or toxicologically, with the other ingredients comprising a formulation, and/or the mammal being treated therewith. In another embodiment, the salts are not necessarily pharmaceutically acceptable salts, and which may be useful as intermediates for preparing and/or purifying compounds of Formula (I) or (II) and/or for separating enantiomers of compounds of Formula (I) or (II).

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc and copper; particularly suitable salts include ammonium, potassium, sodium, calcium and magnesium salts.

Organic bases from which salts can be derived include, for example, primary, secondary and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol or acetonitrile is desirable, where practicable. Lists of additional suitable salts can be found, e.g., in "*Remington's Pharmaceutical Sciences*", 20th ed., Mack Publishing Company, Easton, Pa., (1985); and in "*Handbook of Pharmaceutical Salts: Properties, Selection, and Use*" by Stahl and Wermuth (Wiley-VCH, Weinheim, Germany, 2002).

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine and chlorine, such as $^{2}H$ (deuterium, D), $^{3}H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$, $^{125}I$, respectively.

In another aspect, the compounds of the invention include isotopically enriched compounds as defined herein, for example those into which radioactive isotopes, such as $^{3}H$, $^{14}C$ and $^{18}F$, or those into which non-radioactive isotopes, such as $^{2}H$ and $^{13}C$ are present. Such isotopically enriched compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$-enriched compound may be particularly desirable for PET or SPECT studies. Isotopically-enriched compounds of Formula (I) or (II) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (I) or (II). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, $d_6$-acetone, DMSO-$d_6$.

In another aspect, provided herein are intermediates for preparing the compounds represented by Formula (I) or (II).

In another aspect, provided herein are methods for preparation, separation and purification of the compounds represented by Formula (I) or (II).

In another aspect, provided herein is a pharmaceutical composition comprising the compound disclosed herein. In one embodiment, the pharmaceutical composition further comprises a pharmaceutically acceptable carrier, excipient, adjuvant, vehicle or a combination thereof. In another embodiment, the pharmaceutical composition is a liquid, solid, semi-solid, gel or an aerosol form.

Composition, Formulation and Administration of Compounds of the Invention

Provided herein is a pharmaceutical composition comprising the compound of Formula (I) or (II), or an individual isomer, racemic or non-racemic mixture of isomers or a pharmaceutically acceptable salt or solvate thereof, in admixture with at least one pharmaceutically acceptable carrier, adjuvant or vehicle, and optionally other therapeutic and/or prophylactic ingredients.

Appropriate carriers, adjuvants and vehicles are well known to those of skill in the art and described in, for example, Ansel et al., *Ansel's Pharmaceutical Dosage Forms and Drug Delivery Systems,* 2004, Lippincott, Williams & Wilkins, Philadelphia; Gennaro et al., *Remington: The Science and Practice of Pharmacy,* 2000, Lippincott, Williams & Wilkins, Philadelphia; and Rowe et al., *Handbook of Pharmaceutical Excipients,* 2005, Pharmaceutical Press, Chicago.

It will also be appreciated that certain compounds disclosed herein can exist in free form for treatment, or where appropriate, as a pharmaceutically acceptable derivative thereof. Some non-limiting examples of pharmaceutically acceptable derivative include pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

The pharmaceutical compositions disclosed herein may be prepared and packaged in bulk form wherein a safe and effective amount of the compound disclosed herein can be extracted and then given to the patient such as with powders or syrups. Alternatively, the pharmaceutical compositions disclosed herein may be prepared and packaged in unit dosage form wherein each physically discrete unit contains the compound disclosed herein. When prepared in unit dosage form, the pharmaceutical compositions of the invention typically may contain, for example, from 0.5 mg to 1 g, or from 1 mg to 700 mg, or from 5 mg to 100 mg of the compound disclosed herein.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound disclosed herein when administered to a patient and would result in pharmaceutically unacceptable compositions are avoided. In addition, each excipient must be pharmaceutically-acceptable, e.g., of sufficiently high purity.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds disclosed herein once administered to the patient from one organ, or portion of the body, to another organ, or portion of the body. Certain pharmaceutically acceptable excipients may be chosen for their ability to enhance patient compliance.

Suitable pharmaceutically acceptable excipients comprise the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, humectants, chelating agents, plasticizers, viscosity increasing agents, antioxidants, preservatives, stabilizers, surfactants and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

The pharmaceutical compositions disclosed herein are prepared using techniques and methods known to those skilled in the art. Some of the methods commonly used in the art are described in Remington's Pharmaceutical Sciences (Mack Publishing Company).

Accordingly, in another aspect the invention is directed to process for the preparation of a pharmaceutical composition comprising the compound disclosed herein and a pharmaceutically acceptable excipient, carrier, adjuvant, vehicle or a combination thereof, which comprises mixing the ingredients. A pharmaceutical composition comprising the compound disclosed herein may be prepared by, for example, admixture at ambient temperature and atmospheric pressure.

The compounds disclosed herein will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets and cachets; (2) parenteral administration such as sterile solutions, suspensions and powders for reconstitution; (3) transdermal administration such as transdermal patches; (4) rectal administration such as suppositories; (5) inhalation such as aerosols, solutions and dry powders; and (6) topical administration such as creams, ointments, lotions, solutions, pastes, sprays, foams and gels.

In one embodiment, the compounds disclosed herein will be formulated for oral administration. In another embodiment, the compounds disclosed herein will be formulated for inhaled administration. In a further embodiment, the compounds disclosed herein will be formulated for intranasal administration. In another embodiment, the compounds disclosed herein will be formulated for transdermal administration. In a further embodiment, the compounds disclosed herein will be formulated for topical administration.

The pharmaceutical compositions provided herein can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein can be provided as soft or hard capsules, which can be made from gelatin, methylcellulose, starch or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol or a similar polyol. The soft gelatin shells may contain a preservative to prevent the growth of microorganisms. Suitable preservatives are those as described herein, including methyl- and propyl-parabens, and sorbic acid. The liquid, semisolid and solid dosage forms provided herein may be encapsulated in a capsule. Suitable liquid and semisolid dosage forms include solutions and suspensions in propylene carbonate, vegetable oils or triglycerides. Capsules containing such solutions can be prepared as described in U.S. Pat. Nos. 4,328,245; 4,409,239 and 4,410,545. The capsules may also be coated as known by those of skill in the art in order to modify or sustain dissolution of the active ingredient.

The pharmaceutical compositions provided herein can be provided in liquid and semisolid dosage forms, including emulsions, solutions, suspensions, elixirs and syrups. An emulsion is a two-phase system, in which one liquid is dispersed in the form of small globules throughout another liquid, which can be oil-in-water or water-in-oil. Emulsions may include a pharmaceutically acceptable nonaqueous liquid or solvent, emulsifying agent and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550 and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

Where appropriate, dosage unit formulations for oral administration can be microencapsulated. The composition can also be prepared to prolong or sustain the release as for example by coating or embedding particulate material in polymers, wax or the like.

The pharmaceutical compositions provided herein for oral administration can be also provided in the forms of liposomes, micelles, microspheres or nanosystems. Micellar dosage forms can be prepared as described in U.S. Pat. No. 6,350,458.

The pharmaceutical compositions provided herein can be provided as non-effervescent or effervescent, granules and powders, to be reconstituted into a liquid dosage form. Pharmaceutically acceptable carriers and excipients used in the non-effervescent granules or powders may include diluents, sweeteners and wetting agents. Pharmaceutically acceptable carriers and excipients used in the effervescent granules or powders may include organic acids and a source of carbon dioxide.

Coloring and flavoring agents can be used in all of the above dosage forms.

The compounds disclosed herein may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds disclosed herein may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The pharmaceutical compositions provided herein can be formulated as immediate or modified release dosage forms, including delayed-, sustained-, pulsed-, controlled-, targeted-, and programmed-release forms.

The pharmaceutical compositions provided herein can be co-formulated with other active ingredients which do not impair the desired therapeutic action, or with substances that supplement the desired action.

The pharmaceutical compositions provided herein can be administered parenterally by injection, infusion or implantation, for local or systemic administration. Parenteral administration, as used herein, include intravenous, intraarterial, intraperitoneal, intrathecal, intraventricular, intraurethral, intrasternal, intracranial, intramuscular, intrasynovial and subcutaneous administration.

The pharmaceutical compositions provided herein can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, antifreezing agent, cryoprotectants, thickening agents, pH adjusting agents and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein can be formulated for single or multiple dosage administration. The single dosage formulations are packaged in an ampoule, a vial or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In another aspect, the pharmaceutical compositions disclosed herein can be formulated in any dosage forms that are adapted for administration to a patient by inhalation, for example as a dry powder, an aerosol, a suspension or a solution composition. In one embodiment, the pharmaceutical compositions disclosed herein can be formulated in a dosage form adapted for administration to a patient by inhalation as a dry powder. In a further embodiment, the pharmaceutical compositions disclosed herein can be formulated in a dosage form adapted for administration to a patient by inhalation via a nebulizer. Dry powder compositions for delivery to the lung by inhalation typically comprise the compounds disclosed herein as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

Aerosols may be formed by suspending or dissolving the compound disclosed herein in a liquified propellant. Suitable propellants include halocarbons, hydrocarbons and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutene and pentane. Aerosols comprising the compound disclosed herein will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilizing agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound disclosed herein may be employed with either a paraffinic or a water-miscible ointment base. Alternatively, the compound disclosed herein may be formulated in a cream with an oil-in-water cream base or a water-in-oil base.

Uses of the Compounds and Compositions of the Invention

The compounds and pharmaceutical compositions disclosed herein can be used in the manufacture of a medicament for preventing, treating or lessening the severity of a central nervous system dysfunction, as well as for inhibiting serotonin reuptake and/or acting as $5\text{-HT}_{1A}$ receptor agonists.

Specifically, amount of the compounds used in the compositions disclosed herein is efficient to inhibit serotonin reuptake detectably and selectively, and has agonistic action on $5\text{-HT}_{1A}$ receptor. The compounds disclosed herein may be the agents used for treatment of the human central nervous system (CNS) dysfunction such as depression, anxiety.

The compounds disclosed herein may be used for, but not limited to, preventing, treating or lessening the severity of central nervous system dysfunction by administering an effective amount of the compounds or compositions disclosed herein to a subject. Such central nervous system dysfunctions responsed to 5-HT receptor further include, but are not limited to, depression, anxiety, mania, schizophrenia, bipolar disorder, sleep disorder, obsessive compulsive disorder, panic disorder, post-traumatic stress disorder, movement disorder, sexual dysfunction, musculoskeletal pain disorder, cognitive disorder, memory disorder, Parkinson's disease, Huntington's disease, phobia, substance abuse or addiction, drug addiction withdrawal symptom or premenstrual tension syndrome.

Besides being useful for human treatment, these compounds and compositions are also useful for veterinary treatment of companion animals, exotic animals and mammals of farm animals. In other embodiments, animals include horses, dogs and cats. As used herein, the compounds disclosed herein include the pharmaceutically acceptable derivatives thereof.

Methods of Treatment

In one embodiment, the methods of treatment disclosed herein comprise administering a safe and effective amount of a compound or a pharmaceutically composition disclosed herein to a subject in need thereof. Individual embodiments disclosed herein include methods of treating any one of the above-mentioned disorders by administering a safe and effective amount of a compound disclosed herein or a pharmaceutical composition containing a compound disclosed herein to a subject in need thereof.

In one embodiment, the compounds disclosed herein or pharmaceutically compositions containing the compounds disclosed herein may be administered by any suitable route of administration, including both systemic administration and topical administration. Systemic administration includes oral administration, parenteral administration, transdermal administration and rectal administration. Parenteral administration is typically by injection or infusion, including intravenous, intramuscular, and subcutaneous injection or infusion. Topical administration includes application to the skin as well as intraocular, otic, intravaginal, inhaled and intranasal administration. In one embodiment, the compounds disclosed herein or pharmaceutical compositions containing the compounds disclosed herein may be administered orally. In another embodiment, the compounds disclosed herein or pharmaceutically compositions containing the compounds disclosed herein may be administered by inhalation. In a further embodiment, the compounds disclosed herein or pharmaceutical compositions containing the compounds disclosed herein may be administered intranasally.

In another embodiment, the compounds disclosed herein or pharmaceutically compositions containing the compounds disclosed herein may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound disclosed herein or a pharmaceutical composition containing a compound disclosed herein depend on the pharmacokinetic properties of that compound, such as absorption, distribution, and half-life, which can be determined by the skilled artisan. In addition, suitable dosing regimens, including the duration such regimens are administered, for a compound disclosed herein or a pharmaceutical composition containing a compound disclosed herein depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compound of the present invention may be administered either simultaneously with, or before or after, one or more other therapeutic agent. The compound of the present invention may be administered separately, by the same or different route of administration, or together in the same pharmaceutical composition as the other agents.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys, or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution.

In one embodiment, the therapeutically effective dose is from about 0.1 mg to about 2,000 mg per day of a compound provided herein. The pharmaceutical compositions therefore should provide a dosage of from about 0.1 mg to about 2000 mg of the compound. In certain embodiments, pharmaceutical dosage unit forms are prepared to provide from about 1 mg to about 2000 mg, from about 10 mg to about 1000 mg, from about 20 mg to about 500 mg or from about 25 mg to about 250 mg of the essential active ingredient or a combination of essential ingredients per dosage unit form. In certain embodiments, the pharmaceutical dosage unit forms are prepared to provide about 10 mg, 20 mg, 25 mg, 50 mg, 100 mg, 250 mg, 500 mg, 1000 mg or 2000 mg of the essential active ingredient.

Additionally, the compounds disclosed herein may be administered as prodrugs. As used herein, a "prodrug" of a compound disclosed herein is a functional derivative of the compound which, upon administration to a patient, eventually liberates the compound disclosed herein in vivo. Administration of a compound disclosed herein as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

General Synthetic Procedures

In order to describe the invention, the following examples are set forth. It is to be understood that the invention is not limited to these embodiments, but only provides the methods to practice the invention.

Generally, the compounds in this invention may be prepared by methods described herein, wherein the substituents are as defined for Formula (I) or Formula (II), except where further noted. The following non-limiting schemes and examples are presented to further exemplify the invention.

Persons skilled in the art will recognize that the chemical reactions described herein may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Tianjin Fucheng Reagent Chemical Factory, Wuhan Xinhuayuan Technology Development Co. Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexanes, DMAC and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column Silica gel (300-400 mesh) was purchased from Qingdao Ocean Chemical Factory.

$^1H$ NMR spectra were recorded with a Bruker 400 MHz or 600 MHz spectrometer at ambient temperature. $^1H$ NMR spectra were obtained by using $CDCl_3$, DMSO-$d_6$, $CD_3OD$ or acetone-$d_6$ solutions (reported in ppm), with TMS (0 ppm) or chloroform (7.26 ppm) as the reference standard. When peak multiplicities were reported, the following abbreviations were used: s (singlet), d (doublet), t (triplet), m (multiplet), br (broadened), dd (doublet of doublets), dt (doublet of triplets). Coupling constants, when given, were reported in Hertz (Hz).

Low-resolution mass spectral (MS) data were generally determined on an Agilent 6120 quadrupole HPLC-MS (column: Zorbax SB-C18, 2.1×30 mm, 3.5 micron, 6 minutes run, and 0.6 mL/min flow rate). The mobile phase was 5-95% (0.1% formic acid in $CH_3CN$) in (0.1% formic acid in $H_2O$), and the generated chromatograms were monitored at 210/254 nm by UV detector with electrospray ionization (ESI).

Puritiy of compounds was assessed by Agilent 1260 pre-HPLC or Calesep pump 250 pre-HPLC (column: NOVASEP 50/80 mm DAC) at 210/254 nm by UV detector.

The following abbreviations are used throughout the specification:

AcOH, HOAc, $CH_3COOH$ acetic acid
BOC, Boc tert-butoxycarbonyl
n-BuOH n-butanol
Cbz-Cl benzyl chloroformate
$CH_2Cl_2$, DCM dichloromethane
$CDCl_3$ chloroform-d
DIEA, DIPEA, i-$Pr_2$NEt diisopropylethylamin
DMF N,N-dimethylformamide
THF tetrahydrofuran
DMAP 4-dimethylaminopyridine
DMSO dimethyl sulfoxide
EDC, EDCI 1-(3-dimethylaminopropyl)-3-ethylcarbodiimide hydrochloride
EDTA ethylenediaminetetraacetic acid
$Et_3N$, TEA triethylamine
EtOAc, EA ethyl acetate
g gram
h hour
HCl hydrochloric acid
MeCN, $CH_3CN$ acetonitrile
mL, ml milliliter
Pd/C palladium on activated carbon
$Pd(OH)_2$ palladium hydroxide
PE petroleum ether (60-90° C.)
RT, rt, r.t. room temperature
Rt retention time
TFA trifluoroacetic acid The following synthesis scheme describes the preparation of the compounds disclosed herein. Unless otherwise indicated, each $R^2$, $R^8$, $R^x$, $X^1$, $X^2$, $X^3$, n and p have the definitions as described in the invention, Y is CH, N or O, f is 1 or 2, and g is 0 or 1.

Scheme 1

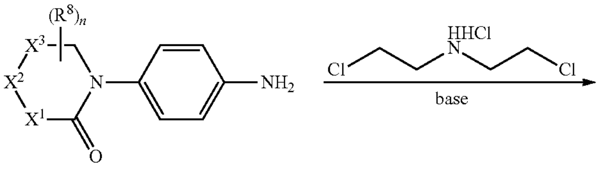

(1)

-continued

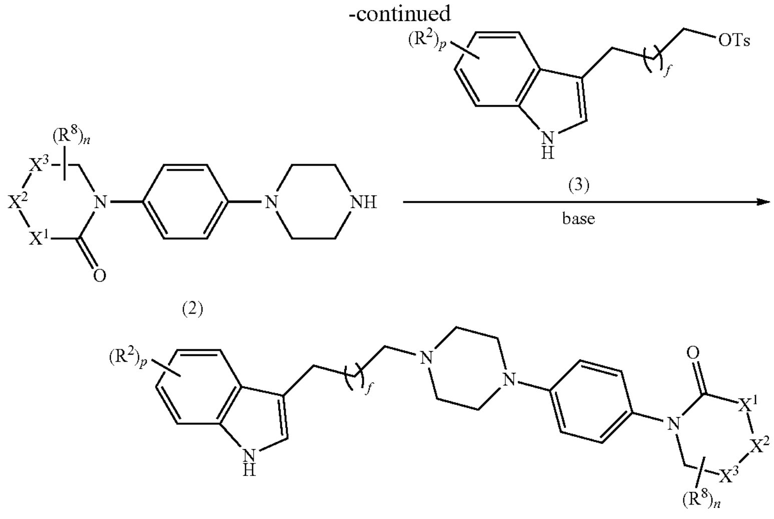

(2) (3) (4)

The compounds disclosed herein can be prepared by the general process illustrated in Scheme 1, and the specific steps are described in the corresponding examples. In Scheme 1, the compound (4) can be prepared by the following process: firstly, cyclization reaction of compound (1) with bis(2-chloroethyl)amine hydrochloride can afford compound (2) in the presence of a base such as potassium carbonate. Compound (2) can then react with compound (1) in the presence of a suitable base such as potassium carbonate, sodium carbonate or triethylamine, and in a suitable solvent such as acetonitrile, THF, ethanol, DMF or DMSO to afford the objective compound (4) by nucleophilic substitution reaction.

Scheme 2

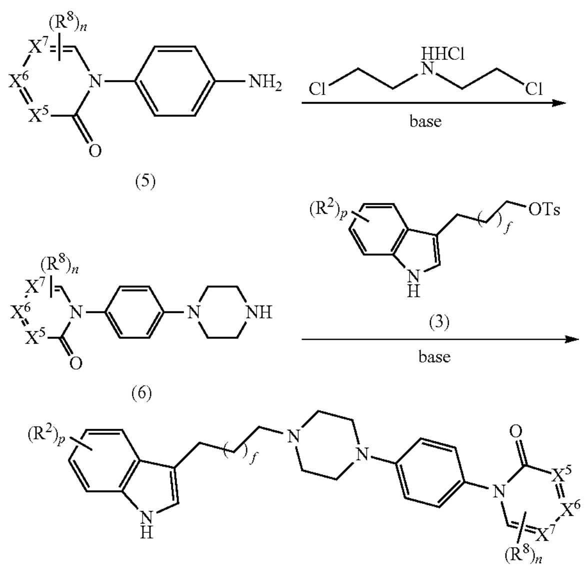

(5) (3) (6) (7)

The compounds disclosed herein can be prepared by the general process illustrated in Scheme 2, wherein each of $X^5$, $X^6$ and $X^7$ is independently CH or N, and the specific steps are described in the corresponding examples. In Scheme 2, the compound (2) can be prepared by the following process: firstly, cyclization reaction of compound (5) with bis(2-chloroethyl)amine hydrochloride can afford compound (6) in the presence of a base such as potassium carbonate. Compound (6) can then react with compound (1) in the presence of a suitable base such as potassium carbonate, sodium carbonate or triethylamine, and in a suitable solvent such as acetonitrile, THF, ethanol, DMF or DMSO to afford the objective compound (7) by nucleophilic substitution reaction.

Scheme 3

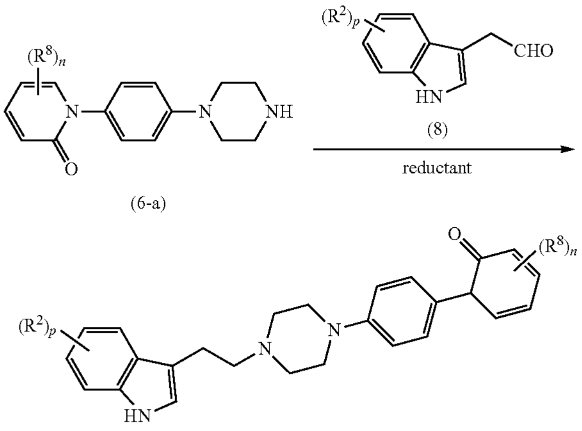

(6-a) (8) (9)

The compounds disclosed herein can be prepared by the general process illustrated in Scheme 3, and the specific steps are described in the corresponding examples. In Scheme 3, the compound (9) can be prepared by the following process: compound can react with compound (8) in the presence of a suitable reductant such as sodium cyanoborohydride, and in a suitable solvent such as methanol to afford the objective compound (9) by reductive amination reaction.

Scheme 4

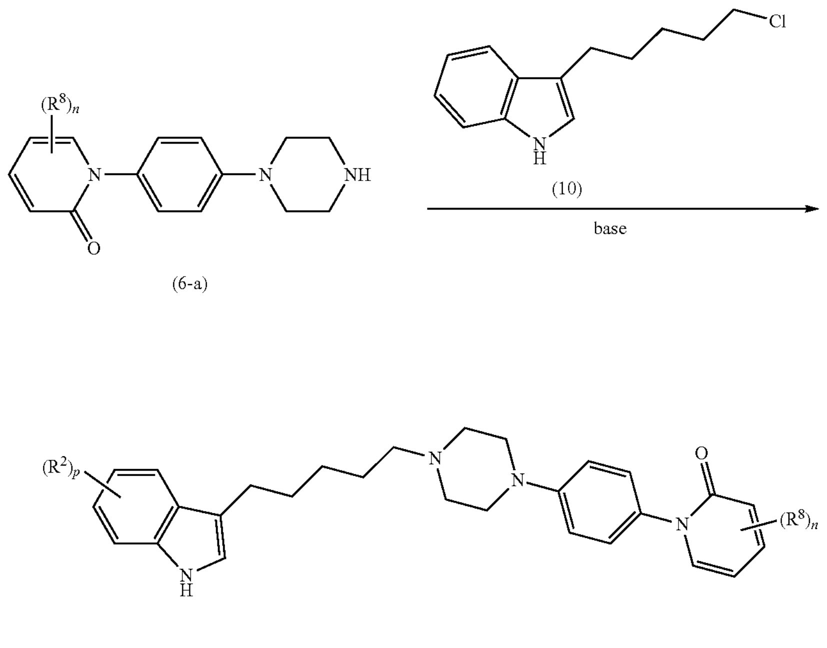

(6-a) (10) (11)

The compounds disclosed herein can be prepared by the general process illustrated in Scheme 4, and the specific steps are described in the corresponding examples. In Scheme 4, the compound (11) can be prepared by the following process: compound (6-a) can react with compound (10) in the presence of a suitable base such as potassium carbonate, sodium carbonate or triethylamine, and in a suitable solvent such as acetonitrile, THF, ethanol, DMF or DMSO to afford the objective compound (11) by nucleophilic substitution reaction.

Scheme 5

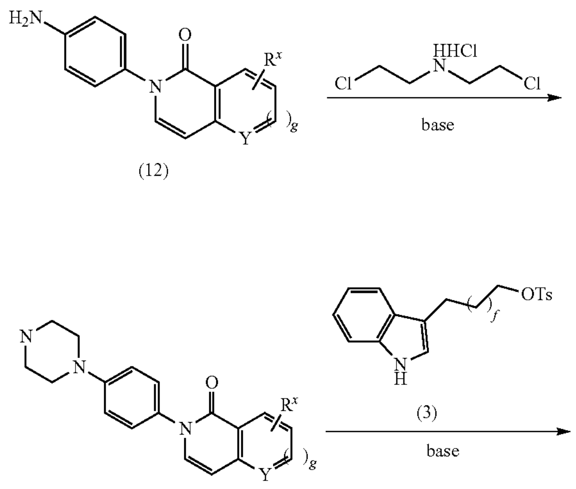

(12) (13) (3)

-continued

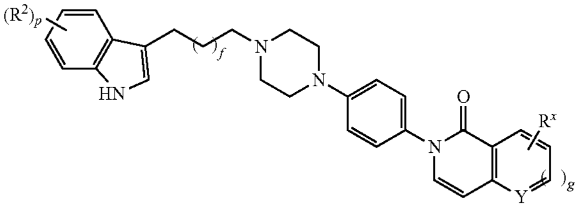

(14)

The compounds disclosed herein can be prepared by the general process illustrated in Scheme 5, and the specific steps are described in the corresponding examples. In Scheme 5, the compound (11) can be prepared by the following process: firstly, cyclization reaction of compound (12) with bis(2-chloroethyl)amine hydrochloride can afford compound (13) in the presence of a base such as potassium carbonate. Compound (13) can then react with compound (1) in the presence of a suitable base such as potassium carbonate, sodium carbonate or triethylamine, and in a suitable solvent such as acetonitrile, THF, ethanol, DMF or DMSO to afford the objective compound (14) by nucleophilic substitution reaction.

Scheme 6

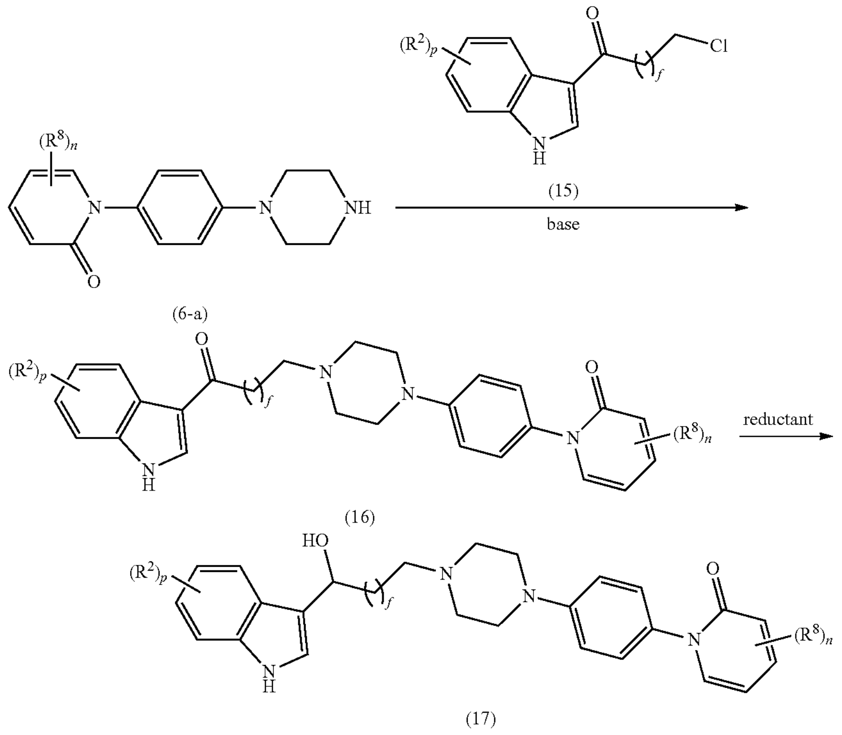

The compounds disclosed herein can be prepared by the general process illustrated in Scheme 6, and the specific steps are described in the corresponding examples. In Scheme 6, the compound (12) can be prepared by the following process: compound (6-a) can react with compound (15) in the presence of a suitable base such as potassium carbonate, sodium carbonate or triethylamine, and in a suitable solvent such as acetonitrile, THF, ethanol, DMF or DMSO to afford compound (16) by nucleophilic substitution reaction. Compound (16) can be then converted to the objective compound (17) in a suitable solvent such as THF by reacting with a suitable reductant such as sodium borohydride.

The compounds, pharmaceutical compositions and applications thereof disclosed herein will be further illustrated in combination with the following examples.

EXAMPLES

Example 1 1-(4-(4-(4-(5-fluoro-1H-indol-3-yl)butyl)piperazin-1-yl)phenyl)piperidin-2-one

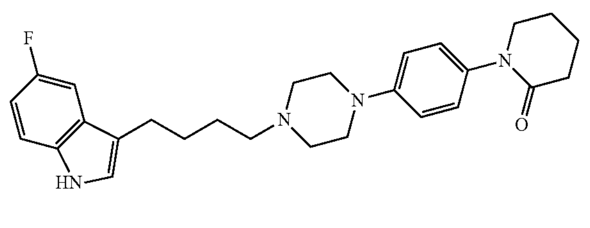 [SMILES: O=C1CCCCN1c1ccc(N2CCN(CCCCc3c[nH]c4ccc(F)cc34)CC2)cc1]

Step 1) 1-(4-(piperazin-1-yl)phenyl)piperidin-2-one

A mixture of 1-(4-aminophenyl)piperidin-2-one (1.90 g, 10.0 mmol), bis(2-chloroethyl)amine hydrochloride (1.96 g, 11.0 mmol) and potassium carbonate (1.5 g, 11.0 mmol) in n-butyl alcohol (20 mL) was stirred at 120° C. for 48 hours under a $N_2$ atmosphere, and then cooled to rt. The resulting mixture was filtered and the filtrate was concentrated in vacuo. The residue was purified by silica gel column chromatography ($CH_2Cl_2/CH_3OH$ (v/v)=15/1) to give the title compound as a white solid (1.55 g, 60.0%). The compound was characterized by the following spectroscopic data: MS (ESI, pos. ion) m/z: 260.2 $[M+H]^+$ and $^1H$ NMR (400 MHz, $CD_3OD$) δ (ppm): 7.12 (d, J=8.9 Hz, 2H), 7.00 (d, J=8.9 Hz, 2H), 3.60 (t, J=4.8 Hz, 2H), 3.23-3.22 (m, 4H), 3.09-3.07 (m, 4H), 2.48 (t, J=6.3 Hz, 2H), 1.93 (t, J=2.8 Hz, 4H).

Step 2) 1-(4-(4-(4-(5-fluoro-1H-indol-3-yl)butyl)piperazin-1-yl)phenyl)piperidin-2-one A mixture of 1-(4-(piperazin-1-yl)phenyl)piperidin-2-one (0.16 g, 0.60 mmol), 4-(5-fluoro-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) was stirred at 80° C. for 20 hours, and then cooled to rt. The resulting mixture was filtered and the filtrate was concentrated in vacuo. The residue was purified by silica gel column chromatography ($CH_2Cl_2/CH_3OH$ (v/v)=20/1) to give the title compound as a white solid (0.21 g, 78.1%). The compound was characterized by the following spectroscopic data: MS (ESI, pos. ion) m/z: 449.2 $[M+H]^+$ and $^1H$ NMR (400 MHz, $CDCl_3$) δ (ppm): 7.97 (s, 1H), 7.25-7.21 (m, 2H), 7.11 (d, J=8.8 Hz, 2H), 7.03 (s, 1H), 6.92-6.90 (m, 3H), 3.58 (t, J=5.0 Hz, 2H), 3.23 (t, J=4.8 Hz, 4H), 2.74 (t, J=7.0 Hz, 2H), 2.63-2.61 (m, 4H), 2.55-2.53 (m, 2H), 2.48 (t, J=7.8 Hz, 2H), 1.91-1.92 (m, 4H), 1.75-1.70 (m, 4H).

Example 2 3-(4-(4-(4-(2-oxopiperidin-1-yl)phenyl)piperazin-1-yl)butyl)-1H-indole-5-carbonitrile

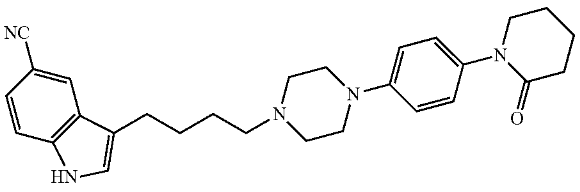 [SMILES: N#Cc1ccc2[nH]cc(CCCCN3CCN(c4ccc(N5CCCCC5=O)cc4)CC3)c2c1]

The title compound was prepared by the procedure described in step 2 of example 1, using 1-(4-(piperazin-1-yl)phenyl)piperidin-2-one (0.16 g, 0.60 mmol), 4-(5-cyano-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.16 g, 60.0%). The compound was characterized by the following spectroscopic data: MS (ESI, pos. ion) m/z: 456.3 $[M+H]^+$ and $^1H$ NMR (400 MHz, $CDCl_3$) δ (ppm): 8.51 (s, 1H), 7.97 (s, 1H), 7.41-7.36 (m, 2H), 7.11 (d, J=8.9 Hz, 2H), 7.05 (s, 1H), 6.90 (d, J=8.9 Hz, 2H), 3.59 (t, J=5.1 Hz, 2H), 3.20 (t, J=4.8 Hz, 4H), 2.78 (t, J=7.2 Hz, 2H), 2.61 (t, J=4.8 Hz, 4H), 2.55-2.53 (m, 2H), 2.46 (t, J=7.6 Hz, 2H), 1.92 (t, J=3.6 Hz, 4H), 1.76-1.63 (m, 4H).

Example 3 1-(4-(4-(3-(5-fluoro-1H-indol-3-yl)propyl)piperazin-1-yl)phenyl)piperidin-2-one

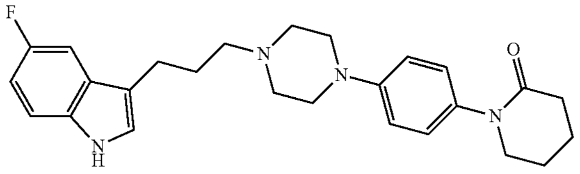 [SMILES: O=C1CCCCN1c1ccc(N2CCN(CCCc3c[nH]c4ccc(F)cc34)CC2)cc1]

The title compound was prepared by the procedure described in step 2 of example 1, using 1-(4-(piperazin-1-yl)phenyl)piperidin-2-one (0.16 g, 0.60 mmol), 3-(5-fluoro-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a yellow solid (0.20 g, 78.0%). The compound was characterized by the following spectroscopic data: MS (ESI, pos. ion) m/z: 435.2 $[M+H]^+$ and $^1H$ NMR (400 MHz, $CDCl_3$) δ (ppm): 8.01 (s, 1H), 7.29 (s, 1H), 7.26 (d, J=3.0 Hz, 1H), 7.14 (d, J=8.8 Hz, 2H), 7.06 (s, 1H), 6.98-6.93 (m, 3H), 3.61 (t, J=4.9 Hz, 2H), 3.25 (t, J=4.8 Hz, 4H), 2.78 (t, J=7.4 Hz, 2H), 2.65 (t, J=4.8 Hz, 4H), 2.58-2.50 (m, 4H), 2.00-1.93 (m, 6H).

Example 4 3-(3-(4-(4-(2-oxopiperidin-1-yl)phenyl)piperazin-1-yl)propyl)-1H-indole-5-carbonitrile

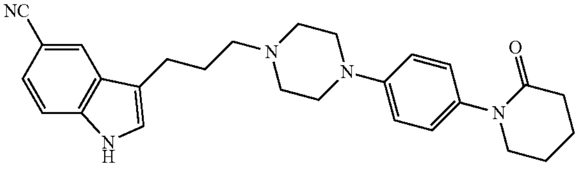 [SMILES: N#Cc1ccc2[nH]cc(CCCN3CCN(c4ccc(N5CCCCC5=O)cc4)CC3)c2c1]

The title compound was prepared by the procedure described in step 2 of example 1, using 1-(4-(piperazin-1-yl)phenyl)piperidin-2-one (0.16 g, 0.60 mmol), 3-(5-cyano-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a yellow solid (0.15 g, 58.0%). The compound was characterized by the following spectroscopic data: MS (ESI, pos. ion) m/z: 442.2 $[M+H]^+$ and $^1H$ NMR (400 MHz, $CDCl_3$) δ (ppm): 8.47 (s, 1H), 7.97 (s, 1H), 7.42-7.35 (m, 2H), 7.11 (d, J=8.9 Hz, 3H), 6.91 (d, J=8.9 Hz, 2H), 3.59 (t, J=4.8 Hz, 2H), 3.23 (t, J=4.8 Hz, 4H), 2.81 (t, J=7.5 Hz, 2H), 2.65 (t, J=4.8 Hz, 4H), 2.54-2.49 (m, 4H), 1.93-1.91 (m, 6H).

Example 5 4-(4-(4-(4-(5-fluoro-1H-indol-3-yl)butyl)piperazin-1-yl)phenyl)morpholin-3-one

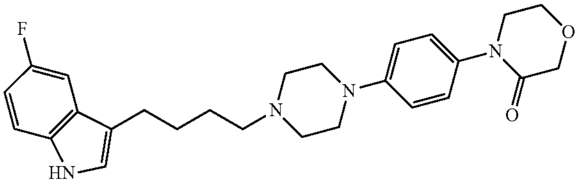 [SMILES: O=C1COCCN1c1ccc(N2CCN(CCCCc3c[nH]c4ccc(F)cc34)CC2)cc1]

Step 1) 4-(4-(piperazin-1-yl)phenyl)morpholin-3-one

The title compound was prepared by the procedure described in step 1 of example 1, using 4-(4-aminophenyl)morpholin-3-one (1.92 g, 10.0 mmol), bis(2-chloroethyl)amine hydrochloride (1.96 g, 11.0 mmol) and potassium carbonate (1.5 g, 11.0 mmol) in n-butyl alcohol (20 mL) to give the crude product, which was purified by silica gel column chromatography ($CH_2Cl_2/CH_3OH$ (v/v)=20/1) to give the title compound as a white solid (0.19 g, 72.5%). The compound was characterized by the following spectroscopic data: MS (ESI, pos. ion) m/z: 262.2 $[M+H]^+$ and $^1H$ NMR (400 MHz, $CD_3OD$) δ (ppm): 7.28-7.21 (m, 2H), 6.96 (d, J=9.0 Hz, 2H), 4.34 (s, 2H), 4.03 (t, J=4.8 Hz, 2H), 3.73 (t, J=5.2 Hz, 2H), 3.26-3.24 (m, 4H), 3.13-3.10 (m, 4H).

Step 2) 4-(4-(4-(4-(5-fluoro-1H-indol-3-yl)butyl)piperazin-1-yl)phenyl)morpholin-3-one The title compound was prepared by the procedure described in step 2 of example 1, using 4-(4-(piperazin-1-yl)phenyl)morpholin-3-one (0.16 g, 0.60 mmol), 4-(5- fluoro-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.19 g, 70.0%). The compound was characterized by the following spectroscopic data: MS (ESI, pos. ion) m/z: 451.3 $[M+H]^+$ and $^1H$ NMR (400 MHz, $CD_3OD$) δ (ppm): 8.00 (s, 1H), 7.24 (d, J=7.1 Hz, 2H), 7.20 (d, J=8.1 Hz, 2H), 7.04 (s, 1H), 6.95 (d, J=7.4 Hz, 3H), 4.35 (s, 2H), 4.03-4.01 (m, 2H), 3.73-3.70 (m, 2H), 3.23-3.21 (m, 4H), 2.76 (t, J=6.5 Hz, 2H), 2.62-2.60 (m, 4H), 2.47 (t, J=7.2 Hz, 2H), 1.74-1.71 (m, 4H).

Example 6 3-(4-(4-(4-(3-oxomorpholino)phenyl)piperazin-1-yl)butyl)-1H-indole-5-carbonitrile

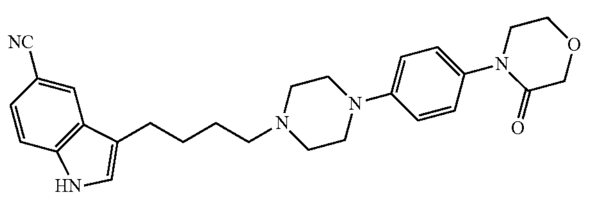 [SMILES: N#Cc1ccc2[nH]cc(CCCCN3CCN(c4ccc(N5CCOCC5=O)cc4)CC3)c2c1]

The title compound was prepared by the procedure described in step 2 of example 1, using 4-(4-(piperazin-1-yl)phenyl)morpholin-3-one (0.16 g, 0.60 mmol), 4-(5-cyano-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.16 g, 58.2%). The compound was characterized by the following spectroscopic data: MS (ESI, pos. ion) m/z: 458.3 $[M+H]^+$ and $^1H$ NMR (400 MHz, $CD_3OD$) δ (ppm): 8.47 (s, 1H), 7.97 (s, 1H), 7.42-7.38 (m, 2H), 7.20 (d, J=8.8 Hz, 2H), 7.10 (s, 1H), 6.94 (d, J=8.9 Hz, 2H), 4.35 (s, 2H), 4.03 (t, J=4.8 Hz, 2H), 3.73 (t, J=5.2 Hz, 2H), 3.24 (t, J=4.8 Hz, 4H), 2.81 (t, J=7.2 Hz, 2H), 2.64 (t, J=4.8 Hz, 4H), 2.48 (t, J=7.5 Hz, 2H), 1.69-1.63 (m, 4H).

Example 7 4-(4-(4-(3-(5-fluoro-1H-indol-3-yl)propyl)piperazin-1-yl)phenyl)morpholin-3-one

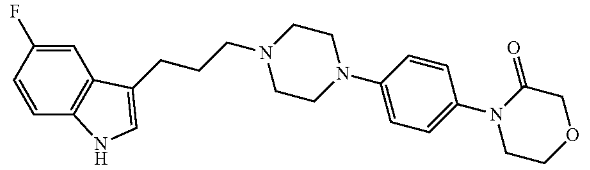 [SMILES: O=C1COCCN1c1ccc(N2CCN(CCCc3c[nH]c4ccc(F)cc34)CC2)cc1]

The title compound was prepared by the procedure described in step 2 of example 1, using 4-(4-(piperazin-1-yl)phenyl)morpholin-3-one (0.16 g, 0.60 mmol), 3-(5-fluoro-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.19 g, 73.0%). The compound was characterized by the following spectroscopic data: MS (ESI, pos. ion) m/z: 437.1 $[M+H]^+$ and $^1H$ NMR (400 MHz, $CD_3OD$) δ (ppm): 8.05 (s, 1H), 7.26 (d, J=4.0 Hz, 1H), 7.21 (d, J=8.9 Hz, 2H), 7.05 (d, J=1.8 Hz, 1H), 6.92-6.97 (m, 3H), 4.35 (s, 2H), 4.03 (t, J=4.8 Hz, 2H), 3.73 (t, J=5.2 Hz, 2H), 3.25 (t, J=4.8 Hz, 4H), 2.78 (t, J=7.4 Hz, 2H), 2.63 (t, J=5.0 Hz, 4H), 2.51 (t, J=7.4 Hz, 2H), 1.99-1.92 (m, 2H).

Example 8 3-(3-(4-(4-(3-oxomorpholino)phenyl)piperazin-1-yl)propyl)-1H-indole-5-carbonitrile

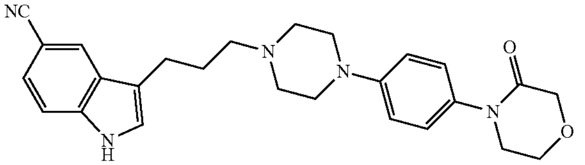 [SMILES: N#Cc1ccc2[nH]cc(CCCN3CCN(c4ccc(N5CCOCC5=O)cc4)CC3)c2c1]

The title compound was prepared by the procedure described in step 2 of example 1, using 4-(4-(piperazin-1-yl)phenyl)morpholin-3-one (0.16 g, 0.60 mmol), 3-(5-cyano-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.15 g, 57.0%). The compound was characterized by the following spectroscopic data: MS (ESI, pos. ion) m/z: 444.3 $[M+H]^+$ and $^1H$ NMR (400 MHz, $CD_3OD$) δ (ppm): 8.33 (s, 1H), 7.98 (s, 1H), 7.43-7.38 (m, 2H), 7.19 (d, J=8.9 Hz, 2H), 7.11 (s, 1H), 6.93 (d, J=9.0 Hz, 2H), 4.33 (s, 2H), 4.01 (t, J=4.9 Hz, 2H), 3.71 (t, J=5.2 Hz, 2H), 3.24 (t, J=4.8 Hz, 4H), 2.81 (t, J=7.4 Hz, 2H), 2.63 (t, J=4.7 Hz, 4H), 2.49 (t, J=7.2 Hz, 2H), 2.04-1.93 (m, 2H).

Example 9 3-(4-(4-(4-(2-oxopyridin-1(2H)-yl)phenyl)piperazin-1-yl)butyl)-1H-indole-5-carbonitrile

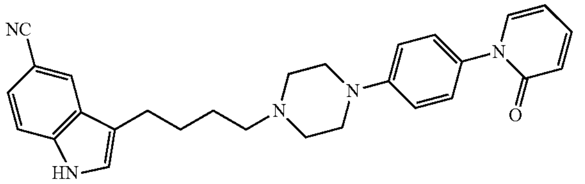 [SMILES: N#Cc1ccc2[nH]cc(CCCCN3CCN(c4ccc(-n5ccccc5=O)cc4)CC3)c2c1]

Step 1) 1-(4-(piperazin-1-yl)phenyl)pyridin-2(1H)-one

The title compound was prepared by the procedure described in step 1 of example 1, using 1-(4-aminophenyl)pyridin-2(1H)-one (1.86 g, 10.0 mmol), bis(2-chloroethyl)amine hydrochloride (1.96 g, 11.0 mmol) and potassium carbonate (1.5 g, 11.0 mmol) in n-butyl alcohol (20 mL) to give the crude product, which was purified by silica gel column chromatography ($CH_2Cl_2/CH_3OH$ (v/v)=20/1) to give the title compound as a white solid (1.40 g, 55.0%). The compound was characterized by the following spectroscopic data: MS (ESI, pos. ion) m/z: 256.2 $[M+H]^+$ and $^1H$ NMR (400 MHz, $CD_3OD$) δ (ppm): 7.64-7.56 (m, 2H), 7.31 (d, J=9.0 Hz, 2H), 7.15 (d, J=9.0 Hz, 2H), 6.62 (d, J=9.0 Hz, 1H), 6.47 (td, J=6.8, 1.2 Hz, 1H), 3.50 (t, J=4.8 Hz, 4H), 3.39 (t, J=4.8 Hz, 4H).

Step 2) 3-(4-(4-(4-(2-oxopyridin-1(2H)-yl)phenyl) piperazin-1-yl)butyl)-1H-indole-5-carbonitrile The title compound was prepared by the procedure described in step 2 of example 1, using 1-(4-(piperazin-1-yl)phenyl)pyridin-2(1H)-one (0.15 g, 0.60 mmol), 4-(5-cyano-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.16 g, 60.0%). The compound was characterized by the following spectroscopic data: MS (ESI, pos. ion) m/z: 452.3 $[M+H]^+$ and $^1H$ NMR (400 MHz, $CDCl_3$) δ (ppm): 11.36 (brs, 1H), 8.07 (s, 1H), 7.57 (dd, J=6.8, 1.6 Hz, 1H), 7.49 (d, J=8.4 Hz, 1H), 7.47-7.44 (m, 1H), 7.39 (dd, J=8.4, 1.2 Hz, 1H), 7.33 (d, J=1.6 Hz, 1H), 7.19 (d, J=8.8 Hz, 2H), 6.99 (d, J=8.8 Hz, 2H), 6.43 (d, J=8.8 Hz, 1H), 6.26 (td, J=6.8, 1.2 Hz, 1H), 3.17-3.16 (m, 4H), 2.74 (t, J=7.2 Hz, 2H), 2.50-2.49 (m, 4H), 2.38-2.34 (m, 2H), 1.69-1.66 (m, 2H), 1.54-1.51 (m, 2H).

Example 10 1-(4-(4-(4-(5-fluoro-1H-indol-3-yl) butyl)piperazin-1-yl)phenyl)pyridin-2(1H)-one

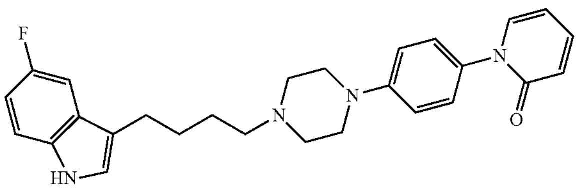 [SMILES: O=c1ccccn1-c1ccc(N2CCN(CCCCc3c[nH]c4ccc(F)cc34)CC2)cc1]

The title compound was prepared by the procedure described in step 2 of example 1, using 1-(4-(piperazin-1-yl)phenyl)pyridin-2(1H)-one (0.15 g, 0.60 mmol), 4-(5-fluoro-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.21 g, 80.0%). The compound was characterized by the following spectroscopic data: MS (ESI, pos. ion) m/z: 445.3 $[M+H]^+$ and $^1H$ NMR (400 MHz, $CDCl_3$) δ (ppm): 7.98 (s, 1H), 7.39-7.35 (m, 1H), 7.34 (dd, J=6.8, 1.6 Hz, 1H), 7.27-7.23 (m, 4H), 7.03 (d, J=1.6 Hz, 1H), 6.98-6.95 (m, 2H), 6.93-6.90 (m, 1H), 6.64 (d, J=9.2 Hz, 1H), 6.22-6.19 (m, 1H), 3.25 (t, J=4.8 Hz, 4H), 2.75 (t, J=7.0 Hz, 2H), 2.60 (t, J=4.8 Hz, 4H), 2.45 (t, J=7.7 Hz, 2H), 1.76-1.67 (m, 2H), 1.54-1.51 (m, 2H).

Example 11 3-(3-(4-(4-(2-oxopyridin-1(2H)-yl)phenyl)piperazin-1-yl)propyl)-1H-indole-5-carbonitrile

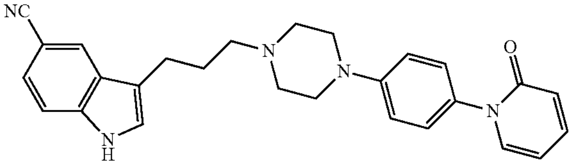 [SMILES: N#Cc1ccc2[nH]cc(CCCN3CCN(c4ccc(-n5ccccc5=O)cc4)CC3)c2c1]

The title compound was prepared by the procedure described in step 2 of example 1, using 1-(4-(piperazin-1-yl)phenyl)pyridin-2(1H)-one (0.15 g, 0.60 mmol), 3-(5-cyano-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.15 g, 57.1%). The compound was characterized by the following spectroscopic data: MS (ESI, pos. ion) m/z: 438.2 $[M+H]^+$ and $^1H$ NMR (400 MHz, $CDCl_3$) δ (ppm): 8.56 (s, 1H), 7.98 (s, 1H), 7.41-7.36 (m, 3H), 7.32 (d, J=6.8 Hz, 1H), 7.24 (d, J=9.0 Hz, 2H), 7.08 (s, 1H), 6.96 (d, J=8.9 Hz, 2H), 6.65 (d, J=9.1 Hz, 1H), 6.22 (t, J=5.9 Hz, 1H), 3.25 (t, J=4.8 Hz, 4H), 2.81 (t, J=7.4 Hz, 2H), 2.61 (t, J=4.8 Hz, 4H), 2.48 (t, J=7.4 Hz, 2H), 1.93 (t, J=7.5 Hz, 2H).

Example 12 1-(4-(4-(3-(5-fluoro-1H-indol-3-yl) propyl)piperazin-1-yl)phenyl)pyridin-2(1H)-one

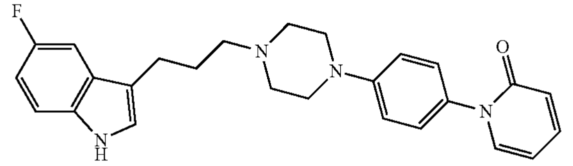 [SMILES: O=c1ccccn1-c1ccc(N2CCN(CCCc3c[nH]c4ccc(F)cc34)CC2)cc1]

The title compound was prepared by the procedure described in step 2 of example 1, using 1-(4-(piperazin-1-yl)phenyl)pyridin-2(1H)-one (0.15 g, 0.60 mmol), 3-(5-fluoro-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.19 g, 73.6%). The compound was characterized by the following spectroscopic data: MS (ESI, pos. ion) m/z: 431.2 $[M+H]^+$ and $^1H$ NMR (400 MHz, $CDCl_3$) δ (ppm): 8.00 (s, 1H), 7.41-7.37 (m, 1H), 7.34 (d, J=6.8 Hz, 1H), 7.28-7.25 (m, 4H), 7.07 (s, 1H), 7.02-6.98 (m, 2H), 6.96-6.93 (m, 1H), 6.67 (d, J=9.5 Hz, 1H), 6.24-6.21 (m, 1H), 3.29 (t, J=4.8 Hz, 4H), 2.79 (t, J=7.6 Hz, 2H), 2.64 (t, J=4.8 Hz, 4H), 2.51 (t, J=7.2 Hz, 2H), 2.00-1.92 (m, 2H).

Example 13 3-(2-(4-(4-(2-oxopyridin-1(2H)-yl)phenyl)piperazin-1-yl)ethyl)-1H-indole-5-carbonitrile

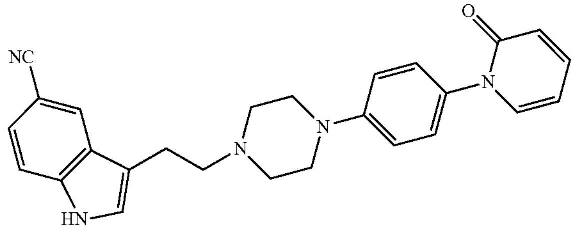 [SMILES: N#Cc1ccc2[nH]cc(CCN3CCN(c4ccc(-n5ccccc5=O)cc4)CC3)c2c1]

To a solution of 3-(2-oxoethyl)-1H-indole-5-carbonitrile (0.11 g, 0.60 mmol) in a mixture of methanol (15 mL) and tetrahydrofuran (15 mL) were added 1-(4-(piperazin-1-yl) phenyl) pyridin-2(1H)-one (0.15 g, 0.60 mmol), sodium cyanoborohydride (0.11 g, 1.8 mmol) and acetic acid (0.1 mL) in turns at 0° C. The reaction mixture was stirred at room temperature for 10 hours, and then concentrated in vacuo. The residue was washed with water, dried, and purified by silica gel column chromatography ($CH_2Cl_2$/$CH_3OH$ (v/v)=20/1) to give the title compound as a pale yellow solid (0.18 g, 71.0%). The compound was characterized by the following spectroscopic data: MS (ESI, pos. ion) m/z: 424.3 $[M+H]^+$ and $^1H$ NMR (400 MHz, DMSO-$d_6$) δ (ppm): 11.65 (s, 1H), 10.04 (brs, 1H), 8.24 (s, 1H), 7.56 (d, J=8.4 Hz, 1H), 7.51-7.45 (m, 3H), 7.25 (d, J=8.8 Hz, 2H), 7.12 (d, J=8.8 Hz, 2H), 6.05 (dd, J=7.6, 2.8 Hz, 1H), 5.87 (d, J=2.8 Hz, 1H), 3.98-3.95 (m, 2H), 3.78-3.75 (m, 2H), 3.49-3.46 (m, 2H), 3.31-3.17 (m, 4H), 3.11-3.06 (m, 2H).

Example 14 3-(5-(4-(4-(2-oxopyridin-1(2H)-yl)phenyl)piperazin-1-yl)pentyl)-1H-indole-5-carbonitrile

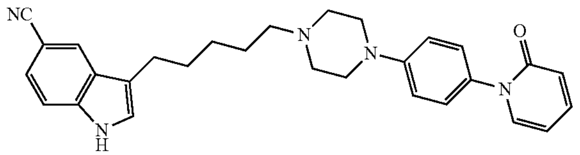 [SMILES: N#Cc1ccc2[nH]cc(CCCCCN3CCN(c4ccc(-n5ccccc5=O)cc4)CC3)c2c1]

The title compound was prepared by the procedure described in step 2 of example 1, using 1-(4-(piperazin-1-yl)phenyl)pyridin-2(1H)-one (0.15 g, 0.60 mmol), 3-(5-chloropentyl)-1H-indole-5-carbonitrile (0.15 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.22 g, 78.0%). The compound was characterized by the following spectroscopic data: MS (ESI, pos. ion) m/z: 466.3 $[M+H]^+$ and $^1H$ NMR (400 MHz, DMSO-$d_6$) δ (ppm): 9.29 (s, 1H), 7.91 (s, 1H), 7.42-7.38 (m, 1H), 7.34-7.29 (m, 3H), 7.24-7.23 (m, 1H), 7.21-7.20 (m, 1H), 6.99 (d, J=2.1 Hz, 1H), 6.93 (m, 1H), 6.91 (m, 1H), 6.65 (d, J=9.5 Hz, 1H), 6.24 (td, J=6.8, 1.2 Hz, 1H), 3.24-3.21 (m, 4H), 2.73 (t, J=7.5 Hz, 2H), 2.62-2.60 (m, 4H), 2.44-2.40 (m, 2H), 1.75-1.67 (m, 2H), 1.65-1.56 (m, 2H), 1.45-1.37 (m, 2H).

Example 15 3-(1-hydroxy-4-(4-(4-(2-oxopyridin-1(2H)-yl)phenyl)piperazin-1-yl)butyl)-1H-indole-5-carbonitrile

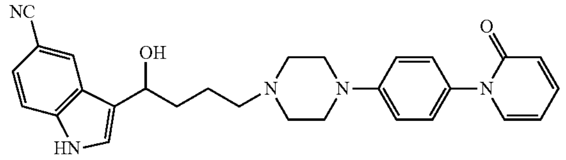 [SMILES: N#Cc1ccc2[nH]cc(C(O)CCCN3CCN(c4ccc(-n5ccccc5=O)cc4)CC3)c2c1]

Step 1) 3-(4-(4-(4-(2-oxopyridin-1(2H)-yl)phenyl)piperazin-1-yl)butanoyl)-1H-indole-5-carbonitrile

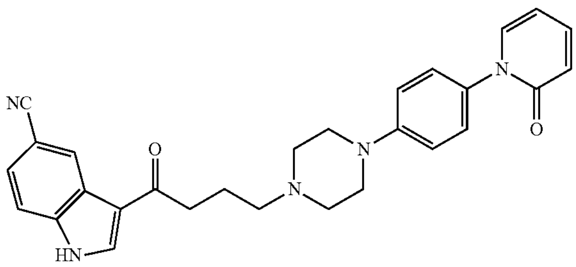 [SMILES: N#Cc1ccc2[nH]cc(C(=O)CCCN3CCN(c4ccc(-n5ccccc5=O)cc4)CC3)c2c1]

The title compound was prepared by the procedure described in step 2 of example 1, using 1-(4-(piperazin-1-yl)phenyl)pyridin-2(1H)-one (0.15 g, 0.60 mmol), 3-(4-chlorobutanoyl)-1H-indole-5-carbonitrile (0.15 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=10/1) to give the title compound as a white solid (0.20 g, 71.0%). The compound was characterized by the following spectroscopic data: MS (ESI, pos. ion) m/z: 466.3 $[M+H]^+$ and $^1H$ NMR (400 MHz, DMSO-$d_6$) δ (ppm): 8.56 (s, 1H), 7.98 (s, 1H), 7.41-7.36 (m, 3H), 7.32 (d, J=6.8 Hz, 1H), 7.24 (d, J=9.0 Hz, 2H), 7.08 (s, 1H), 6.96 (d, J=8.9 Hz, 2H), 6.65 (d, J=9.1 Hz, 1H), 6.22 (t, J=5.9 Hz, 1H), 3.25 (t, J=4.8 Hz, 4H), 2.75 (t, J=7.0 Hz, 2H), 2.60 (t, J=4.8 Hz, 4H), 2.45 (t, J=7.7 Hz, 2H), 1.76-1.67 (m, 2H).

Step 2) 3-(1-hydroxy-4-(4-(4-(2-oxopyridin-1(2H)-yl)phenyl)piperazin-1-yl)butyl)-1H-indole-5-carbonitrile To a solution of 3-(4-(4-(4-(2-oxopyridin-1(2H)-yl)phenyl)piperazin-1-yl)butanoyl)-1H-indole-5-carbonitrile (0.51 g, 1.1 mmol) in tetrahydrofuran (10 mL) was added sodium borohydride (0.02 g, 0.6 mmol) at 0° C. The reaction mixture was then heated to 70° C. and stirred for 3 hours. The resulting mixture was concentrated in vacuo. The residue was washed with water, dried, and purified by silica gel column chromatography ($CH_2Cl_2$/$CH_3OH$ (v/v)=20/1) to give the title compound as a yellow solid (0.18 g, 35.0%). The compound was characterized by the following spectroscopic data: MS (ESI, pos. ion) m/z: 468.3 $[M+H]^+$ and $^1H$ NMR (400 MHz, DMSO-$d_6$) δ (ppm): 8.59 (s, 1H), 7.97 (s, 1H), 7.41-7.36 (m, 3H), 7.32 (d, J=6.8 Hz, 1H), 7.24 (d, J=9.0 Hz, 2H), 7.08 (s, 1H), 6.96 (d, J=8.9 Hz, 2H), 6.65 (d, J=9.1 Hz, 1H), 6.22 (t, J=5.9 Hz, 1H), 4.33-4.21 (m, 1H), 3.27 (t, J=4.8 Hz, 4H), 2.77 (t, J=7.0 Hz, 2H), 2.57 (t, J=4.8 Hz, 4H), 2.45 (t, J=7.7 Hz, 2H), 1.77-1.67 (m, 2H).

Example 16 3-(1-hydroxy-3-(4-(4-(2-oxopyridin-1(2H)-yl)phenyl)piperazin-1-yl)propyl)-1H-indole-5-carbonitrile

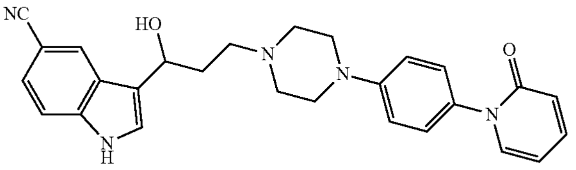 [SMILES: N#Cc1ccc2[nH]cc(C(O)CCN3CCN(c4ccc(-n5ccccc5=O)cc4)CC3)c2c1]

Step 1) 3-(3-(4-(4-(2-oxopyridin-1(2H)-yl)phenyl)piperazin-1-yl)propanoyl)-1H-indole-5-carbonitrile

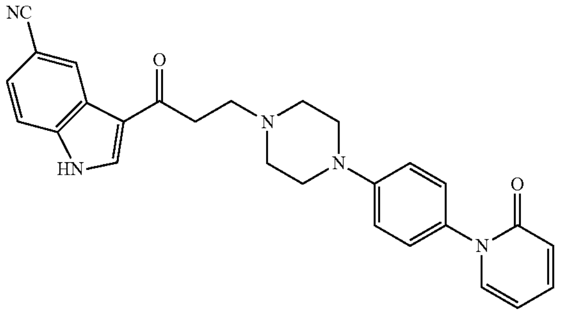 [SMILES: N#Cc1ccc2[nH]cc(C(=O)CCN3CCN(c4ccc(-n5ccccc5=O)cc4)CC3)c2c1]

The title compound was prepared by the procedure described in step 2 of example 1, using 1-(4-(piperazin-1-yl)phenyl)pyridin-2(1H)-one (0.45 g, 1.80 mmol), 3-(3-chloropropanoyl)-1H-indole-5-carbonitrile (0.42 g, 1.80 mmol), potassium carbonate (0.36 g, 2.70 mmol) and potassium iodide (0.06 g, 0.36 mmol) in acetonitrile (20 mL) to give the crude product, which was purified by silica gel column chromatography ($CH_2Cl_2/CH_3OH$ (v/v)=20/1) to give the title compound as a white solid (0.63 g, 78.0%). The compound was characterized by the following spectroscopic data: MS (ESI, pos. ion) m/z: 452.3 $[M+H]^+$.

Step 2) 3-(1-hydroxy-3-(4-(4-(2-oxopyridin-1(2H)-yl)phenyl)piperazin-1-yl)propyl)-1H-indole-5-carbonitrile To a solution of 3-(3-(4-(4-(2-oxopyridin-1(2H)-yl)phenyl)piperazin-1-yl)propanoyl)-1H-indole-5-carbonitrile (0.50 g, 1.1 mmol) in tetrahydrofuran (10 mL) was added sodium borohydride (0.02 g, 0.6 mmol) at 0° C. The reaction mixture was then heated to 70° C. and stirred for 3 hours. The resulting mixture was concentrated in vacuo. The residue was washed with water, dried, and purified by silica gel column chromatography ($CH_2Cl_2/CH_3OH$ (v/v)=20/1) to give the title compound as a yellow solid (0.15 g, 30.0%). The compound was characterized by the following spectroscopic data: MS (ESI, pos. ion) m/z: 454.3 $[M+H]^+$.

Example 17 3-(4-(4-(4-(4-methyl-2-oxopyridin-1(2H)-yl)phenyl)piperazin-1-yl)butyl)-1H-indole-5-carbonitrile

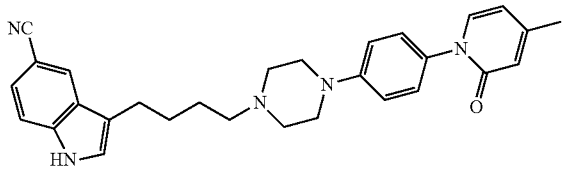 [SMILES: Cc1ccn(-c2ccc(N3CCN(CCCCc4c[nH]c5ccc(C#N)cc45)CC3)cc2)c(=O)c1]

Step 1) 4-methyl-1-(4-(piperazin-1-yl)phenyl)pyridin-2(1H)-one

The title compound was prepared by the procedure described in step 1 of example 1, using 1-(4-aminophenyl)-4-methylpyridin-2(1H)-one (2.00 g, 10.0 mmol), bis(2-chloroethyl)amine hydrochloride (1.96 g, 11.0 mmol) and potassium carbonate (1.5 g, 11.0 mmol) in n-butyl alcohol (20 mL) to give the crude product, which was purified by silica gel column chromatography ($CH_2Cl_2/CH_3OH$ (v/v)=20/1) to give the title compound as a white solid (1.78 g, 66.0%). The compound was characterized by the following spectroscopic data: MS (ESI, pos. ion) m/z: 270.2 $[M+H]^+$ and $^1H$ NMR (400 MHz, $CD_3OD$) δ (ppm): 7.89 (s, 1H), 7.73 (d, J=6.9 Hz, 1H), 7.66 (d, J=8.9 Hz, 2H), 7.45 (d, J=8.9 Hz, 2H), 6.70 (dd, J=7.0, 1.7 Hz, 1H), 3.90-3.87 (m, 4H), 3.75-3.73 (m, 4H), 2.68 (s, 3H).

Step 2) 3-(4-(4-(4-(4-methyl-2-oxopyridin-1(2H)-yl)phenyl)piperazin-1-yl)butyl)-1H-indole-5-carbonitrile The title compound was prepared by the procedure described in step 2 of example 1, using 4-methyl-1-(4-(piperazin-1-yl)phenyl)pyridin-2(1H)-one (0.16 g, 0.60 mmol), 4-(5-cyano-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.19 g, 67.8%). The compound was characterized by the following spectroscopic data: MS (ESI, pos. ion) m/z: 466.2 $[M+H]^+$ and $^1H$ NMR (400 MHz, $CDCl_3$) δ (ppm): 8.74 (s, 1H), 7.93 (s, 1H), 7.40-7.35 (m, 2H), 7.23 (s, 1H), 7.21 (t, J=3.5 Hz, 2H), 7.05 (d, J=2.0 Hz, 1H), 6.94 (d, J=9.0 Hz, 2H), 6.45 (s, 1H), 6.07 (dd, J=7.0, 1.8 Hz, 1H), 3.27 (t, J=4.8 Hz, 4H), 2.78 (t, J=7.0 Hz, 2H), 2.65 (t, J=4.8 Hz, 4H), 2.50 (t, J=7.6 Hz, 2H), 2.22 (s, 3H), 1.82-1.71 (m, 2H), 1.69-1.63 (m, 2H).

Example 18 3-(3-(4-(4-(4-methyl-2-oxopyridin-1(2H)-yl)phenyl)piperazin-1-yl)propyl)-1H-indole-5-carbonitrile

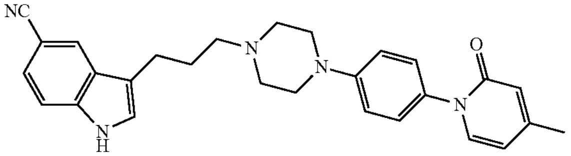 [SMILES: Cc1ccn(-c2ccc(N3CCN(CCCc4c[nH]c5ccc(C#N)cc45)CC3)cc2)c(=O)c1]

The title compound was prepared by the procedure described in step 2 of example 1, using 4-methyl-1-(4-(piperazin-1-yl)phenyl)pyridin-2(1H)-one (0.16 g, 0.60 mmol), 3-(5-cyano-1H-indol-3-yl)propyl 4-methylbenzene-sulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.16 g, 60.0%). The compound was characterized by the following spectroscopic data: MS (ESI, pos. ion) m/z: 452.3 $[M+H]^+$ and $^1H$ NMR (400 MHz, $CD_3OD$) δ (ppm): 7.98 (s, 1H), 7.45 (d, J=8.4 Hz, 1H), 7.38-7.34 (m, 2H), 7.20 (d, J=8.7 Hz, 3H), 7.02 (d, J=8.9 Hz, 2H), 6.43 (s, 1H), 6.29 (dd, J=6.8, 1.4 Hz, 1H), 3.28 (t, J=4.9 Hz, 4H), 2.83 (t, J=7.4 Hz, 2H), 2.68-2.66 (m, 4H), 2.53 (t, J=8.1 Hz, 2H), 2.27 (s, 3H), 2.00-1.93 (m, 2H).

Example 19 3-(2-(4-(4-(4-methyl-2-oxopyridin-1(2H)-yl)phenyl)piperazin-1-yl)ethyl)-1H-indole-5-carbonitrile

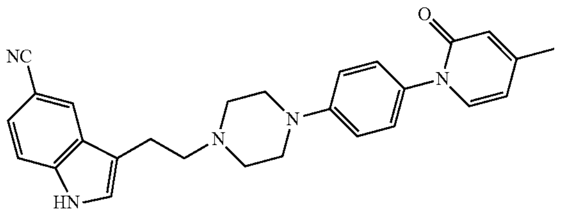 [SMILES: Cc1ccn(-c2ccc(N3CCN(CCc4c[nH]c5ccc(C#N)cc45)CC3)cc2)c(=O)c1]

To a solution of 3-(2-oxoethyl)-1H-indole-5-carbonitrile (0.11 g, 0.60 mmol) in a mixture of methanol (15 mL) and tetrahydrofuran (15 mL) were added 4-methyl-1-(4-(piperazin-1-yl)phenyl)pyridin-2(1H)-one (0.16 g, 0.60 mmol), sodium cyanoborohydride (0.11 g, 1.8 mmol) and acetic acid (0.1 mL) in turns at 0° C. The reaction mixture was stirred at room temperature for 10 hours, and then concentrated in vacuo. The residue was washed with water, dried, and purified by silica gel column chromatography ($CH_2Cl_2$/$CH_3OH$ (v/v)=20/1) to give the title compound as a yellow solid (0.18 g, 68.0%). The compound was characterized by the following spectroscopic data: MS (ESI, pos. ion) m/z: 438.3 $[M+H]^+$ and $^1H$ NMR (400 MHz, $CD_3OD$) δ (ppm): 9.82 (s, 1H), 8.58 (d, J=3.0 Hz, 1H), 8.57 (s, 1H), 8.09 (s, 1H), 7.70 (d, J=8.5 Hz, 1H), 7.66 (s, 1H), 7.62 (dd, J=8.5, 1.6 Hz, 1H), 7.55 (d, J=9.0 Hz, 1H), 7.45 (s, 1H), 7.29 (d, J=2.2 Hz, 1H), 7.25 (dd, J=9.1, 2.4 Hz, 1H), 3.81 (t, J=12.5 Hz, 2H), 3.68 (t, J=11.4 Hz, 2H), 3.25-3.20 (m, 4H), 3.11-2.98 (m, 4H), 2.23 (s, 3H).

Example 20 3-(5-(4-(4-(4-methyl-2-oxopyridin-1(2H)-yl)phenyl)piperazin-1-yl)pentyl)-1H-indole-5-carbonitrile

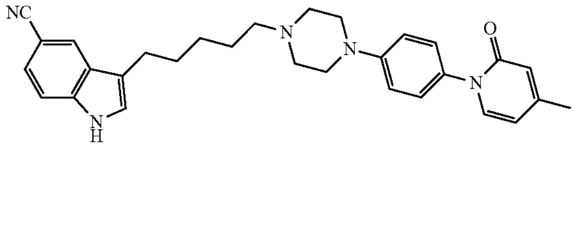 [SMILES: Cc1ccn(-c2ccc(N3CCN(CCCCCc4c[nH]c5ccc(C#N)cc45)CC3)cc2)c(=O)c1]

The title compound was prepared by the procedure described in step 2 of example 1, using 4-methyl-1-(4-(piperazin-1-yl)phenyl)pyridin-2(1H)-one (0.16 g, 0.60 mmol), 3-(5-chloropentyl)-1H-indole-5-carbonitrile (0.15 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.23 g, 80.0%). The compound was characterized by the following spectroscopic data: MS (ESI, pos. ion) m/z: 480.3 $[M+H]^+$ and $^1H$ NMR (400 MHz, $CDCl_3$) δ (ppm): 8.91 (s, 1H), 7.92 (s, 1H), 7.38-7.33 (m, 2H), 7.23-7.21 (m, 3H), 7.02 (d, J=1.7 Hz, 1H), 6.92 (d, J=8.9 Hz, 2H), 6.46 (s, 1H), 6.08 (dd, J=7.0, 1.7 Hz, 1H), 3.27 (t, J=4.6 Hz, 4H), 2.74 (t, J=7.5 Hz, 2H), 2.66 (t, J=4.6 Hz, 4H), 2.46 (t, J=7.6 Hz, 2H), 2.22 (s, 3H), 1.73-1.67 (m, 2H), 1.65-1.60 (m, 2H), 1.46-1.38 (m, 2H).

Example 21 3-(4-(4-(4-(4-methoxy-2-oxopyridin-1(2H)-yl)phenyl)piperazin-1-yl)butyl)-1H-indole-5-carbonitrile

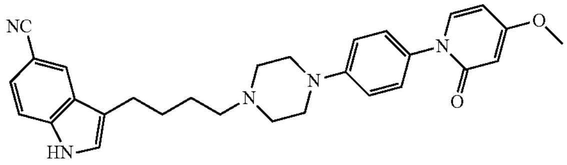 [SMILES: COc1ccn(-c2ccc(N3CCN(CCCCc4c[nH]c5ccc(C#N)cc45)CC3)cc2)c(=O)c1]

Step 1) 4-methoxy-1-(4-(piperazin-1-yl)phenyl)pyridin-2(1H)-one

The title compound was prepared by the procedure described in step 1 of example 1, using 1-(4-aminophenyl)-4-methoxypyridin-2(1H)-one (2.16 g, 10.0 mmol), bis(2-chloroethyl)amine hydrochloride (1.96 g, 11.0 mmol) and potassium carbonate (1.5 g, 11.0 mmol) in n-butyl alcohol (20 mL) to give the crude product, which was purified by silica gel column chromatography ($CH_2Cl_2$/$CH_3OH$ (v/v)=20/1) to give the title compound as a white solid (2.00 g, 70.0%). The compound was characterized by the following spectroscopic data: MS (ESI, pos. ion) m/z: 286.2 $[M+H]^+$ and $^1H$ NMR (400 MHz, DMSO-$d_6$) δ (ppm): 7.48 (d, J=7.2 Hz, 1H), 7.15 (d, J=7.6 Hz, 2H), 6.98 (d, J=8.0 Hz, 2H), 5.99 (d, J=5.6 Hz, 1H), 5.85 (s, 1H), 3.77 (s, 3H), 3.49 (brs, 4H), 2.85 (brs, 4H).

Step 2) 3-(4-(4-(4-(4-methoxy-2-oxopyridin-1(2H)-yl)phenyl)piperazin-1-yl)butyl)-1H-indole-5-carbonitrile The title compound was prepared by the procedure described in step 2 of example 1, using 4-methoxy-1-(4-(piperazin-1-yl)phenyl)pyridin-2(1H)-one (0.17 g, 0.60 mmol), 4-(5-cyano-1H-indol-3-yl)butyl 4-methylbenzene-sulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.14 g, 50.0%). The compound was characterized by the following spectroscopic data: MS (ESI, pos. ion) m/z: 482.4 $[M+H]^+$ and $^1H$ NMR (400 MHz, $CF_3COOH$/DMSO- $d_6$) δ (ppm): 9.91 (brs, 1H), 8.11 (s, 1H), 7.53 (d, J=8.4 Hz, 1H), 7.49 (d, J=7.6 Hz, 1H), 7.42 (dd, J=8.4, 1.6 Hz, 1H), 7.39 (d, J=1.6 Hz, 1H), 7.24 (d, J=8.8 Hz, 2H), 7.09 (d, J=8.8 Hz, 2H), 6.11 (dd, J=7.6, 2.8 Hz, 1H), 5.86 (d, J=2.4 Hz, 1H), 3.91-3.88 (m, 2H), 3.78 (s, 3H), 3.61-3.58 (m, 2H), 3.17 (brs, 4H), 3.06-3.00 (m, 2H), 2.81-2.77 (m, 2H), 1.71 (brs, 4H).

Example 22 3-(3-(4-(4-(4-methoxy-2-oxopyridin-1 (2H)-yl)phenyl)piperazin-1-yl)propyl)-1H-indole-5-carbonitrile

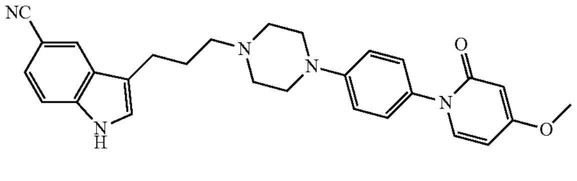 [SMILES: COc1ccn(-c2ccc(N3CCN(CCCc4c[nH]c5ccc(C#N)cc45)CC3)cc2)c(=O)c1]

The title compound was prepared by the procedure described in step 2 of example 1, using 4-methoxy-1-(4-(piperazin-1-yl)phenyl)pyridin-2(1H)-one (0.17 g, 0.60 mmol), 3-(5-cyano-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.13 g, 46.0%). The compound was characterized by the following spectroscopic data: MS (ESI, pos. ion) m/z: 468.3 $[M+H]^+$ and $^1H$ NMR (400 MHz, $CD_3OD/CDCl_3$) δ (ppm): 7.97 (s, 1H), 7.44 (d, J=8.4 Hz, 1H), 7.36 (dd, J=8.4, 1.2 Hz, 1H), 7.33 (d, J=7.6 Hz, 1H), 7.20-7.18 (m, 3H), 7.00 (d, J=9.2 Hz, 2H), 6.11 (dd, J=7.6, 2.4 Hz, 1H), 5.96 (d, J=2.4 Hz, 1H), 3.84 (s, 3H), 3.27 (t, J=4.8 Hz, 4H), 2.82 (t, J=7.2 Hz, 2H), 2.68 (t, J=4.8 Hz, 4H), 2.55-2.51 (m, 2H), 2.01-1.93 (m, 2H).

Example 23 3-(2-(4-(4-(4-methoxy-2-oxopyridin-1 (2H)-yl)phenyl)piperazin-1-yl)ethyl)-1H-indole-5-carbonitrile

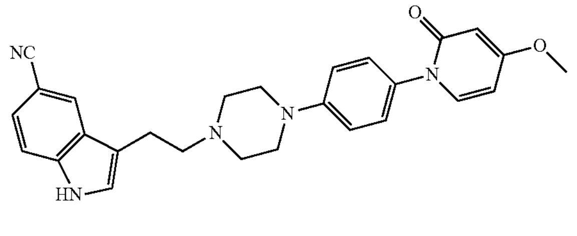 [SMILES: COc1ccn(-c2ccc(N3CCN(CCc4c[nH]c5ccc(C#N)cc45)CC3)cc2)c(=O)c1]

To a solution of 3-(2-oxoethyl)-1H-indole-5-carbonitrile (0.11 g, 0.60 mmol) in a mixture of methanol (15 mL) and tetrahydrofuran (15 mL) were added 4-methoxy-1-(4-(piperazin-1-yl)phenyl)pyridin-2(1H)-one (0.17 g, 0.60 mmol), sodium cyanoborohydride (0.11 g, 1.8 mmol) and acetic acid (0.1 mL) in turns at 0° C. The reaction mixture was stirred at room temperature for 10 hours, and then concentrated in vacuo. The residue was washed with water, dried, and purified by silica gel column chromatography ($CH_2Cl_2$/$CH_3OH$ (v/v)=20/1) to give the title compound as a pale yellow solid (0.16 g, 60.0%). The compound was characterized by the following spectroscopic data: MS (ESI, pos. ion) m/z: 454.3 $[M+H]^+$ and $^1H$ NMR (400 MHz, DMSO-$d_6$) δ (ppm): 10.04 (br s, 1H), 8.24 (s, 1H), 7.56 (d, J=8.4 Hz, 1H), 7.51-7.45 (m, 3H), 7.25 (d, J=8.8 Hz, 2H), 7.13 (d, J=8.8 Hz, 2H), 6.03 (dd, J=7.6, 2.8 Hz, 1H), 5.87 (d, J=2.8 Hz, 1H), 3.98-3.95 (m, 2H), 3.78 (s, 3H), 3.78-3.75 (m, 2H), 3.48-3.46 (m, 2H), 3.29-3.17 (m, 4H), 3.12-3.06 (m, 2H).

Example 24 3-(5-(4-(4-(4-methoxy-2-oxopyridin-1 (2H)-yl)phenyl)piperazin-1-yl)pentyl)-1H-indole-5-carbonitrile

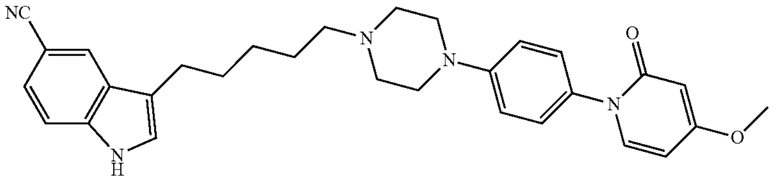 [SMILES: COc1ccn(-c2ccc(N3CCN(CCCCCc4c[nH]c5ccc(C#N)cc45)CC3)cc2)c(=O)c1]

The title compound was prepared by the procedure described in step 2 of example 1, using 4-methoxy-1-(4-(piperazin-1-yl)phenyl)pyridin-2(1H)-one (0.17 g, 0.60 mmol), 3-(5-chloropentyl)-1H-indole-5-carbonitrile (0.15 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.22 g, 75.0%). The compound was characterized by the following spectroscopic data: MS (ESI, pos. ion) m/z: 496.3 $[M+H]^+$ and $^1H$ NMR (400 MHz, $CD_3OD/CDCl_3$) δ (ppm): 7.93 (s, 1H), 7.43 (d, J=8.4 Hz, 1H), 7.31-7.36 (m, 2H), 7.19 (d, J=8.8 Hz, 2H), 7.14 (s, 1H), 7.00 (d, J=8.8 Hz, 2H), 6.12 (dd, J=7.6, 2.8 Hz, 1H), 5.97 (d, J=2.8 Hz, 1H), 3.84 (s, 3H), 3.26 (brs, 4H), 2.78 (t, J=7.2 Hz, 2H), 2.66 (brs, 4H), 2.46-2.42 (m, 2H), 1.79-1.72 (m, 2H), 1.66-1.60 (m, 2H), 1.58-1.46 (m, 2H).

Example 25 3-(4-(4-(4-(3,5-difluoro-2-oxopyridin-1 (2H)-yl)phenyl)piperazin-1-yl)butyl)-1H-indole-5-carbonitrile

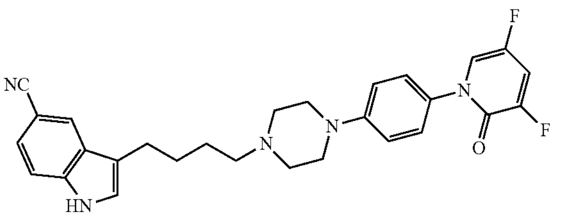 [SMILES: N#Cc1ccc2[nH]cc(CCCCN3CCN(c4ccc(-n5cc(F)cc(F)c5=O)cc4)CC3)c2c1]

Step 1) 3,5-difluoro-1-(4-(piperazin-1-yl)phenyl) pyridin-2(1H)-one

The title compound was prepared by the procedure described in step 1 of example 1, using 1-(4-aminophenyl)-3,5-difluoropyridin-2(1H)-one (2.22 g, 10.0 mmol), bis(2-chloroethyl)amine hydrochloride (1.96 g, 11.0 mmol) and potassium carbonate (1.5 g, 11.0 mmol) in n-butyl alcohol (20 mL) to give the crude product, which was purified by silica gel column chromatography ($CH_2Cl_2$/$CH_3OH$ (v/v)=20/1) to give the title compound as a white solid (1.75 g, 70.0%). The compound was characterized by the following spectroscopic data: MS (ESI, pos. ion) m/z: 292.1 $[M+H]^+$ and $^1H$ NMR (400 MHz, DMSO-$d_6$) δ (ppm): 7.91-7.85 (m, 1H), 7.82-7.80 (m, 1H), 7.31 (d, J=8.8 Hz, 2H), 7.08 (d, J=8.8 Hz, 2H), 3.38 (t, J=4.8 Hz, 4H), 3.13 (brs, 4H).

Step 2) 3-(4-(4-(4-(3,5-difluoro-2-oxopyridin-1 (2H)-yl)phenyl)piperazin-1-yl)butyl)-1H-indole-5-carbonitrile The title compound was prepared by the procedure described in step 2 of example 1, using 3,5-difluoro-1-(4-(piperazin-1-yl)phenyl)pyridin-2(1H)-one (0.18 g, 0.60 mmol), 4-(5-cyano-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.19 g, 75.0%). The compound was characterized by the following spectroscopic data: MS (ESI, pos. ion) m/z: 488.4 $[M+H]^+$ and $^1H$ NMR (400 MHz, DMSO-$d_6$) δ (ppm): 8.07 (s, 1H), 7.82-7.77 (m, 1H), 7.74-7.71 (m, 1H), 7.51 (d, J=8.4 Hz, 1H), 7.40 (dd, J=8.4, 1.6 Hz, 1H), 7.35-7.32 (m, 3H), 7.11 (d, J=9.2 Hz, 2H), 3.92-3.89 (m, 2H), 3.60-3.57 (m, 2H), 3.23-3.06 (m, 6H), 2.81-2.77 (m, 2H), 1.73-1.72 (m, 4H).

Example 26 3-(3-(4-(4-(3,5-difluoro-2-oxopyridin-1 (2H)-yl)phenyl)piperazin-1-yl)propyl)-1H-indole-5-carbonitrile

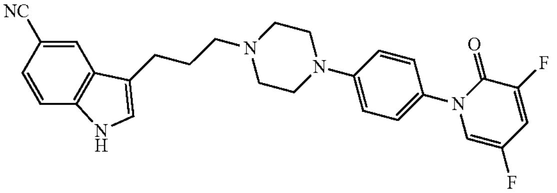 [SMILES: N#Cc1ccc2[nH]cc(CCCN3CCN(c4ccc(-n5cc(F)cc(F)c5=O)cc4)CC3)c2c1]

The title compound was prepared by the procedure described in step 2 of example 1, using 3,5-difluoro-1-(4-(piperazin-1-yl)phenyl)pyridin-2(1H)-one (0.18 g, 0.60 mmol), 3-(5-cyano-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.18 g, 63.0%). The compound was characterized by the following spectroscopic data: MS (ESI, pos. ion) m/z: 474.1 $[M+H]^+$ and $^1H$ NMR (400 MHz, $CD_3OD$/$CDCl_3$) δ (ppm): 7.97 (s, 1H), 7.46-7.41 (m, 2H), 7.36 (dd, J=9.6, 5.6 Hz, 2H), 7.26 (d, J=9.2 Hz, 2H), 7.19 (s, 1H), 7.02 (d, J=9.2 Hz, 2H), 3.30 (brs, 4H), 2.83 (t, J=7.2 Hz, 2H), 2.69 (brs, 4H), 2.56-2.52 (m, 2H), 2.02-1.94 (m, 2H).

Example 27 3-(2-(4-(4-(3,5-difluoro-2-oxopyridin-1 (2H)-yl)phenyl)piperazin-1-yl)ethyl)-1H-indole-5-carbonitrile

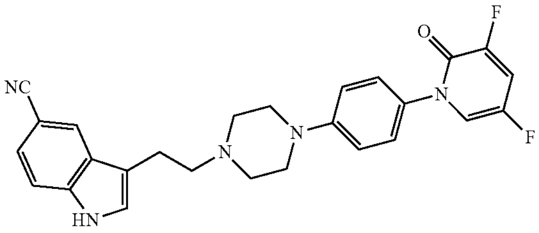 [SMILES: N#Cc1ccc2[nH]cc(CCN3CCN(c4ccc(-n5cc(F)cc(F)c5=O)cc4)CC3)c2c1]

To a solution of 3-(2-oxoethyl)-1H-indole-5-carbonitrile (0.11 g, 0.60 mmol) in a mixture of methanol (15 mL) and tetrahydrofuran (15 mL) were added 3,5-difluoro-1-(4-(piperazin-1-yl)phenyl)pyridin-2(1H)-one (0.18 g, 0.60 mmol), sodium cyanoborohydride (0.11 g, 1.8 mmol) and acetic acid (0.1 mL) in turns at 0° C. The reaction mixture was stirred at room temperature for 10 hours, and then concentrated in vacuo. The residue was washed with water, dried, and purified by silica gel column chromatography ($CH_2Cl_2$/$CH_3OH$ (v/v)=20/1) to give the title compound as a pale yellow solid (0.18 g, 65.0%). The compound was characterized by the following spectroscopic data: MS (ESI, pos. ion) m/z: 460.1 $[M+H]^+$ and $^1H$ NMR (400 MHz, $CD_3OD$/$CDCl_3$) δ (ppm): 11.42 (s, 1H), 8.13 (s, 1H), 7.89-7.80 (m, 2H), 7.51 (d, J=8.5 Hz, 1H), 7.42-7.40 (m, 2H), 7.28 (d, J=9.0 Hz, 2H), 7.04 (d, J=9.1 Hz, 2H), 3.25-3.23 (m, 4H), 2.94 (t, J=7.6 Hz, 2H), 2.66 (t, J=6.1 Hz, 6H).

Example 28 3-(5-(4-(4-(3,5-difluoro-2-oxopyridin-1 (2H)-yl)phenyl)piperazin-1-yl)pentyl)-1H-indole-5-carbonitrile

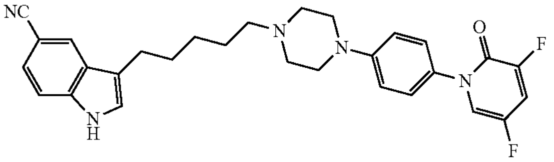 [SMILES: N#Cc1ccc2[nH]cc(CCCCCN3CCN(c4ccc(-n5cc(F)cc(F)c5=O)cc4)CC3)c2c1]

The title compound was prepared by the procedure described in step 2 of example 1, using 3,5-difluoro-1-(4-(piperazin-1-yl)phenyl)pyridin-2(1H)-one (0.18 g, 0.60 mmol), 3-(5-chloropentyl)-1H-indole-5-carbonitrile (0.15 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.21 g, 75.0%). The compound was characterized by the following spectroscopic data: MS (ESI, pos. ion) m/z: 502.3 $[M+H]^+$ and $^1H$ NMR (400 MHz, $CD_3OD$/$CDCl_3$) δ (ppm): 8.09 (s, 1H), 7.56 (d, J=8.5 Hz, 1H), 7.51 (dd, J=8.5, 1.5 Hz, 1H), 7.47-7.35 (m, 4H), 7.14 (m, 2H), 7.12 (m, 1H), 3.47-3.38 (m, 4H), 2.92 (t, J=7.5 Hz, 2H), 2.86-2.77 (m, 4H), 2.60 (t, J=7.5 Hz, 2H), 1.90-1.85 (m, 2H), 1.77-1.75 (m, 2H), 1.56-1.54 (m, 2H).

Example 29 3-(4-(4-(4-(1-oxoisoquinolin-2(1H)-yl)phenyl)piperazin-1-yl)butyl)-1H-indole-5-carbonitrile

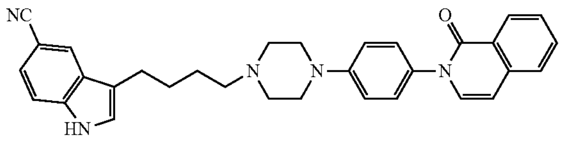 [SMILES: N#Cc1ccc2[nH]cc(CCCCN3CCN(c4ccc(-n5ccc6ccccc6c5=O)cc4)CC3)c2c1]

Step 1) 2-(4-(piperazin-1-yl)phenyl)isoquinolin-1(2H)-one

The title compound was prepared by the procedure described in step 1 of example 1, using 2-(4-aminophenyl)isoquinolin-1(2H)-one (2.36 g, 10.0 mmol), bis(2-chloroethyl)amine hydrochloride (1.96 g, 11.0 mmol) and potassium carbonate (1.5 g, 11.0 mmol) in n-butyl alcohol (20 mL) to give the crude product, which was purified by silica gel column chromatography ($CH_2Cl_2/CH_3OH$ (v/v)=20/1) to give the title compound as a white solid (1.22 g, 40.0%). The compound was characterized by the following spectroscopic data: MS (ESI, pos. ion) m/z: 306.1 $[M+H]^+$ and $^1H$ NMR (400 MHz, DMSO-$d_6$) δ (ppm): 9.00 (brs, 2H), 8.25 (d, J=8.0 Hz, 1H), 7.77-7.71 (m, 2H), 7.57-7.55 (m, 1H), 7.41-7.34 (m, 1H), 7.12 (d, J=8.8 Hz, 2H), 6.70 (d, J=7.6 Hz, 1H), 3.42 (t, J=4.8 Hz, 4H), 3.28 (brs, 4H).

Step 2) 3-(4-(4-(4-(1-oxoisoquinolin-2(1H)-yl)phenyl)piperazin-1-yl)butyl)-1H-indole-5-carbonitrile The title compound was prepared by the procedure described in step 2 of example 1, using 2-(4-(piperazin-1-yl)phenyl)isoquinolin-1(2H)-one (0.18 g, 0.60 mmol), 4-(5-cyano-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.12 g, 45.0%). The compound was characterized by the following spectroscopic data: MS (ESI, pos. ion) m/z: 502.4 $[M+H]^+$ and $^1H$ NMR (400 MHz, DMSO-$d_6$) δ (ppm): 11.55 (s, 1H), 10.08 (brs, 1H), 8.26 (d, J=8.0 Hz, 1H), 8.12 (s, 1H), 7.77-7.71 (m, 2H), 7.57-7.53 (m, 2H), 7.44-7.39 (m, 2H), 7.35 (d, J=9.2 Hz, 2H), 7.13 (d, J=8.8 Hz, 2H), 6.70 (d, J=7.2 Hz, 1H), 3.94-3.91 (m, 2H), 3.63-3.60 (m, 2H), 3.24-3.16 (m, 4H), 3.10-3.04 (m, 2H), 2.79 (t, J=7.2 Hz, 2H), 1.71-1.74 (m, 4H).

Example 30 3-(3-(4-(4-(1-oxoisoquinolin-2(1H)-yl)phenyl)piperazin-1-yl)propyl)-1H-indole-5-carbonitrile

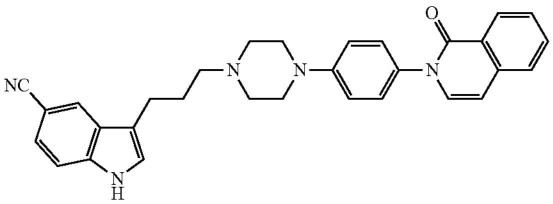 [SMILES: N#Cc1ccc2[nH]cc(CCCN3CCN(c4ccc(-n5ccc6ccccc6c5=O)cc4)CC3)c2c1]

The title compound was prepared by the procedure described in step 2 of example 1, using 2-(4-(piperazin-1-yl)phenyl)isoquinolin-1(2H)-one (0.18 g, 0.60 mmol), 3-(5-cyano-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.10 g, 34.0%). The compound was characterized by the following spectroscopic data: MS (ESI, pos. ion) m/z: 488.2 $[M+H]^+$ and $^1H$ NMR (400 MHz, $CD_3OD/CDCl_3$) δ (ppm): 8.38 (d, J=8.0 Hz, 1H), 7.95 (s, 1H), 7.71-7.66 (m, 1H), 7.58 (d, J=7.6 Hz, 1H), 7.52 (t, J=8.0 Hz, 1H), 7.43-7.41 (m, 1H), 7.35 (dd, J=8.8, 1.6 Hz, 1H), 7.27 (d, J=8.8 Hz, 2H), 7.18 (d, J=7.2 Hz, 1H), 7.15 (s, 1H), 7.01 (d, J=8.8 Hz, 2H), 7.27 (d, J=7.6 Hz, 1H), 3.30-3.28 (m, 4H), 2.81 (t, J=7.2 Hz, 2H), 2.69 (brs, 4H), 2.54 (t, J=8.0 Hz, 2H), 2.01-1.93 (m, 2H).

Example 31 3-(4-(4-(4-(5-oxo-1,6-naphthyridin-6(5H)-yl)phenyl)piperazin-1-yl)butyl)-1H-indole-5-carbonitrile

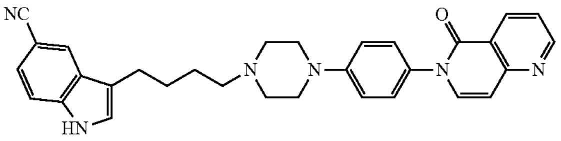 [SMILES: N#Cc1ccc2[nH]cc(CCCCN3CCN(c4ccc(-n5ccc6ncccc6c5=O)cc4)CC3)c2c1]

Step 1) 6-(4-(piperazin-1-yl)phenyl)-1,6-naphthyridin-5(6H)-one

The title compound was prepared by the procedure described in step 1 of example 1, using 6-(4-aminophenyl)-1,6-naphthyridin-5(6H)-one (2.37 g, 10.0 mmol), bis(2-chloroethyl)amine hydrochloride (1.96 g, 11.0 mmol) and potassium carbonate (1.5 g, 11.0 mmol) in n-butyl alcohol (20 mL) to give the crude product, which was purified by silica gel column chromatography ($CH_2Cl_2/CH_3OH$ (v/v) =20/1) to give the title compound as a white solid (1.07 g, 35.0%). The compound was characterized by the following spectroscopic data: MS (ESI, pos. ion) m/z: 307.3 $[M+H]^+$ and $^1H$ NMR (400 MHz, DMSO-$d_6$) δ (ppm): 8.96 (dd, J=4.8, 1.6 Hz, 1H), 8.56 (dd, J=7.6, 1.6 Hz, 1H), 7.67 (d, J=7.6 Hz, 1H), 7.57 (dd, J=8.4, 4.8 Hz, 1H), 7.37 (d, J=8.8 Hz, 2H), 7.13 (d, J=8.8 Hz, 2H), 6.77 (d, J=7.6 Hz, 1H), 3.46 (t, J=4.8 Hz, 4H), 3.26 (brs, 4H).

Step 2) 3-(4-(4-(4-(5-oxo-1,6-naphthyridin-6(5H)-yl)phenyl)piperazin-1-yl)butyl)-1H-indole-5-carbonitrile The title compound was prepared by the procedure described in step 2 of example 1, using 6-(4-(piperazin-1-yl)phenyl)-1,6-naphthyridin-5(6H)-one (0.18 g, 0.60 mmol), 4-(5-cyano-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.13 g, 43.0%). The compound was characterized by the following spectroscopic data: MS (ESI, pos. ion) m/z: 503.3 $[M+H]^+$ and $^1H$ NMR (400 MHz, $CF_3COOH/DMSO-d_6$) δ (ppm): 11.45 (s, 1H), 9.07 (dd, J=4.8, 1.2 Hz, 1H), 8.79 (d, J=7.6 Hz, 1H), 8.11 (s, 1H), 7.81 (d, J=7.6 Hz, 1H), 7.73 (dd, J=8.0, 4.8 Hz, 1H), 7.52 (d, J=8.4 Hz, 1H), 7.37-7.43 (m, 4H), 7.16 (d, J=9.2 Hz, 2H), 6.83 (d, J=7.6 Hz, 1H), 3.96-3.93 (m, 2H), 3.62-3.59 (m, 2H), 3.23-3.14 (m, 4H), 3.0.9-3.03 (m, 2H), 2.80 (t, J=5.6 Hz, 2H), 1.73-1.71 (m, 4H).

Example 32 3-(3-(4-(4-(5-oxo-1,6-naphthyridin-6(5H)-yl)phenyl)piperazin-1-yl)propyl)-1H-indole-5-carbonitrile

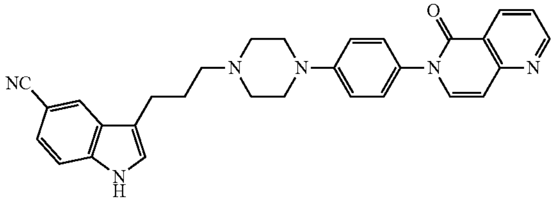 [SMILES: N#Cc1ccc2[nH]cc(CCCN3CCN(c4ccc(-n5ccc6ncccc6c5=O)cc4)CC3)c2c1]

The title compound was prepared by the procedure described in step 2 of example 1, using 6-(4-(piperazin-1-yl)phenyl)-1,6-naphthyridin-5(6H)-one (0.18 g, 0.60 mmol), 3-(5-cyano-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.14 g, 47.0%). The compound was characterized by the following spectroscopic data: MS (ESI, pos. ion) m/z: 489.2 $[M+H]^+$ and $^1H$ NMR (400 MHz, $CDCl_3$) δ (ppm): 9.18 (s, 1H), 8.93-8.92 (m, 1H), 8.73 (d, J=9.2 Hz, 1H), 7.95 (s, 1H), 7.44-7.28 (m, 6H), 7.04 (s, 1H), 6.96 (d, J=9.2 Hz, 2H), 6.82 (d, J=7.8 Hz, 1H), 3.26 (t, J=4.9 Hz, 4H), 2.79 (t, J=4.6 Hz, 2H), 2.66 (t, J=4.9 Hz, 4H), 2.64 (t, J=4.6 Hz, 2H), 1.95-1.93 (m, 2H).

Example 33 3-(4-(4-(4-(4-oxofuro[3,2-c]pyridin-5(4H)-yl)phenyl)piperazin-1-yl)butyl)-1H-indole-5-carbonitrile

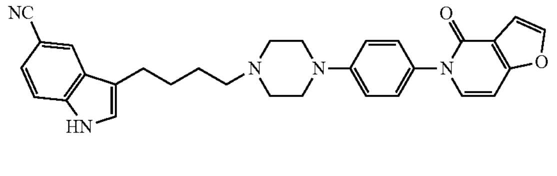 [SMILES: N#Cc1ccc2[nH]cc(CCCCN3CCN(c4ccc(-n5ccc6occc6c5=O)cc4)CC3)c2c1]

Step 1) 5-(4-(piperazin-1-yl)phenyl)furo[3,2-c]pyridin-4(5H)-one

The title compound was prepared by the procedure described in step 1 of example 1, using 5-(4-aminophenyl)furo[3,2-c]pyridin-4(5H)-one (2.26 g, 10.0 mmol), bis(2-chloroethyl)amine hydrochloride (1.96 g, 11.0 mmol) and potassium carbonate (1.5 g, 11.0 mmol) in n-butyl alcohol (20 mL) to give the crude product, which was purified by silica gel column chromatography ($CH_2Cl_2/CH_3OH$ (v/v)=20/1) to give the title compound as a white solid (1.06 g, 36.0%). The compound was characterized by the following spectroscopic data: MS (ESI, pos. ion) m/z: 296.2 $[M+H]^+$ and $^1H$ NMR (400 MHz, $CD_3OD$) δ (ppm): 7.81 (d, J=2.0 Hz, 1H), 7.53 (d, J=7.4 Hz, 1H), 7.43 (d, J=8.9 Hz, 2H), 7.23 (d, J=9.0 Hz, 2H), 7.11 (dd, J=2.0, 0.7 Hz, 1H), 6.92 (dd, J=7.5, 0.8 Hz, 1H), 3.60 (t, J=4.8 Hz, 4H), 3.48 (t, J=4.8 Hz, 4H).

Step 2) 3-(4-(4-(4-(4-oxofuro[3,2-c]pyridin-5(4H)-yl)phenyl)piperazin-1-yl)butyl)-1H-indole-5-carbonitrile The title compound was prepared by the procedure described in step 2 of example 1, using 5-(4-(piperazin-1-yl)phenyl)furo[3,2-c]pyridin-4(5H)-one (0.18 g, 0.60 mmol), 4-(5-cyano-1H-indol-3-yl)butyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.13 g, 45.0%). The compound was characterized by the following spectroscopic data: MS (ESI, pos. ion) m/z: 492.2 $[M+H]^+$ and $^1H$ NMR (400 MHz, $CD_3OD$) δ (ppm): 7.93 (s, 1H), 7.64 (d, J=2.1 Hz, 1H), 7.43 (d, J=8.4 Hz, 1H), 7.36-7.33 (m, 2H), 7.25 (d, J=8.9 Hz, 2H), 7.17 (s, 1H), 7.04 (d, J=9.0 Hz, 2H), 6.98 (dd, J=2.1, 0.7 Hz, 1H), 6.76 (dd, J=7.4, 0.6 Hz, 1H), 3.96-3.94 (m, 2H), 3.62-3.60 (m, 2H), 3.23-3.16 (m, 4H), 3.09-3.05 (m, 2H), 2.81-2.77 (m, 2H), 1.75-1.73 (m, 4H).

Example 34 3-(3-(4-(4-(4-oxofuro[3,2-c]pyridin-5(4H)-yl)phenyl)piperazin-1-yl)propyl)-1H-indole-5-carbonitrile

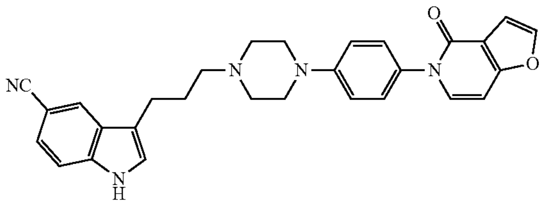 [SMILES: N#Cc1ccc2[nH]cc(CCCN3CCN(c4ccc(-n5ccc6occc6c5=O)cc4)CC3)c2c1]

The title compound was prepared by the procedure described in step 2 of example 1, using 5-(4-(piperazin-1-yl)phenyl)furo[3,2-c]pyridin-4(5H)-one (0.18 g, 0.60 mmol), 3-(5-cyano-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.12 g, 41.0%). The compound was characterized by the following spectroscopic data: MS (ESI, pos. ion) m/z: 478.2 $[M+H]^+$ and $^1H$ NMR (400 MHz, $CD_3OD$) δ (ppm): 7.97 (s, 1H), 7.65 (d, J=1.9 Hz, 1H), 7.63 (s, 1H), 7.44 (d, J=8.4 Hz, 1H), 7.37-7.34 (m, 2H), 7.24 (d, J=8.8 Hz, 2H), 7.19 (s, 1H), 7.04 (d, J=8.8 Hz, 2H), 6.98 (s, 1H), 6.76 (d, J=7.4 Hz, 1H), 3.91-3.87 (m, 2H), 3.69-3.67 (m, 2H), 3.30-3.13 (m, 6H), 2.92-2.89 (m, 2H), 2.21-2.18 (m, 2H).

Example 35 3-(4-(4-(4-(2-oxopyrazin-1(2H)-yl) phenyl)piperazin-1-yl)butyl)-1H-indole-5-carbonitrile

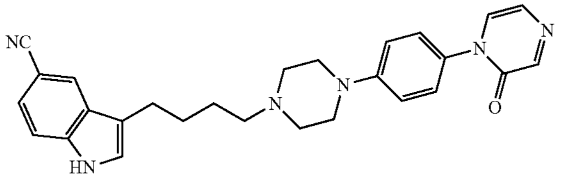 [SMILES: N#Cc1ccc2[nH]cc(CCCCN3CCN(c4ccc(-n5ccncc5=O)cc4)CC3)c2c1]

Step 1) 1-(4-(piperazin-1-yl)phenyl)pyrazin-2(1H)-one

The title compound was prepared by the procedure described in step 1 of example 1, using 1-(4-aminophenyl) pyrazin-2(1H)-one (1.87 g, 10.0 mmol), bis(2-chloroethyl) amine hydrochloride (1.96 g, 11.0 mmol) and potassium carbonate (1.5 g, 11.0 mmol) in n-butyl alcohol (20 mL) to give the crude product, which was purified by silica gel column chromatography ($CH_2Cl_2/CH_3OH$ (v/v)=20/1) to give the title compound as a white solid (1.48 g, 56.0%). The compound was characterized by the following spectroscopic data: MS (ESI, pos. ion) m/z: 257.2 $[M+H]^+$ and $^1H$ NMR (400 MHz, DMSO-$d_6$) δ (ppm): 9.05 (s, 2H), 8.09 (s, 1H), 7.61 (d, J=4.4 Hz, 1H), 7.37 (t, J=4.4 Hz, 3H), 7.12 (d, J=8.8 Hz, 2H), 3.44 (t, J=4.8 Hz, 4H), 3.26 (brs, 4H).

Step 2) 3-(4-(4-(4-(2-oxopyrazin-1(2H)-yl)phenyl) piperazin-1-yl)butyl)-1H-indole-5-carbonitrile The title compound was prepared by the procedure described in step 2 of example 1, using 1-(4-(piperazin-1-yl)phenyl)pyrazin-2(1H)-one (0.15 g, 0.60 mmol), 4-(5-cyano-1H-indol-3-yl)butyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.16 g, 59.0%). The compound was characterized by the following spectroscopic data: MS (ESI, pos. ion) m/z: 453.2 $[M+H]^+$ and $^1H$ NMR (400 MHz, DMSO-$d_6$) δ (ppm): 8.16 (s, 1H), 8.00 (s, 1H), 7.84 (s, 1H), 7.47-7.45 (m, 3H), 7.38-7.32 (m, 2H), 7.09-7.07 (m, 3H), 3.33-3.30 (m, 4H), 2.87-2.79 (m, 6H), 2.61-2.58 (m, 2H), 1.82-1.79 (m, 2H), 1.77-1.67 (m, 2H).

Example 36 3-(3-(4-(4-(2-oxopyrazin-1(2H)-yl) phenyl)piperazin-1-yl)propyl)-1H-indole-5-carbonitrile

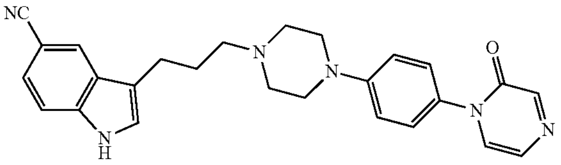 [SMILES: N#Cc1ccc2[nH]cc(CCCN3CCN(c4ccc(-n5ccncc5=O)cc4)CC3)c2c1]

The title compound was prepared by the procedure described in step 2 of example 1, using 1-(4-(piperazin-1-yl)phenyl)pyrazin-2(1H)-one (0.15 g, 0.60 mmol), 3-(5-cyano-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.15 g, 51.0%). The compound was characterized by the following spectroscopic data: MS (ESI, pos. ion) m/z: 439.2 $[M+H]^+$ and $^1H$ NMR (400 MHz, $CD_3OD/CDCl_3$) δ (ppm): 8.20 (s, 1H), 7.94 (s, 1H), 7.38-7.20 (m, 6H), 7.10 (s, 1H), 6.97-6.95 (m, 2H), 3.27-3.25 (m, 4H), 2.78 (t, J=7.2 Hz, 2H), 2.62-2.60 (m, 4H), 2.50-2.46 (m, 2H), 1.97-1.89 (m, 2H).

Example 37 3-(4-(4-(4-(2-oxotetrahydropyrimidin-1 (2H)-yl)phenyl)piperazin-1-yl)butyl)-1H-indole-5-carbonitrile

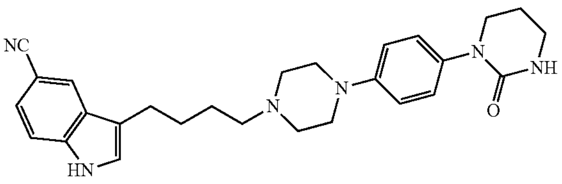 [SMILES: N#Cc1ccc2[nH]cc(CCCCN3CCN(c4ccc(N5CCCNC5=O)cc4)CC3)c2c1]

Step 1) 1-(4-(piperazin-1-yl)phenyl)tetrahydropyrimidin-2(1H)-one

The title compound was prepared by the procedure described in step 1 of example 1, using 1-(4-aminophenyl) tetrahydropyrimidin-2(1H)-one (1.91 g, 10.0 mmol), bis(2-chloroethyl)amine hydrochloride (1.96 g, 11.0 mmol) and potassium carbonate (1.5 g, 11.0 mmol) in n-butyl alcohol (20 mL) to give the crude product, which was purified by silica gel column chromatography ($CH_2Cl_2/CH_3OH$ (v/v)=20/1) to give the title compound as a white solid (1.77 g, 68.0%). The compound was characterized by the following spectroscopic data: MS (ESI, pos. ion) m/z: 261.3 $[M+H]^+$ and $^1H$ NMR (400 MHz, DMSO-$d_6$) δ (ppm): 7.09 (s, 2H), 6.86 (s, 2H), 3.56 (d, J=4.4 Hz, 2H), 3.39 (d, J=5.6 Hz, 2H), 3.07 (brs, 4H), 2.97 (brs, 4H), 2.07 (d, J=4.4 Hz, 2H).

Step 2) 3-(4-(4-(4-(2-oxotetrahydropyrimidin-1 (2H)-yl)phenyl)piperazin-1-yl)butyl)-1H-indole-5-carbonitrile The title compound was prepared by the procedure described in step 2 of example 1, using 1-(4-(piperazin-1- yl)phenyl)tetrahydropyrimidin-2(1H)-one (0.16 g, 0.60 mmol), 4-(5-cyano-1H-indol-3-yl)butyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.16 g, 59.0%). The compound was characterized by the following spectroscopic data: MS (ESI, pos. ion) m/z: 457.2 $[M+H]^+$ and $^1H$ NMR (400 MHz, $CD_3OD/CDCl_3$) δ (ppm): 7.95 (s, 1H), 7.44 (d, J=8.4 Hz, 1H), 7.36 (d, J=8.4 Hz, 1H), 7.15-7.13 (m, 3H), 6.93 (d, J=8.8 Hz, 2H), 3.65-3.62 (m, 2H), 3.41 (t, J=5.6 Hz, 2H), 3.19 (brs, 4H), 2.82 (t, J=7.2 Hz, 2H), 2.64 (brs, 4H), 2.47 (t, J=7.6 Hz, 2H), 2.08 (t, J=5.6 Hz, 2H), 1.76-1.74 (m, 2H), 1.67-1.65 (m, 2H).

Example 38 3-(3-(4-(4-(2-oxotetrahydropyrimidin-1(2H)-yl)phenyl)piperazin-1-yl)propyl)-1H-indole-5-carbonitrile

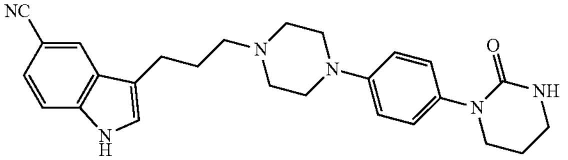 [SMILES: N#Cc1ccc2[nH]cc(CCCN3CCN(c4ccc(N5CCCNC5=O)cc4)CC3)c2c1]

The title compound was prepared by the procedure described in step 2 of example 1, using 1-(4-(piperazin-1-yl)phenyl)tetrahydropyrimidin-2(1H)-one (0.16 g, 0.60 mmol), 3-(5-cyano-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.16 g, 61.0%). The compound was characterized by the following spectroscopic data: MS (ESI, pos. ion) m/z: 443.4 $[M+H]^+$ and $^1H$ NMR (400 MHz, $CD_3OD/CDCl_3$) δ (ppm): 7.88 (s, 1H), 7.34-7.28 (m, 2H), 7.08-7.05 (m, 3H), 6.83 (d, J=8.4 Hz, 2H), 3.33 (t, J=5.6 Hz, 2H), 3.13 (brs, 4H), 2.73 (t, J=7.2 Hz, 2H), 2.56 (brs, 4H), 2.45-2.42 (m, 2H), 2.00 (t, J=5.2 Hz, 2H), 1.91-1.89 (m, 2H), 1.67-1.65 (m, 2H).

Example 39 3-(4-(4-(4-(6-oxopyrimidin-1(6H)-yl)phenyl)piperazin-1-yl)butyl)-1H-indole-5-carbonitrile

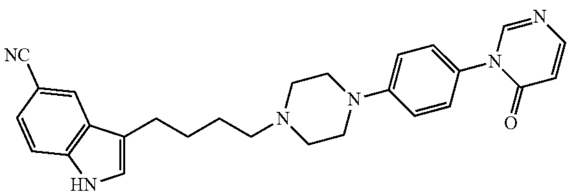 [SMILES: N#Cc1ccc2[nH]cc(CCCCN3CCN(c4ccc(-n5cnccc5=O)cc4)CC3)c2c1]

Step 1) 3-(4-(piperazin-1-yl)phenyl)pyrimidin-4(3H)-one

The title compound was prepared by the procedure described in step 1 of example 1, using 3-(4-aminophenyl)pyrimidin-4(3H)-one (1.87 g, 10.0 mmol), bis(2-chloroethyl)amine hydrochloride (1.96 g, 11.0 mmol) and potassium carbonate (1.5 g, 11.0 mmol) in n-butyl alcohol (20 mL) to give the crude product, which was purified by silica gel column chromatography ($CH_2Cl_2$/$CH_3OH$ (v/v)=20/1) to give the title compound as a white solid (1.26 g, 50.0%). The compound was characterized by the following spectroscopic data: MS (ESI, pos. ion) m/z: 257.2 $[M+H]^+$.

Step 2) 3-(4-(4-(4-(6-oxopyrimidin-1(6H)-yl)phenyl)piperazin-1-yl)butyl)-1H-indole-5-carbonitrile The title compound was prepared by the procedure described in step 2 of example 1, using 3-(4-(piperazin-1-yl)phenyl)pyrimidin-4(3H)-one (0.15 g, 0.60 mmol), 4-(5-cyano-1H-indol-3-yl)butyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.10 g, 38.0%). The compound was characterized by the following spectroscopic data: MS (ESI, pos. ion) m/z: 453.2 $[M+H]^+$ and $^1H$ NMR (400 MHz, $CD_3OD$) δ (ppm): 8.15 (s, 1H), 7.97 (s, 1H), 7.47-7.45 (m, 3H), 7.37 (dd, J=8.8, 1.6 Hz, 1H), 7.33 (d, J=9.2 Hz, 2H), 7.20 (s, 1H), 7.08 (d, J=8.8 Hz, 2H), 3.33 (brs, 4H), 2.87-2.80 (m, 2H), 2.79 (brs, 4H), 2.63 (brs, 2H), 1.77-1.73 (m, 2H), 1.68-1.67 (m, 2H).

Example 40 3-(3-(4-(4-(6-oxopyrimidin-1(6H)-yl)phenyl)piperazin-1-yl)propyl)-1H-indole-5-carbonitrile

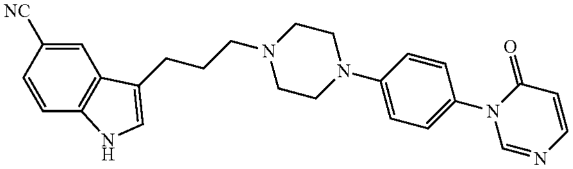 [SMILES: N#Cc1ccc2[nH]cc(CCCN3CCN(c4ccc(-n5cnccc5=O)cc4)CC3)c2c1]

The title compound was prepared by the procedure described in step 2 of example 1, using 3-(4-(piperazin-1-yl)phenyl)pyrimidin-4(3H)-one (0.15 g, 0.60 mmol), 3-(5-cyano-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.12 g, 42.0%). The compound was characterized by the following spectroscopic data: MS (ESI, pos. ion) m/z: 439.2 $[M+H]^+$ and $^1H$ NMR (400 MHz, $CDCl_3$) δ (ppm): 8.20 (s, 1H), 7.94 (s, 1H), 7.38-7.35 (m, 3H), 7.26-7.02 (m, 3H), 7.10 (s, 1H), 6.96 (d, J=9.2 Hz, 2H), 3.26 (t, J=4.8 Hz, 4H), 2.80-2.76 (m, 2H), 2.62 (t, J=4.8 Hz, 4H), 2.50-2.46 (m, 2H), 1.97-1.89 (m, 2H).

Example 41 5-(4-(4-(4-(5-fluoro-1H-indol-3-yl) butyl)piperazin-1-yl)phenyl)furo[3,2-c]pyridin-4 (5H)-one

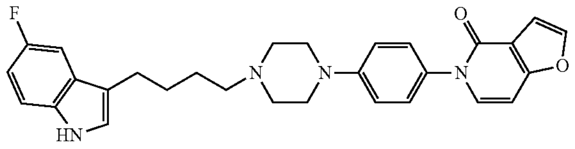 [SMILES: O=c1c2ccoc2ccn1-c1ccc(N2CCN(CCCCc3c[nH]c4ccc(F)cc34)CC2)cc1]

The title compound was prepared by the procedure described in step 2 of example 1, using 5-(4-(piperazin-1-yl)phenyl)furo[3,2-c]pyridin-4(5H)-one (0.18 g, 0.60 mmol), 4-(5-fluoro-1H-indol-3-yl)butyl 4-methylbenzene-sulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.15 g, 52.0%). The compound was characterized by the following spectroscopic data: MS (ESI, pos. ion) m/z: 485.2 $[M+H]^+$ and $^1H$ NMR (600 MHz, DMSO-$d_6$) δ (ppm): 10.69 (s, 1H), 7.95 (d, J=2.0 Hz, 1H), 7.53 (d, J=7.5 Hz, 1H), 7.29 (d, J=8.9 Hz, 2H), 7.26 (d, J=8.7 Hz, 1H), 7.17 (d, J=2.0 Hz, 1H), 7.11 (d, J=8.9 Hz, 2H), 7.04 (d, J=2.3 Hz, 1H), 7.00-6.98 (m, 1H), 6.82 (d, J=7.5 Hz, 1H), 6.75 (dd, J=8.7, 2.4 Hz, 1H), 3.79-3.77 (m, 2H), 3.51-3.47 (m, 6H), 3.18-3.13 (m, 4H), 2.75 (t, J=7.3 Hz, 2H), 2.10-2.03 (m, 2H).

Example 42 5-(4-(4-(3-(5-fluoro-1H-indol-3-yl) propyl)piperazin-1-yl)phenyl)furo[3,2-c]pyridin-4 (5H)-one

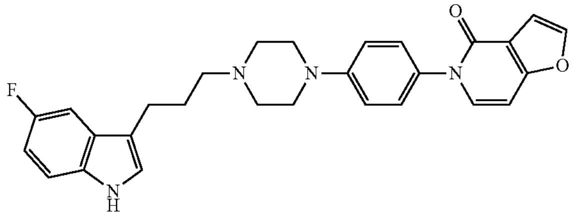 [SMILES: O=c1c2ccoc2ccn1-c1ccc(N2CCN(CCCc3c[nH]c4ccc(F)cc34)CC2)cc1]

The title compound was prepared by the procedure described in step 2 of example 1, using 5-(4-(piperazin-1-yl)phenyl)furo[3,2-c]pyridin-4 (5H)-one (0.18 g, 0.60 mmol), 3-(5-fluoro-1H-indol-3-yl)propyl 4-methylbenzene-sulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.15 g, 56.0%). The compound was characterized by the following spectroscopic data: MS (ESI, pos. ion) m/z: 471.2 $[M+H]^+$ and $^1H$ NMR (600 MHz, DMSO-$d_6$) δ (ppm): 10.97 (s, 1H), 7.94 (d, J=2.0 Hz, 1H), 7.53 (d, J=7.4 Hz, 1H), 7.33 (dd, J=8.8, 4.6 Hz, 1H), 7.27 (dd, J=10.1, 2.4 Hz, 1H), 7.22 (dd, J=5.8, 3.0 Hz, 3H), 7.02 (d, J=8.9 Hz, 2H), 6.99 (d, J=1.5 Hz, 1H), 6.90 (td, J=9.2, 2.5 Hz, 1H), 6.80 (s, 1H), 3.50 (t, J=4.8 Hz, 4H), 3.37 (d, J=7.2 Hz, 2H), 3.15 (t, J=4.8 Hz, 4H), 2.54-2.51 (m, 2H), 1.88-1.78 (m, 2H).

Example 43 5-(4-(4-(4-(5-methoxy-1H-indol-3-yl) butyl)piperazin-1-yl)phenyl)furo[3,2-c]pyridin-4 (5H)-one

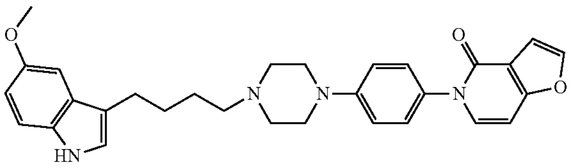 [SMILES: COc1ccc2[nH]cc(CCCCN3CCN(c4ccc(-n5ccc6occc6c5=O)cc4)CC3)c2c1]

The title compound was prepared by the procedure described in step 2 of example 1, using 5-(4-(piperazin-1-yl)phenyl)furo[3,2-c]pyridin-4(5H)-one (0.18 g, 0.60 mmol), 4-(5-methoxy-1H-indol-3-yl)butyl 4-methylbenze-nesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.12 g, 41.0%). The compound was characterized by the following spectroscopic data: MS (ESI, pos. ion) m/z: 497.3 $[M+H]^+$ and $^1H$ NMR (600 MHz, DMSO-$d_6$) δ (ppm): 10.59 (s, 1H), 7.94 (s, 1H), 7.54 (d, J=7.4 Hz, 1H), 7.22 (d, J=8.6 Hz, 3H), 7.07 (s, 1H), 7.03-7.00 (m, 3H), 6.98 (d, J=1.6 Hz, 1H), 6.79 (d, J=7.4 Hz, 1H), 6.71 (d, J=8.7 Hz, 1H), 3.76 (s, 3H), 3.51-3.47 (m, 4H), 3.19-3.16 (m, 4H), 2.68 (t, J=7.3 Hz, 2H), 2.38-2.35 (m, 2H), 1.67 (t, J=7.3 Hz, 2H), 1.59-1.50 (m, 2H).

Example 44 5-(4-(4-(3-(5-methoxy-1H-indol-3-yl) propyl)piperazin-1-yl)phenyl)furo[3,2-c]pyridin-4 (5H)-one

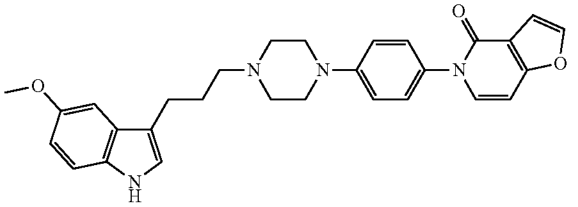 [SMILES: COc1ccc2[nH]cc(CCCN3CCN(c4ccc(-n5ccc6occc6c5=O)cc4)CC3)c2c1]

The title compound was prepared by the procedure described in step 2 of example 1, using 5-(4-(piperazin-1-yl)phenyl)furo[3,2-c]pyridin-4(5H)-one (0.18 g, 0.60 mmol), 3-(5-methoxy-1H-indol-3-yl)propyl 4-methylbenze-nesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.11 g, 38.0%). The compound was characterized by the following spectroscopic data: MS (ESI, pos. ion) m/z: 483.4 $[M+H]^+$ and $^1H$ NMR (600 MHz, DMSO-$d_6$) δ (ppm): 10.69 (brs, 1H), 7.95 (d, J=2.0 Hz, 1H), 7.53 (d, J=7.5 Hz, 1H), 7.29 (d, J=8.9 Hz, 2H), 7.26 (d, J=8.7 Hz, 1H), 7.17 (d, J=2.0 Hz, 1H), 7.11 (d, J=8.9 Hz, 2H), 7.04 (d, J=2.3 Hz, 1H), 7.00-6.98 (m, 1H), 6.82 (d, J=7.5 Hz, 1H), 6.75 (dd, J=8.7, 2.4 Hz, 1H), 3.79 (s, 3H), 3.51-3.44 (m, 6H), 3.30-3.17 (m, 4H), 2.75 (t, J=7.3 Hz, 2H), 2.10-2.03 (m, 2H).

Example 45 2-(4-(4-(4-(5-fluoro-1H-indol-3-yl)butyl)piperazin-1-yl)phenyl)isoquinolin-1(2H)-one

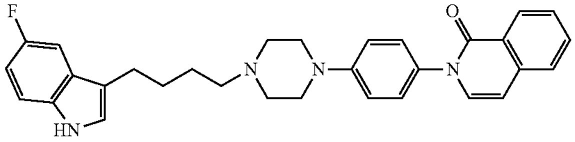 [SMILES: O=c1c2ccccc2ccn1-c1ccc(N2CCN(CCCCc3c[nH]c4ccc(F)cc34)CC2)cc1]

The title compound was prepared by the procedure described in step 2 of example 1, using 2-(4-(piperazin-1-yl)phenyl)isoquinolin-1(2H)-one (0.18 g, 0.60 mmol), 4-(5-fluoro-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.18 g, 60.0%). The compound was characterized by the following spectroscopic data: MS (ESI, pos. ion) m/z: 495.3 $[M+H]^+$ and $^1H$ NMR (400 MHz, DMSO-$d_6$) δ (ppm): 10.84 (s, 1H), 8.24 (d, J=8.0 Hz, 1H), 7.76-7.70 (m, 2H), 7.54-7.51 (m, 1H), 7.39 (d, J=7.4 Hz, 1H), 7.31 (dd, J=8.8, 4.6 Hz, 1H), 7.28-7.24 (m, 3H), 7.20 (d, J=2.0 Hz, 1H), 7.03 (d, J=9.0 Hz, 2H), 6.89 (td, J=9.2, 2.5 Hz, 1H), 6.68 (d, J=7.4 Hz, 1H), 3.19-3.17 (m, 4H), 2.68 (t, J=7.4 Hz, 2H), 2.53-2.48 (m, 4H), 2.38 (t, J=6.8 Hz, 2H), 1.71-1.64 (m, 2H), 1.58-1.51 (m, 2H).

Example 46 2-(4-(4-(3-(5-fluoro-1H-indol-3-yl)propyl)piperazin-1-yl)phenyl)isoquinolin-1(2H)-one

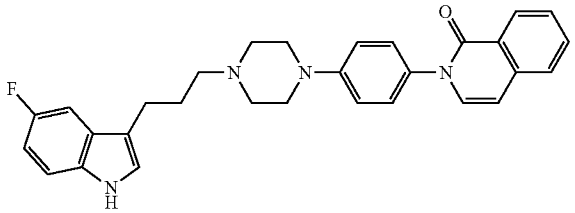 [SMILES: O=c1c2ccccc2ccn1-c1ccc(N2CCN(CCCc3c[nH]c4ccc(F)cc34)CC2)cc1]

The title compound was prepared by the procedure described in step 2 of example 1, using 2-(4-(piperazin-1-yl)phenyl)isoquinolin-1(2H)-one (0.18 g, 0.60 mmol), 3-(5-fluoro-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.20 g, 70.0%). The compound was characterized by the following spectroscopic data: MS (ESI, pos. ion) m/z: 481.2 $[M+H]^+$ and $^1H$ NMR (400 MHz, DMSO-$d_6$) δ (ppm): 10.87 (s, 1H), 8.25 (d, J=7.9 Hz, 1H), 7.77-7.70 (m, 2H), 7.54 (t, J=7.3 Hz, 1H), 7.40 (d, J=7.2 Hz, 1H), 7.33 (dd, J=8.7, 4.4 Hz, 1H), 7.29-7.27 (m, 3H), 7.22 (s, 1H), 7.04 (d, J=8.5 Hz, 2H), 6.90 (t, J=8.9 Hz, 1H), 6.68 (d, J=7.3 Hz, 1H), 3.30-3.23 (m, 4H), 2.70 (t, J=6.8 Hz, 2H), 2.55-2.50 (m, 4H), 2.41 (t, J=6.6 Hz, 2H), 1.88-1.81 (m, 2H).

Example 47 2-(4-(4-(4-(5-methoxy-1H-indol-3-yl)butyl)piperazin-1-yl)phenyl)isoquinolin-1(2H)-one

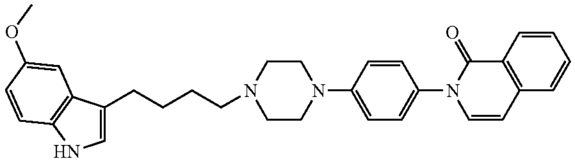 [SMILES: COc1ccc2[nH]cc(CCCCN3CCN(c4ccc(-n5ccc6ccccc6c5=O)cc4)CC3)c2c1]

The title compound was prepared by the procedure described in step 2 of example 1, using 2-(4-(piperazin-1-yl)phenyl)isoquinolin-1(2H)-one (0.18 g, 0.60 mmol), 4-(5-methoxy-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.12 g, 40.0%). The compound was characterized by the following spectroscopic data: MS (ESI, pos. ion) m/z: 507.2 $[M+H]^+$ and $^1H$ NMR (400 MHz, DMSO-$d_6$) δ (ppm): 10.56 (s, 1H), 8.24 (d, J=7.9 Hz, 1H), 7.76-7.68 (m, 2H), 7.54-7.42 (m, 2H), 7.39 (d, J=7.4 Hz, 1H), 7.27 (d, J=8.8 Hz, 1H), 7.21 (d, J=8.7 Hz, 1H), 7.07 (d, J=1.8 Hz, 1H), 7.03 (d, J=8.9 Hz, 2H), 6.98 (d, J=2.2 Hz, 1H), 6.71 (dd, J=8.7, 2.3 Hz, 1H), 6.68 (d, J=7.6 Hz, 1H), 3.82 (s, 3H), 3.53-3.49 (m, 4H), 3.18-3.12 (m, 4H), 2.65 (t, J=7.4 Hz, 2H), 2.37 (t, J=7.0 Hz, 2H), 1.84-1.77 (m, 2H), 1.58-1.51 (m, 2H).

Example 48 2-(4-(4-(3-(5-methoxy-1H-indol-3-yl)propyl)piperazin-1-yl)phenyl)iso quinolin-1(2H)-one

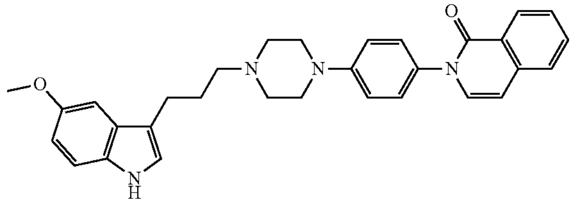 [SMILES: COc1ccc2[nH]cc(CCCN3CCN(c4ccc(-n5ccc6ccccc6c5=O)cc4)CC3)c2c1]

The title compound was prepared by the procedure described in step 2 of example 1, using 2-(4-(piperazin-1-yl)phenyl)isoquinolin-1(2H)-one (0.18 g, 0.60 mmol), 3-(5-methoxy-1H-indol-3-yl)propyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.13 g, 45.0%). The compound was characterized by the following spectroscopic data: MS (ESI, pos. ion) m/z: 493.3 $[M+H]^+$ and $^1H$ NMR (400 MHz, DMSO-$d_6$) δ (ppm): 10.53 (s, 1H), 8.20 (d, J=8.0 Hz, 1H), 7.73-7.65 (m, 2H), 7.50 (t, J=7.4 Hz, 1H), 7.35 (d, J=7.3 Hz, 1H), 7.23 (d, J=8.5 Hz, 1H), 7.18 (d, J=8.7 Hz, 1H), 7.05 (s, 1H), 6.99 (d, J=8.7 Hz, 2H), 6.94 (s, 1H), 6.67 (dd, J=8.9, 1.6 Hz, 1H), 6.64 (d, J=7.4 Hz, 2H), 3.79 (s, 3H), 3.18-3.12 (m, 4H), 2.65 (t, J=7.4 Hz, 2H), 2.46-2.40 (m, 4H), 2.37 (t, J=7.0 Hz, 2H), 1.84-1.77 (m, 2H).

Example 49 1-(4-(4-(4-(5-methoxy-1H-indol-3-yl)butyl)piperazin-1-yl)phenyl)pyridin-2(1H)-one

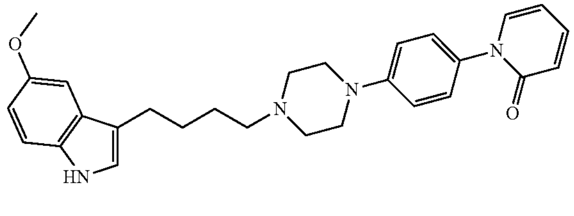 [SMILES: COc1ccc2[nH]cc(CCCCN3CCN(c4ccc(-n5ccccc5=O)cc4)CC3)c2c1]

The title compound was prepared by the procedure described in step 2 of example 1, using 1-(4-(piperazin-1-yl)phenyl)pyridin-2(1H)-one (0.15 g, 0.60 mmol), 4-(5-methoxy-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.11 g, 40.0%). The compound was characterized by the following spectroscopic data: MS (ESI, pos. ion) m/z: 457.1 $[M+H]^+$ and $^1H$ NMR (400 MHz, DMSO-$d_6$) δ (ppm): 10.56 (s, 1H), 7.57 (dd, J=6.7, 1.7 Hz, 1H), 7.48-7.45 (m, 1H), 7.22-7.19 (m, 3H), 7.06 (d, J=1.5 Hz, 1H), 6.99 (d, J=8.9 Hz, 2H), 6.97 (d, J=2.1 Hz, 1H), 6.70 (dd, J=8.7, 2.3 Hz, 1H), 6.44 (d, J=9.2 Hz, 1H), 6.26 (dd, J=9.6, 3.8 Hz, 1H), 3.75 (s, 3H), 3.17-3.16 (m, 4H), 2.67 (t, J=7.4 Hz, 2H), 2.50-2.46 (m, 4H), 2.43-2.30 (m, 2H), 1.69-1.64 (m, 2H), 1.56-1.51 (m, 2H).

Example 50 1-(4-(4-(3-(5-methoxy-1H-indol-3-yl)propyl)piperazin-1-yl)phenyl)pyridin-2(1H)-one

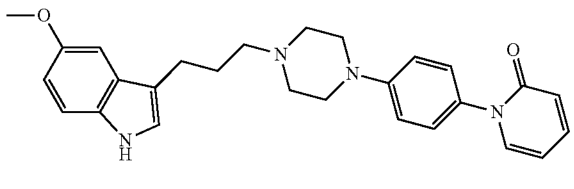 [SMILES: COc1ccc2[nH]cc(CCCN3CCN(c4ccc(-n5ccccc5=O)cc4)CC3)c2c1]

The title compound was prepared by the procedure described in step 2 of example 1, using 1-(4-(piperazin-1-yl)phenyl)pyridin-2(1H)-one (0.15 g, 0.60 mmol), 3-(5-methoxy-1H-indol-3-yl)propyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.12 g, 46.0%). The compound was characterized by the following spectroscopic data: MS (ESI, pos. ion) m/z: 443.1 $[M+H]^+$ and $^1H$ NMR (400 MHz, DMSO-$d_6$) δ (ppm): 10.58 (s, 1H), 7.57 (dd, J=6.9, 1.7 Hz, 1H), 7.49-7.44 (m, 1H), 7.23-7.19 (m, 3H), 7.08 (d, J=2.1 Hz, 1H), 7.00 (d, J=9.0 Hz, 2H), 6.98 (d, J=2.4 Hz, 1H), 6.71 (dd, J=8.7, 2.4 Hz, 1H), 6.44 (d, J=9.0 Hz, 1H), 6.26 (td, J=6.7, 1.2 Hz, 1H), 3.76 (s, 3H), 3.21-3.19 (m, 4H), 2.69 (t, J=7.4 Hz, 2H), 2.54-2.50 (m, 4H), 2.41 (t, J=7.1 Hz, 2H), 1.87-1.80 (m, 2H).

Example 51 1-(4-(4-(4-(5-methoxy-1H-indol-3-yl)butyl)piperazin-1-yl)phenyl)-4-methylpyridin-2(1H)-one

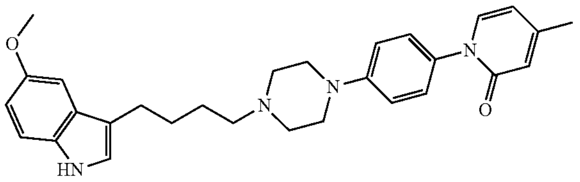 [SMILES: COc1ccc2[nH]cc(CCCCN3CCN(c4ccc(-n5ccc(C)cc5=O)cc4)CC3)c2c1]

The title compound was prepared by the procedure described in step 2 of example 1, using 4-methyl-1-(4-(piperazin-1-yl)phenyl)pyridin-2(1H)-one (0.16 g, 0.60 mmol), 4-(5-methoxy-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.11 g, 39.0%). The compound was characterized by the following spectroscopic data: MS (ESI, pos. ion) m/z: 471.1 $[M+H]^+$ and $^1H$ NMR (400 MHz, DMSO-$d_6$) δ (ppm): 10.56 (s, 1H), 7.46 (d, J=6.9 Hz, 1H), 7.21 (d, J=8.7 Hz, 1H), 7.17 (d, J=8.9 Hz, 1H), 7.06 (d, J=2.0 Hz, 1H), 7.02-6.97 (m, 3H), 6.70 (dd, J=8.7, 2.4 Hz, 2H), 6.25 (s, 1H), 6.12 (dd, J=7.0, 1.7 Hz, 1H), 3.75 (s, 3H), 3.16-3.11 (m, 4H), 2.67 (t, J=7.4 Hz, 2H), 2.48-2.46 (m, 4H), 2.37 (m, 2H), 2.16 (s, 3H), 1.69-1.64 (m, 2H), 1.56-1.52 (m, 2H).

Example 52 1-(4-(4-(3-(5-methoxy-1H-indol-3-yl)propyl)piperazin-1-yl)phenyl)-4-methylpyridin-2(1H)-one

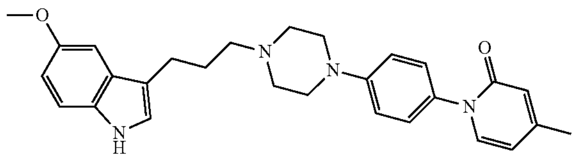

The title compound was prepared by the procedure described in step 2 of example 1, using 4-methyl-1-(4-(piperazin-1-yl)phenyl)pyridin-2(1H)-one (0.16 g, 0.60 mmol), 3-(5-methoxy-1H-indol-3-yl)propyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.12 g, 44.0%). The compound was characterized by the following spectroscopic data: MS (ESI, pos. ion) m/z: 457.1 $[M+H]^+$ and $^1H$ NMR (400 MHz, DMSO-$d_6$) δ (ppm): 10.58 (s, 1H), 7.45 (d, J=7.2 Hz, 1H), 7.22 (d, J=8.8 Hz, 1H), 7.18 (s, 1H), 7.16 (s, 1H), 7.08 (d, J=2.0 Hz, 1H), 7.00-6.97 (m, 3H), 6.71 (dd, J=8.8, 2.4 Hz, 1H), 6.25 (s, 1H), 6.13 (dd, J=7.2, 1.6 Hz, 1H), 3.76 (s, 3H), 3.19-3.18 (m, 4H), 2.69 (t, J=7.46 Hz, 2H), 2.55-2.52 (m, 4H), 2.44 (t, J=7.1 Hz, 2H), 2.16 (s, 3H), 1.87-1.82 (m, 2H).

Example 53 3-(4-(4-(4-(2-methyl-4-oxofuro[3,2-c]pyridin-5(4H)-yl)phenyl)piperazin-1-yl)butyl)-1H-indole-5-carbonitrile

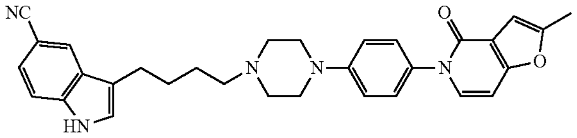 [SMILES: Cc1cc2c(=O)n(-c3ccc(N4CCN(CCCCc5c[nH]c6ccc(C#N)cc56)CC4)cc3)ccc2o1]

Step 1) 2-methyl-5-(4-(piperazin-1-yl)phenyl)furo[3,2-c]pyridin-4(5H)-one

The title compound was prepared by the procedure described in step 1 of example 1, using 5-(4-aminophenyl)-2-methylfuro[3,2-c]pyridin-4(5H)-one (2.40 g, 10.0 mmol), bis(2-chloroethyl)amine hydrochloride (1.96 g, 11.0 mmol) and potassium carbonate (1.5 g, 11.0 mmol) in n-butyl alcohol (20 mL) to give the crude product, which was purified by silica gel column chromatography ($CH_2Cl_2$/$CH_3OH$ (v/v)=20/1) to give the title compound as a white solid (1.70 g, 55.0%). The compound was characterized by the following spectroscopic data: MS (ESI, pos. ion) m/z: 310.1 $[M+H]^+$ and $^1H$ NMR (600 MHz, DMSO-$d_6$) δ (ppm): 7.45 (d, J=7.2 Hz, 1H), 7.27 (d, J=9.0 Hz, 2H), 7.13 (d, J=9.0 Hz, 2H), 6.72 (d, J=7.2 Hz, 1H), 6.59 (s, 1H), 3.51 (t, J=4.2 Hz, 4H), 3.22 (brs, 4H), 2.40 (s, 3H).

Step 2) 3-(4-(4-(4-(2-methyl-4-oxofuro[3,2-c]pyridin-5(4H)-yl)phenyl)piperazin-1-yl)butyl)-1H-indole-5-carbonitrile The title compound was prepared by the procedure described in step 2 of example 1, using 2-methyl-5-(4-(piperazin-1-yl)phenyl)furo[3,2-c]pyridin-4(5H)-one (0.19 g, 0.60 mmol), 4-(5-cyano-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.15 g, 50.0%). The compound was characterized by the following spectroscopic data: MS (ESI, pos. ion) m/z: 506.3 $[M+H]^+$ and $^1H$ NMR (600 MHz, $CD_3OD$/$CDCl_3$) δ (ppm): 7.90 (s, 1H), 7.37 (d, J=8.4 Hz, 1H), 7.33 (d, J=7.2 Hz, 1H), 7.21-7.18 (m, 3H), 7.08 (s, 1H), 6.95 (d, J=9.0 Hz, 2H), 6.59-6.57 (m, 2H), 3.24 (t, J=4.2 Hz, 4H), 2.76 (t, J=7.2 Hz, 2H), 2.63 (brs, 4H), 2.46-2.44 (m, 2H), 2.40 (s, 3H), 1.71-1.70 (m, 2H), 1.63-1.62 (m, 2H).

Example 54 3-(3-(4-(4-(2-methyl-4-oxofuro[3,2-c]pyridin-5(4H)-yl)phenyl)piperazin-1-yl)propyl)-1H-indole-5-carbonitrile

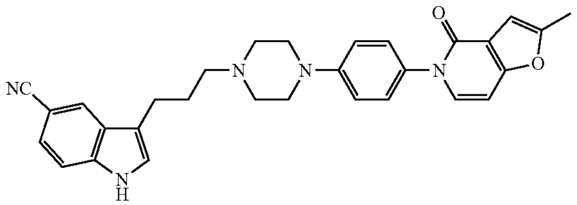 [SMILES: Cc1cc2c(=O)n(-c3ccc(N4CCN(CCCc5c[nH]c6ccc(C#N)cc56)CC4)cc3)ccc2o1]

The title compound was prepared by the procedure described in step 2 of example 1, using 2-methyl-5-(4-(piperazin-1-yl)phenyl)furo[3,2-c]pyridin-4(5H)-one (0.19 g, 0.60 mmol), 3-(5-cyano-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.17 g, 57.0%). The compound was characterized by the following spectroscopic data: MS (ESI, pos. ion) m/z: 492.2 $[M+H]^+$ and $^1H$ NMR (600 MHz, $CD_3OD$/$CDCl_3$) δ (ppm): 7.93 (s, 1H), 7.39 (d, J=8.4 Hz, 1H), 7.34 (d, J=10.8 Hz, 1H), 7.21-7.19 (m, 3H), 7.12 (s, 1H), 6.97 (d, J=8.4 Hz, 2H), 6.59-6.57 (m, 2H), 3.27 (brs, 4H), 2.78 (t, J=6.6 Hz, 2H), 2.67 (brs, 4H), 2.52 (brs, 2H), 2.41 (s, 3H), 1.97-1.96 (m, 2H).

Example 55 5-(4-(4-(4-(5-fluoro-1H-indol-3-yl)butyl)piperazin-1-yl)phenyl)-2-methylfuro[3,2-c]pyridin-4(5H)-one

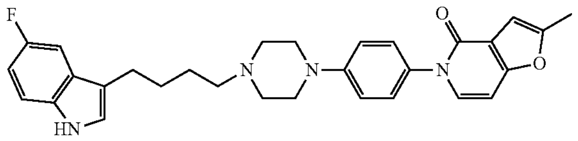 [SMILES: Cc1cc2c(=O)n(-c3ccc(N4CCN(CCCCc5c[nH]c6ccc(F)cc56)CC4)cc3)ccc2o1]

The title compound was prepared by the procedure described in step 2 of example 1, using 2-methyl-5-(4-(piperazin-1-yl)phenyl)furo[3,2-c]pyridin-4(5H)-one (0.19 g, 0.60 mmol), 4-(5-fluoro-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2$/$CH_3OH$ (v/v)=20/1) to give the title compound as a white solid (0.19 g, 65.0%). The compound was characterized by the following spectroscopic data: MS (ESI, pos. ion) m/z: 499.2 $[M+H]^+$ and $^1H$ NMR (400 MHz, $CD_3OD$/$CDCl_3$) δ (ppm): 7.33 (s, 1H), 7.28-7.20 (m, 4H), 7.05 (s, 1H), 6.99 (d, J=8.8 Hz, 2H), 6.90 (td, J=9.2, 2.0 Hz, 1H), 6.61-6.59 (m, 2H), 3.29 (brs, 4H), 2.77-2.74 (m, 2H), 2.69 (brs, 4H), 2.51-2.50 (m, 2H), 2.44 (s, 3H), 1.74-1.67 (m, 4H).

Example 56 5-(4-(4-(3-(5-fluoro-1H-indol-3-yl)propyl)piperazin-1-yl)phenyl)-2-methylfuro[3,2-c]pyridin-4(5H)-one

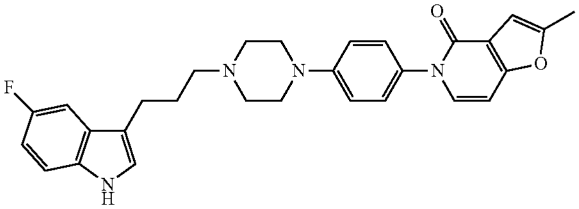 [SMILES: Cc1cc2c(=O)n(-c3ccc(N4CCN(CCCc5c[nH]c6ccc(F)cc56)CC4)cc3)ccc2o1]

The title compound was prepared by the procedure described in step 2 of example 1, using 2-methyl-5-(4-(piperazin-1-yl)phenyl)furo[3,2-c]pyridin-4(5H)-one (0.19 g, 0.60 mmol), 3-(5-fluoro-1H-indol-3-yl)propyl 4-methylbenzenesulfonate (0.21 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.20 g, 69.0%). The compound was characterized by the following spectroscopic data: MS (ESI, pos. ion) m/z: 485.2 $[M+H]^+$ and $^1H$ NMR (600 MHz, $CD_3OD/CDCl_3$) δ (ppm): 7.19-7.18 (m, 5H), 7.01 (s, 1H), 6.94 (d, J=7.2 Hz, 2H), 6.86-6.84 (m, 1H), 6.56-6.54 (m, 2H), 3.27 (brs, 4H), 2.72-2.70 (m, 2H), 2.62 (brs, 4H), 2.48-2.49 (m, 2H), 2.39 (s, 3H), 1.93-1.91 (m, 2H).

Example 57 5-(4-(4-(4-(5-methoxy-1H-indol-3-yl)butyl)piperazin-1-yl)phenyl)-2-methylfuro[3,2-c]pyridin-4(5H)-one

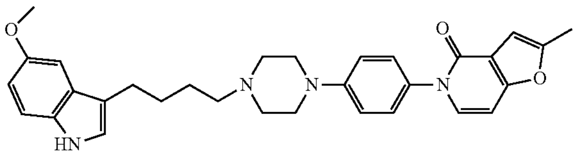 [SMILES: COc1ccc2[nH]cc(CCCCN3CCN(c4ccc(-n5ccc6oc(C)cc6c5=O)cc4)CC3)c2c1]

The title compound was prepared by the procedure described in step 2 of example 1, using 2-methyl-5-(4-(piperazin-1-yl)phenyl)furo[3,2-c]pyridin-4(5H)-one (0.19 g, 0.60 mmol), 4-(5-methoxy-1H-indol-3-yl)butyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.13 g, 43.0%). The compound was characterized by the following spectroscopic data: MS (ESI, pos. ion) m/z: 511.3 $[M+H]^+$ and $^1H$ NMR (400 MHz, $CD_3OD/CDCl_3$) δ (ppm): 7.21-7.24 (m, 3H), 7.18 (d, J=7.6 Hz, 1H), 7.02 (d, J=2.0 Hz, 1H), 6.97-6.95 (m, 3H), 6.82 (dd, J=8.8, 2.0 Hz, 1H), 6.59 (s, 1H), 6.56 (d, J=7.2 Hz, 1H), 3.86 (s, 3H), 3.27 (t, J=4.8 Hz, 4H), 2.75 (t, J=7.2 Hz, 2H), 2.66-2.65 (m, 4H), 2.52-2.47 (m, 2H), 2.42 (s, 3H), 1.74-1.66 (m, 4H).

Example 58 5-(4-(4-(3-(5-methoxy-1H-indol-3-yl)propyl)piperazin-1-yl)phenyl)-2-methylfuro[3,2-c]pyridin-4(5H)-one

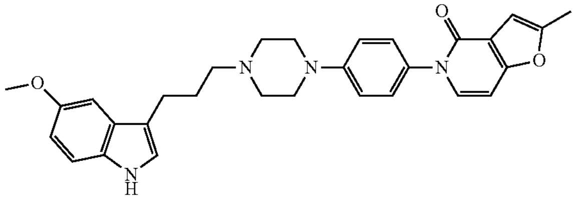

The title compound was prepared by the procedure described in step 2 of example 1, using 2-methyl-5-(4-(piperazin-1-yl)phenyl)furo[3,2-c]pyridin-4(5H)-one (0.19 g, 0.60 mmol), 3-(5-methoxy-1H-indol-3-yl)propyl 4-methylbenzenesulfonate (0.22 g, 0.60 mmol), potassium carbonate (0.12 g, 0.90 mmol) and potassium iodide (0.02 g, 0.12 mmol) in acetonitrile (10 mL) to give the crude product, which was purified by silica gel column chromatography ($CH_2Cl_2/CH_3OH$ (v/v)=20/1) to give the title compound as a white solid (0.12 g, 40.0%). The compound was characterized by the following spectroscopic data: MS (ESI, pos. ion) m/z: 497.3 $[M+H]^+$ and $^1H$ NMR (600 MHz, $CD_3OD/CDCl_3$) δ (ppm): 7.22-7.20 (m, 3H), 7.16 (d, J=7.2 Hz, 1H), 7.01 (d, J=2.4 Hz, 1H), 6.96-6.93 (m, 3H), 6.81 (dd, J=8.4, 2.4 Hz, 1H), 6.58 (s, 1H), 6.54 (d, J=7.8 Hz, 1H), 3.84 (s, 3H), 3.26 (t, J=4.8 Hz, 4H), 2.75 (t, J=7.2 Hz, 2H), 2.65 (t, J=4.8 Hz, 4H), 2.54 (t, J=5.2 Hz, 2H), 2.40 (s, 3H), 1.98-1.95 (m, 2H).

Example 59 methyl 6-(4-(4-(3-(5-cyano-1H-indol-3-yl)propyl)piperazin-1-yl)phenyl)-5-oxo-5,6-dihydro-1,6-naphthyridine-2-carboxylate

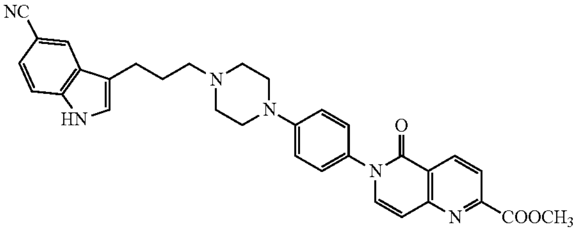 [SMILES: COC(=O)c1ccc2c(=O)n(-c3ccc(N4CCN(CCCc5c[nH]c6ccc(C#N)cc56)CC4)cc3)ccc2n1]

Step 1) methyl 5-oxo-6-(piperazin-1-yl)phenyl)-5,6-dihydro-1,6-naphthyridine-2-carboxylate The title compound was prepared by the procedure described in step 1 of example 1, using methyl 6-(4-aminophenyl)-5-oxo-5,6-dihydro-1,6-naphthyridine-2-carboxylate (3.01 g, 10.2 mmol), bis(2-chloroethyl)-amine hydrochloride (2.00 g, 11.2 mmol) and potassium carbonate (1.55 g, 11.2 mmol) in n-butyl alcohol (20 mL) to give the crude product, which was purified by silica gel column chromatography ($CH_2Cl_2/CH_3OH$ (v/v)=20/1) to give the title compound as a white solid (1.29 g, 34.8%). The compound was characterized by the following spectroscopic data: MS (ESI, pos. ion) m/z: 365.3 $[M+H]^+$ and $^1H$ NMR (400 MHz, DMSO-$d_6$) δ (ppm): 8.79 (d, J=8.8 Hz, 1H), 7.68 (d, J=7.6 Hz, 1H), 7.38 (d, J=8.8 Hz, 2H), 7.11 (d, J=8.8 Hz, 2H), 6.80 (d, J=7.6 Hz, 1H), 6.52 (d, J=7.6 Hz, 1H), 3.87 (s, 3H), 3.46 (t, J=4.8 Hz, 4H), 3.26 (t, J=4.8 Hz, 4H).

Step 2) methyl 6-(4-(4-(3-(5-cyano-1H-indol-3-yl)propyl)piperazin-1-yl)phenyl)-5-oxo-5,6-dihydro naphthyridine-2-carboxylate The title compound was prepared by the procedure described in step 2 of example 1, using methyl 5-oxo-6-(4-(piperazin-1-yl)phenyl)-5,6-dihydro-1,6-naphthyridine-2-carboxylate (0.29 g, 0.80 mmol), 3-(5-cyano-1H-indol-3-yl)propyl 4-methylbenzenesulfonate (0.28 g, 0.80 mmol), potassium carbonate (0.16 g, 1.20 mmol) and potassium iodide (0.03 g, 0.16 mmol) in acetonitrile (10 mL) to give the crude product, which was purified by silica gel column chromatography ($CH_2Cl_2/CH_3OH$ (v/v)=20/1) to give the title compound as a white solid (0.17 g, 39.1%). The compound was characterized by the following spectroscopic data: MS (ESI, pos. ion) m/z: 547.3 $[M+H]^+$ and $^1H$ NMR (400 MHz, $CDCl_3$) δ (ppm): 9.18 (s, 1H), 8.81 (d, J=9.0 Hz, 1H), 7.94 (s, 1H), 7.42-7.30 (m, 6H), 7.04 (s, 1H), 6.89 (d, J=9.0 Hz, 2H), 6.83 (d, J=7.8 Hz, 1H), 3.91 (s, 3H), 3.25 (t, J=4.8 Hz, 4H), 2.81 (t, J=4.8 Hz, 2H), 2.67 (t, J=4.8 Hz, 4H), 2.63 (t, J=4.6 Hz, 2H), 1.96-1.93 (m, 2H).

Example 60 6-(4-(4-(3-(5-cyano-1H-indol-3-yl)propyl)piperazin-1-yl)phenyl)-5-oxo-5,6-dihydro-1,6-naphthyridine-2-carboxylic acid

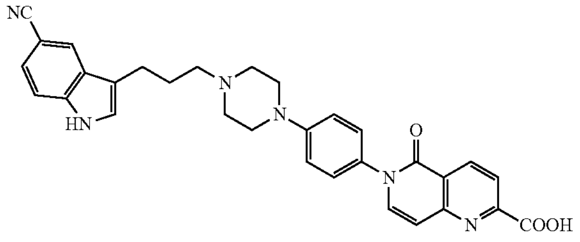 [SMILES: N#Cc1ccc2[nH]cc(CCCN3CCN(c4ccc(-n5ccc6nc(C(=O)O)ccc6c5=O)cc4)CC3)c2c1]

Step 1) 5-oxo-6-(4-(piperazin-1-yl)phenyl)-5,6-dihydro-1,6-naphthyridine-2-carboxylic acid The title compound was prepared by the procedure described in step 1 of example 1, using 6-(4-aminophenyl)-5-oxo-5,6-dihydro-1,6-naphthyridine-2-carboxylic acid (2.51 g, 8.9 mmol), bis(2-chloroethyl)amine hydrochloride (1.75 g, 9.8 mmol) and potassium carbonate (1.36 g, 9.8 mmol) in n-butyl alcohol (20 mL) to give the crude product, which was purified by silica gel column chromatography ($CH_2Cl_2$/$CH_3OH$ (v/v)=20/1) to give the title compound as a white solid (0.91 g, 29.1%). The compound was characterized by the following spectroscopic data: MS (ESI, pos. ion) m/z: 351.2 $[M+H]^+$ and $^1H$ NMR (400 MHz, DMSO-$d_6$) δ (ppm): 10.08 (s, 1H), 8.76 (d, J=8.8 Hz, 1H), 7.66 (d, J=7.6 Hz, 1H), 7.37 (d, J=8.8 Hz, 2H), 7.12 (d, J=8.8 Hz, 2H), 6.80 (d, J=7.6 Hz, 1H), 6.50 (d, J=7.6 Hz, 1H), 3.45 (t, J=4.8 Hz, 4H), 3.26 (t, J=4.8 Hz, 4H).

Step 2) 6-(4-(4-(3-(5-cyano-1H-indol-3-yl)propyl)piperazin-1-yl)phenyl)-5-oxo-5,6-dihydro-1,6-naphthyridine-2-carboxylic acid The title compound was prepared by the procedure described in step 2 of example 1, using 5-oxo-6-(4-(piperazin-1-yl)phenyl)-5,6-dihydro-1,6-naphthyridine-2-carboxylic acid (0.30 g, 0.86 mmol), 3-(5-cyano-1H-indol-3-yl)propyl 4-methylbenzenesulfonate (0.30 g, 0.86 mmol), potassium carbonate (0.18 g, 1.28 mmol) and potassium iodide (0.03 g, 0.16 mmol) in acetonitrile (10 mL) to give the crude product, which was purified by silica gel column chromatography ($CH_2Cl_2$/$CH_3OH$ (v/v)=20/1) to give the title compound as a white solid (0.14 g, 30.7%). The compound was characterized by the following spectroscopic data: MS (ESI, pos. ion) m/z: 533.3 $[M+H]^+$ and $^1H$ NMR (400 MHz, $CDCl_3$) δ (ppm): 10.01 (s, 1H), 9.24 (s, 1H), 8.83 (d, J=9.2 Hz, 1H), 7.95 (s, 1H), 7.43-7.32 (m, 6H), 7.06 (s, 1H), 6.87 (d, J=9.2 Hz, 2H), 6.84 (d, J=7.6 Hz, 1H), 3.24 (t, J=4.8 Hz, 4H), 2.80 (t, J=4.8 Hz, 2H), 2.69 (t, J=4.8 Hz, 4H), 2.64-2.62 (m, 2H), 1.96-1.92 (m, 2H).

Example 61 6-(4-(4-(3-(5-cyano-1H-indol-3-yl)propyl)piperazin-1-yl)phenyl)-5-oxo-5,6-dihydro-1,6-naphthyridine-2-carboxamide

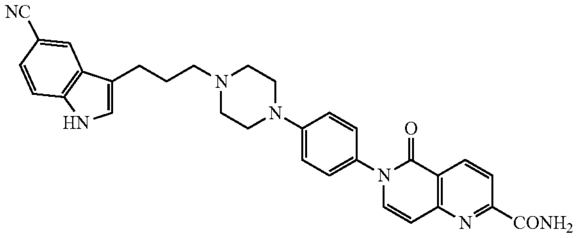 [SMILES: N#Cc1ccc2[nH]cc(CCCN3CCN(c4ccc(-n5ccc6nc(C(N)=O)ccc6c5=O)cc4)CC3)c2c1]

Step 1) 5-oxo-6-(4-(piperazin-1-yl)phenyl)-5,6-dihydro-1,6-naphthyridine-2-carboxamide The title compound was prepared by the procedure described in step 1 of example 1, using 6-(4-aminophenyl)-5-oxo-5,6-dihydro-1,6-naphthyridine-2-carboxamide (2.50 g, 8.9 mmol), bis(2-chloroethyl)-amine hydrochloride (1.75 g, 9.8 mmol) and potassium carbonate (1.36 g, 9.8 mmol) in n-butyl alcohol (20 mL) to give the crude product, which was purified by silica gel column chromatography ($CH_2Cl_2$/$CH_3OH$ (v/v)=20/1) to give the title compound as a white solid (1.10 g, 35.3%). The compound was characterized by the following spectroscopic data: MS (ESI, pos. ion) m/z: 350.2 $[M+H]^+$ and $^1H$ NMR (400 MHz, $CDCl_3$) δ (ppm): 8.78 (d, J=8.8 Hz, 1H), 7.65 (d, J=7.6 Hz, 1H), 7.40 (d, J=8.8 Hz, 2H), 7.10 (d, J=8.8 Hz, 2H), 6.79 (d, J=7.6 Hz, 1H), 6.51 (d, J=7.6 Hz, 1H), 3.44 (t, J=4.8 Hz, 4H), 3.25 (t, J=4.8 Hz, 4H).

Step 2) 6-(4-(4-(3-(5-cyano-1H-indol-3-yl)propyl)piperazin-1-yl)phenyl)-5-oxo-5,6-dihydro-1,6-naphthyridine-2-carboxamide The title compound was prepared by the procedure described in step 2 of example 1, using 5-oxo-6-(4-(piperazin-1-yl)phenyl)-5,6-dihydro-1,6-naphthyridine-2-carboxamide (0.30 g, 0.86 mmol), 3-(5-cyano-1H-indol-3-yl)propyl 4-methylbenzenesulfonate (0.30 g, 0.86 mmol), potassium carbonate (0.18 g, 1.28 mmol) and potassium iodide (0.03 g, 0.16 mmol) in acetonitrile (10 mL) to give the crude product, which was purified by silica gel column chromatography ($CH_2Cl_2$/$CH_3OH$ (v/v)=20/1) to give the title compound as a white solid (0.19 g, 41.6%). The compound was characterized by the following spectroscopic data: MS (ESI, pos. ion) m/z: 532.3 $[M+H]^+$ and $^1H$ NMR (400 MHz, $CDCl_3$) δ (ppm): 9.25 (s, 1H), 8.80 (d, J=9.2 Hz, 1H), 7.96 (s, 1H), 7.41-7.29 (m, 6H), 7.03 (s, 1H), 6.86 (d, J=9.2 Hz, 2H), 6.85 (d, J=7.8 Hz, 1H), 3.26 (t, J=4.8 Hz, 4H), 2.80 (t, J=4.8 Hz, 2H), 2.68 (t, J=4.8 Hz, 4H), 2.65 (t, J=4.8 Hz, 2H), 1.97-1.93 (m, 2H).

Example 62 methyl 2-((6-(4-(4-(3-(5-cyano-1H-indol-3-yl)propyl)piperazin-1-yl)-3-fluorophenyl)-5-oxo-5,6-dihydro-1,6-naphthyridin-2-yl)oxy)acetate

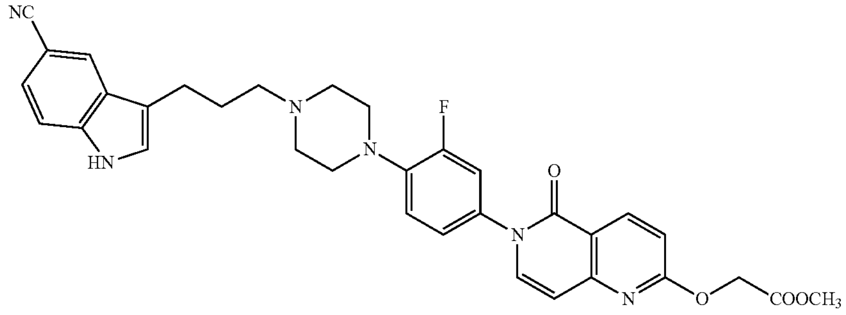 [SMILES: COC(=O)COc1ccc2c(=O)n(-c3ccc(N4CCN(CCCc5c[nH]c6ccc(C#N)cc56)CC4)c(F)c3)ccc2n1]

Step 1) methyl 2-((6-(3-fluoro-4-(piperazin-1-yl)phenyl)-5-oxo-5,6-dihydro-1,6-naphthyridin-2-yl)oxy)acetate The title compound was prepared by the procedure described in step 1 of example 1, using methyl 24(6-(4-amino-3-fluorophenyl)-5-oxo-5,6-dihydro-1,6-naphthyridin-2-yl)oxy)acetate (3.02 g, 8.8 mmol), bis(2-chloroethyl)amine hydrochloride (1.73 g, 9.7 mmol) and potassium carbonate (1.34 g, 9.7 mmol) in n-butyl alcohol (20 mL) to give the crude product, which was purified by silica gel column chromatography ($CH_2Cl_2/CH_3OH$ (v/v)=20/1) to give the title compound as a white solid (1.30 g, 35.8%). The compound was characterized by the following spectroscopic data: MS (ESI, pos. ion) m/z: 412.3 $[M+H]^+$ and $^1H$ NMR (400 MHz, DMSO-$d_6$) δ (ppm): 8.80 (d, J=8.8 Hz, 1H), 7.72 (dd, J=8.0, 1.6 Hz, 1H), 7.36 (d, J=8.8 Hz, 1H), 7.25 (d, J=7.6 Hz, 1H), 7.11 (d, J=8.8 Hz, 1H), 6.90 (dd, J=8.0, 1.6 Hz, 1H), 6.52 (d, J=7.6 Hz, 1H), 5.12 (s, 2H), 3.73 (s, 3H), 3.45 (t, J=4.8 Hz, 4H), 3.27 (t, J=4.8 Hz, 4H).

Step 2) methyl 2-((6-(4-(4-(3-(5-cyano-1H-indol-3-yl)propyl)piperazin-1-yl)-3-fluorophenyl)-5-oxo-5,6-dihydro-1,6-naphthyridin-2-yl)oxy)acetate The title compound was prepared by the procedure described in step 2 of example 1, using methyl 2-((6-(3-fluoro-4-(piperazin-1-yl)phenyl)-5-oxo-5,6-dihydro-1,6-naphthyridin-2-yl)oxy)acetate (0.30 g, 0.73 mmol), 3-(5-cyano-1H-indol-3-yl)propyl 4-methylbenzenesulfonate (0.26 g, 0.73 mmol), potassium carbonate (0.15 g, 1.09 mmol) and potassium iodide (0.02 g, 0.15 mmol) in acetonitrile (10 mL) to give the crude product, which was purified by silica gel column chromatography ($CH_2Cl_2/CH_3OH$ (v/v)=20/1) to give the title compound as a white solid (0.18 g, 41.6%). The compound was characterized by the following spectroscopic data: MS (ESI, pos. ion) m/z: 595.2 $[M+H]^+$ and $^1H$ NMR (400 MHz, $CDCl_3$) δ (ppm): 9.20 (s, 1H), 8.80 (d, J=9.2 Hz, 1H), 7.96 (s, 1H), 7.41-7.29 (m, 5H), 7.03 (s, 1H), 6.86 (dd, J=7.6, 1.6 Hz, 1H), 6.85-6.83 (m, 2H), 5.10 (s, 2H), 3.72 (s, 3H), 3.23 (t, J=4.8 Hz, 4H), 2.82 (t, J=4.8 Hz, 2H), 2.66 (t, J=4.8 Hz, 4H), 2.63 (t, J=4.8 Hz, 2H), 1.98-1.93 (m, 2H).

Example 63 2-((6-(4-(4-(3-(5-cyano-1H-indol-3-yl)propyl)piperazin-1-yl)-3-fluorophenyl)-5-oxo-5,6-dihydro-1,6-naphthyridin-2-yl)oxy)acetic acid

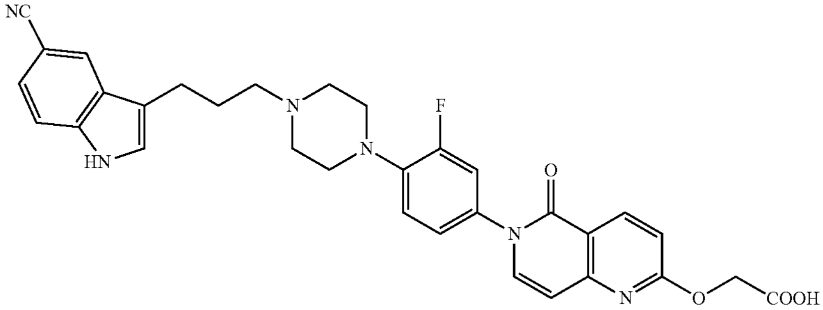 [SMILES: N#Cc1ccc2[nH]cc(CCCN3CCN(c4ccc(-n5ccc6nc(OCC(=O)O)ccc6c5=O)cc4F)CC3)c2c1]

Step 1) 2-((6-(3-fluoro-4-(piperazin-1-yl)phenyl)-5-oxo-5,6-dihydro-1,6-naphthyridin-2-yl)oxy)acetic acid The title compound was prepared by the procedure described in step 1 of example 1, using 24(6-(4-amino-3-fluorophenyl)-5-oxo-5,6-dihydro-1,6-naphthyridin-2-yl)oxy)acetic acid (2.93 g, 9.0 mmol), bis(2-chloroethyl)amine hydrochloride (1.76 g, 9.9 mmol) and potassium carbonate (1.37 g, 9.9 mmol) in n-butyl alcohol (20 mL) to give the crude product, which was purified by silica gel column chromatography ($CH_2Cl_2/CH_3OH$ (v/v)=20/1) to give the title compound as a white solid (1.02 g, 28.5%). The compound was characterized by the following spectroscopic data: MS (ESI, pos. ion) m/z: 399.2 $[M+H]^+$ and $^1H$ NMR (400 MHz, DMSO-$d_6$) δ (ppm): 11.03 (s, 1H), 8.81 (d, J=8.8 Hz, 1H), 7.74 (dd, J=8.0, 1.6 Hz, 1H), 7.34 (d, J=8.8 Hz, 1H), 7.24 (d, J=7.6 Hz, 1H), 7.12 (d, J=8.8 Hz, 1H), 6.91

(dd, J=8.0, 1.6 Hz, 1H), 6.50 (d, J=7.6 Hz, 1H), 5.10 (s, 2H), 3.47 (t, J=4.8 Hz, 4H), 3.26 (t, J=4.8 Hz, 4H).

Step 2) 2-((6-(4-(4-(3-(5-cyano-1H-indol-3-yl)propyl)piperazin-1-yl)-3-fluorophenyl)-5-oxo-5,6-dihydro-1,6-naphthyridin-2-yl)oxy)acetic acid The title compound was prepared by the procedure described in step 2 of example 1, using 2-((6-(3-fluoro-4-(piperazin-1-yl)phenyl)-5-oxo-5,6-dihydro-1,6-naphthyridin-2-yl)oxy)acetic acid (0.30 g, 0.75 mmol), 3-(5-cyano-1H-indol-3-yl)propyl 4-methylbenzenesulfonate (0.27 g, 0.75 mmol), potassium carbonate (0.16 g, 1.13 mmol) and potassium iodide (0.03 g, 0.16 mmol) in acetonitrile (10 mL) to give the crude product, which was purified by silica gel column chromatography ($CH_2Cl_2$/$CH_3OH$ (v/v)=20/1) to give the title compound as a white solid (0.12 g, 27.5%). The compound was characterized by the following spectroscopic data: MS (ESI, pos. ion) m/z: 581.2 $[M+H]^+$ and $^1H$ NMR (400 MHz, $CDCl_3$) δ (ppm): 11.10 (s, 1H), 9.26 (s, 1H), 8.79 (d, J=9.2 Hz, 1H), 7.95 (s, 1H), 7.45-7.29 (m, 5H), 7.02 (s, 1H), 6.87 (dd, J=7.6, 1.6 Hz, 1H), 6.85-6.84 (m, 2H), 5.08 (s, 2H), 3.25 (t, J=4.8 Hz, 4H), 2.80 (t, J=4.8 Hz, 2H), 2.67 (brs, 4H), 2.65 (t, J=4.8 Hz, 2H), 1.99-1.93 (m, 2H).

Example 64 2-((6-(4-(4-(3-(5-cyano-1H-indol-3-yl)propyl)piperazin-1-yl)-3-fluorophenyl)-5-oxo-5,6-dihydro-1,6-naphthyridin-2-yl)oxy)acetamide

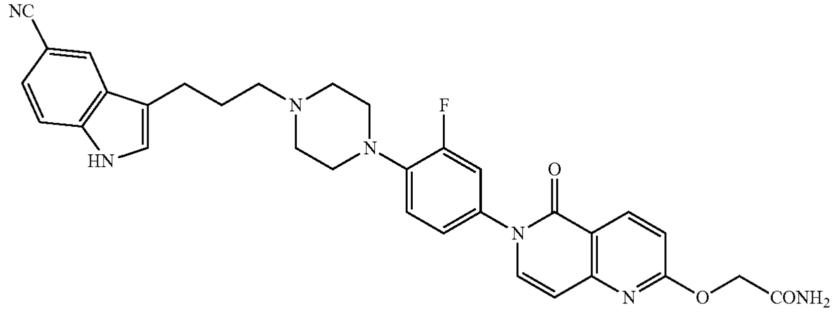 [SMILES: N#Cc1ccc2[nH]cc(CCCN3CCN(c4ccc(-n5ccc6nc(OCC(N)=O)ccc6c5=O)cc4F)CC3)c2c1]

Step 1) 2-((6-(3-fluoro-4-(piperazin-1-yl)phenyl)-5-oxo-5,6-dihydro-1,6-naphthyridin-2-yl)oxy)acetamide The title compound was prepared by the procedure described in step 1 of example 1, using 2-((6-(4-amino-3-fluorophenyl)-5-oxo-5,6-dihydro-1,6-naphthyridin-2-yl)oxy)acetamide (3.00 g, 9.1 mmol), bis(2-chloroethyl)amine hydrochloride (1.79 g, 10.1 mmol) and potassium carbonate (1.39 g, 10.1 mmol) in n-butyl alcohol (20 mL) to give the crude product, which was purified by silica gel column chromatography ($CH_2Cl_2$/$CH_3OH$ (v/v)=20/1) to give the title compound as a white solid (1.46 g, 40.2%). The compound was characterized by the following spectroscopic data: MS (ESI, pos. ion) m/z: 398.2 $[M+H]^+$ and $^1H$ NMR (400 MHz, DMSO-$d_6$) δ (ppm): 8.82 (d, J=8.8 Hz, 1H), 7.73 (dd, J=8.0, 1.6 Hz, 1H), 7.34 (d, J=8.8 Hz, 1H), 7.23 (d, J=7.6 Hz, 1H), 7.10 (d, J=8.8 Hz, 1H), 6.89 (dd, J=8.0, 1.6 Hz, 1H), 6.51 (d, J=7.6 Hz, 1H), 4.80 (s, 2H), 3.48 (t, J=4.8 Hz, 4H), 3.25 (t, J=4.8 Hz, 4H).

Step 2) 2-((6-(4-(4-(3-(5-cyano-1H-indol-3-yl)propyl)piperazin-1-yl)-3-fluorophenyl)-5-oxo-5,6-dihydro-1,6-naphthyridin-2-yl)oxy)acetamide The title compound was prepared by the procedure described in step 2 of example 1, using 2-((6-(3-fluoro-4-(piperazin-1-yl)phenyl)-5-oxo-5,6-dihydro-1,6-naphthyridin-2-yl)oxy)acetamide (0.30 g, 0.75 mmol), 3-(5-cyano-1H-indol-3-yl)propyl 4-methylbenzenesulfonate (0.27 g, 0.75 mmol), potassium carbonate (0.16 g, 1.13 mmol) and potassium iodide (0.03 g, 0.16 mmol) in acetonitrile (10 mL) to give the crude product, which was purified by silica gel column chromatography ($CH_2Cl_2$/$CH_3OH$ (v/v)=20/1) to give the title compound as a white solid (0.18 g, 41.1%). The compound was characterized by the following spectroscopic data: MS (ESI, pos. ion) m/z: 580.2 $[M+H]^+$ and $^1H$ NMR (400 MHz, $CDCl_3$) δ (ppm): 9.31 (s, 1H), 8.78 (d, J=9.2 Hz, 1H), 7.94 (s, 1H), 7.43-7.30 (m, 5H), 7.01 (s, 1H), 6.85 (dd, J=7.6, 1.6 Hz, 1H), 6.84-6.82 (m, 2H), 4.78 (s, 2H), 3.25 (brs, 4H), 2.83 (t, J=4.8 Hz, 2H), 2.68 (t, J=4.8 Hz, 4H), 2.63 (t, J=4.8 Hz, 2H), 1.97-1.94 (m, 2H).

Biological Test

The LC/MS/MS system used in analysis consists of Agilent 1200 Series vacuum degasser, binary syringe pump, well-plate autosampler, column oven, Agilent G6430 triple quadrupole mass spectrometer equipped with electrospray ionization (ESI) source. Quantitative analysis was performed in the MRM mode, and the MRM transition parameters were showed in Table A:

TABLE A

| | |
|---|---|
| Multiple reaction monitoring scan | 490.2→383.1 |
| Fragmentation voltage | 230 V |
| Capillary voltage | 55 V |
| Dryer temperature | 350° C. |
| Nebulizer | 40 psi |
| Dryer flow rate | 10 L/min |

Agilent XDB-C18 column (2.1×30 mm, 3.5 μM) was used in analysis, and the injection volume was 5 μL. The mobile phase was 0.1% formic acid in ultrapure water (phase A) and 0.1% formic acid in methanol (phase B). The flow rate was 0.4 mL/min. The mobile phase gradient was shown in Table B:

TABLE B

| Time (min) | Gradient of mobile phase B |
|---|---|
| 0.5 min | 5% |
| 1.0 min | 95% |

TABLE B-continued

| Time (min) | Gradient of mobile phase B |
|---|---|
| 2.2 min | 95% |
| 2.3 min | 5% |
| 5.0 min | stop |

In addition, the Agilent 6330 Series LC/MS/MS spectrometer was also used in analysis, which was equipped with G1312A binary syringe pump, G1367A autosampler and G1314C UV detector, and an ESI radioactive source was used on the LC/MS/MS spectrometer. Each analyte was treated with suitable cation model and optimal MRM conversion analysis by using standard solution. Capcell MP-C18 column (100×4.6 mm, 5 μM, Phenomenex, Torrance, Calif., USA) was applied in analysis. The mobile phase was phase A of 5 mM ammonium acetate and 0.1% methanol in ultrapure water, and phase B of 5 mM ammonium acetate and 0.1% methanol in acetonitrile (phase A/phase B (v/v)=70/30). The flow rate was 0.6 mL/min. Column was operated at room temperature, and the injection volume was 20 μL.

Example A: Evaluation of the Inhibitory Effect on [$^3$H]5-HT Uptake in Rat Synaptosome Test Method The synaptosomes (150 μg) prepared from a rat brain were incubated at 37° C. for 15 minutes with 0.1 μCi [$^3$H]5-HT in the absence or presence of the test compound or the reference compound in a buffer solution containing 106.2 mM NaCl, 4.5 mM KCl, 2.25 mM $MgSO_4$, 1.08 mM $NaH_2PO_4$, 22.5 mM $NaHCO_3$, 9.9 mM glucose, 9 μM EGTA and 45 μM ascorbic acid (pH 7.4).

The basal control activity was determined by incubating the same mixture at 4° C. for 15 minutes in the presence of 10 μM imipramine to block the uptake of 5-HT, which was taken as the standard reference compound and tested in each experiment at several concentrations to obtain an inhibition curve.

Following the incubation, the samples were filtered rapidly under vacuum through glass fiber filters (GF/B, Packard) and rinsed twice with an ice-cold incubation buffer using a 96-sample cell harvester (Unifilter, Packard) to eliminate free [$^3$H]5-HT. The filters were dried and the retained radioactivity was measured in a scintillation counter (Topcount, Packard) using a scintillation cocktail (Microscint 0, Packard). The experimental results were expressed as a percent inhibition of the control uptake of [$^3$H]5-HT.

Data Analysis

Inhibition of serotonin transporter in rat synaptosome was measured by the concentrations of [$^3$H]5-HT. The test compounds were required to be tested at least twice in the case of the concentration thereof being greater than 6 log, and the obtained data were subjected to a nonlinear regression analysis via a curve of Hill equation, to obtain $IC_{50}$ value. The experimental results of the compounds provided herein inhibiting [$^3$H]5-HT uptake in rat synaptosome were showed in Table 1.

TABLE 1

Inhibitory effect of the compounds provided herein on [$^3$H]5-HT uptake in rat synaptosome

| Example No. | $IC_{50}$ (nM) |
|---|---|
| 1 | 4.3 |
| 2 | 1.8 |

TABLE 1-continued

Inhibitory effect of the compounds provided herein on [$^3$H]5-HT uptake in rat synaptosome

| Example No. | $IC_{50}$ (nM) |
|---|---|
| 3 | 4.2 |
| 4 | 8.5 |
| 5 | 6.3 |
| 6 | 2.2 |
| 7 | 7.3 |
| 8 | 10 |
| 9 | 8.0 |
| 10 | 1.6 |
| 11 | 0.98 |
| 12 | 7.1 |
| 13 | 2.6 |
| 14 | 1.4 |
| 15 | 330 |
| 16 | 170 |
| 17 | 1.7 |
| 18 | 7.5 |
| 19 | 2.0 |
| 20 | 3.6 |
| 21 | 7.4 |
| 22 | 1.8 |
| 23 | 12 |
| 24 | 5.5 |
| 25 | 1.4 |
| 26 | 1.3 |
| 27 | 5.5 |
| 28 | 2.2 |
| 29 | 10 |
| 30 | 4.3 |
| 31 | 0.23 |
| 32 | 0.93 |
| 33 | 0.53 |
| 34 | 4.2 |
| 35 | 0.8 |
| 36 | 1.8 |
| 37 | 1.3 |
| 38 | 1.4 |

The experimental results indicated that the compounds provided herein exhibited potent inhibitory activity on [$^3$H]5-HT reuptake.

Example B: Evaluation of the Affinity for Human 5-$HT_{1A}$ Receptor

Test Method

Human HEK-293 cell homogenates (36 μg protein) were incubated at 22° C. for 60 minutes with 0.3 nM [$^3$H]8-0H-DPAT (Perkin-Elmer) in the absence or presence of the test compound in a buffer solution containing 50 mM Tris-HCl (pH 7.4), 10 mM $MgSO_4$, 0.5 mM EDTA and 2 μg/ml aprotinine.

The non-specific binding value was determined by incubating the same mixture in the presence of 10 μM 8-OH-DPAT, which was used as the standard reference compound and tested in each experiment at several concentrations to obtain a competition curve.

Following the incubation, the samples were filtered rapidly under vacuum through glass fiber filter (GF/B, Packard) presoaked with 0.3% PEI and rinsed several times with ice-cold 50 mM Tris-HCl using a 96-sample cell harvester (Unifilter, Packard). The filters were dried and the retained radioactivity was measured in a scintillation counter (Topcount, Packard) using a scintillation cocktail (Microscint 0, Packard). The experimental results were expressed as a percent inhibition of the control radioligand specific binding.

Data Analysis

Binding assay of [$^3$H] 8-OH-DPAT (0.3 nM) with 5-$HT_{1A}$ receptor in human HEK-293 cell was tested by scintillation proximity assay of membrane. The test compounds were required to be tested at least three times in the case of the concentration thereof being greater than 6 log, and the obtained data were subjected to a nonlinear regression analysis via a curve of Hill equation, to obtain $IC_{50}$ value, and then calculated by ChengPrusoff equation to obtain Ki value, and Ki was the inhibition constant. The experimental results of the binding affinity of the compounds provided herein for 5-$HT_{1A}$ receptor were showed in Table 2.

TABLE 2

Binding affinity of the compounds provided herein for 5-$HT_{1A}$ receptor

| Example No. | $K_i$ (nM) |
|---|---|
| 1 | 2.5 |
| 2 | 1.9 |
| 3 | 3.2 |
| 4 | 1.2 |
| 5 | 3.1 |
| 6 | 2.1 |
| 7 | 6.4 |
| 8 | 3.2 |
| 9 | 0.23 |
| 10 | 0.19 |
| 11 | 1.2 |
| 12 | 0.87 |
| 13 | 54 |
| 14 | 4.1 |
| 17 | 0.48 |
| 18 | 0.89 |
| 19 | 33 |
| 20 | 4.7 |
| 21 | 1.2 |
| 22 | 0.61 |
| 24 | 12 |
| 25 | 0.18 |
| 26 | 0.31 |
| 27 | 68 |
| 28 | 1.5 |
| 30 | 3.6 |
| 31 | 0.5 |
| 32 | 1.7 |
| 33 | 0.14 |
| 34 | 0.1 |
| 35 | 0.8 |
| 36 | 3.0 |
| 37 | 1.3 |
| 38 | 1.9 |

The experimental results indicated that the compounds disclosed herein exhibited high binding affinity for 5-$HT_{1A}$ receptor.

Reference throughout this specification to "one embodiment", "an embodiment", "some embodiments", "explanatory embodiment", "an example", "a specific example" or "some examples", means that a particular feature, structure, material or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific examples", or "in some examples" in various places throughout this specification are not necessarily referring to the same embodiment or example of the present disclosure. Furthermore, the particular features, structures, materials or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

What is claimed is:

1. A compound having Formula (I) or a stereoisomer, a tautomer, an N-oxide, a solvate, a metabolite, a pharmaceutically acceptable salt or a prodrug thereof, (I)

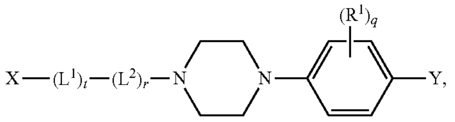

wherein

X is

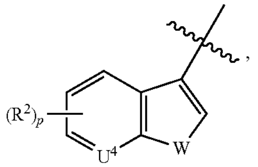

wherein $U^4$ is $CR^2$ or N;

p is 1, 2 or 3;

W is —NH—, —O— or —S—;

each $L^1$ is —$CR^3R^4$—;

each $L^2$ is —$CR^5R^6$—;

t is 0, 1 or 2;

r is 1, 2, 3, 4 or 5;

q is 1, 2, 3 or 4;

Y is

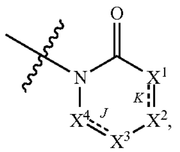

wherein Q is O, S or N($R^7$);

each of $\overset{J}{\equiv}$ and $\overset{K}{\equiv}$ is independently a single bond or a double bond;

each of $X^1$, $X^2$, $X^3$ and $X^4$ is independently —O—, —S—, $CR^8$, N, —$CR^8R^{8a}$— or —$NR^{8b}$—;

or $X^1$ and $X^2$ together or $X^3$ and $X^4$ together independently form —$CR^8R^{8a}$—, —$NR^{8b}$—, —O— or —S—;

each $R^1$ is independently H, D, F, Cl, Br, I, —CN, —$N_3$, —$NO_2$, —$NR^aR^b$, —$OR^c$, alkyl, alkenyl or alkynyl, wherein each of alkyl, alkenyl and alkynyl is optionally and independently substituted with one or more $R^9$;

each $R^2$ is independently H, D, F, Cl, Br, I, —CN, —$N_3$, —$NO_2$, —$NR^aR^b$, —$OR^c$, —$S(=O)_mR^c$, —C(=O)$R^c$, —C(=O)$OR^c$, —C(=O)$NR^aR^b$, —S(=O)$_2$NR$^a$R$^b$, —OC(=O)R$^c$, —N(R$^a$)C(=O)R$^c$, alkyl, alkenyl or alkynyl, wherein each of alkyl, alkenyl and alkynyl is optionally and independently substituted with one or more R$^9$;

each R$^3$ and R$^4$ is independently H, D, F, Cl, Br, I, —CN, —N$_3$, —NH$_2$, —OH, alkyl, alkenyl, alkynyl, alkoxy, alkylamino, cycloalkyl, heterocyclyl, aryl or heteroaryl, or R$^3$ and R$^4$, together with the carbon atom to which they are attached, form a carbonyl group, a carbocyclic ring or a heterocyclic ring, wherein each of alkyl, alkenyl, alkynyl, alkoxy, alkylamino, cycloalkyl, heterocyclyl, aryl, heteroaryl, the carbocyclic ring and the heterocyclic ring is optionally and independently substituted with one or more R$^9$;

each R$^5$ and R$^6$ is independently H, D, F, Cl, Br, I, —CN, —N$_3$, —NH$_2$, —OH, alkyl, alkenyl, alkynyl, alkoxy, alkylamino, cycloalkyl, heterocyclyl, aryl or heteroaryl, or R$^5$ and R$^6$, together with the carbon atom to which they are attached, form a carbocyclic ring or a heterocyclic ring, wherein each of alkyl, alkenyl, alkynyl, alkoxy, alkylamino, cycloalkyl, heterocyclyl, aryl, heteroaryl, the carbocyclic ring and the heterocyclic ring is optionally and independently substituted with one or more R$^9$;

R$^7$ is H, —OH, —NH$_2$, C$_1$-C$_4$ alkyl, C$_1$-C$_4$ haloalkyl or C$_1$-C$_4$ alkylamino;

each R$^8$, R$^{8a}$ and R$^{8b}$ is independently H, D, F, Cl, Br, I, —CN, —N$_3$, —NO$_2$, —(C$_0$-C$_6$ alkylene)-NR$^a$R$^b$, —(C$_0$-C$_6$ alkylene)-OR$^c$, —(C$_0$-C$_6$ alkylene)-S(=O)$_m$R$^c$, —C(=O)R$^c$, —C(=O)OR$^c$, —C(=O)NR$^a$R$^b$, —S(=O)$_2$NR$^a$R$^b$, —OC(=O)R$^c$, —N(R$^a$)C(=O)R$^c$, alkyl, alkenyl, alkynyl, cycloalkyl, heterocyclyl, aryl or heteroaryl;

or two R$^8$ on two adjacent ring atoms, or two R$^{8b}$ on two adjacent ring atoms, or R$^8$ and R$^{8b}$ on two adjacent ring atoms, together with the ring atoms to which they are attached, independently form a carbocyclic ring, a heterocyclic ring, an aryl ring or a heteroaryl ring, wherein each of the carbocyclic ring, the heterocyclic ring, the aryl ring and the heteroaryl ring is optionally and independently substituted with one or more substituents independently selected from R$^x$ and R$^y$;

each R$^9$ is independently F, Cl, Br, I, —CN, —N$_3$, —NO$_2$, —OH, —SH, —NH$_2$, alkyl, haloalkyl, alkoxy, alkylthio or alkylamino;

each R$^x$ and R$^y$ is independently H, D, F, Cl, Br, I, —CN, —N$_3$, —NO$_2$, —NR$^a$R$^b$, —OR$^c$, —SR$^c$, —C(=O)NR$^a$R$^b$, —C(=O)OR$^c$, —O—(C$_0$-C$_6$ alkylnene)-C(=O)NR$^a$R$^b$, —O—(C$_0$-C$_6$ alkylene)-C(=O)OR$^c$, alkyl or haloalkyl;

each R$^a$ and R$^b$ is independently H, alkyl, alkenyl, alkynyl, haloalkyl, —(C$_0$-C$_6$ alkylene)-cycloalkyl, —(C$_0$-C$_6$ alkylene)-heterocyclyl, —(C$_0$-C$_6$ alkylene)-aryl or —(C$_0$-C$_6$ alkylene)-heteroaryl, or R$^a$ and R$^b$, together with the nitrogen atom to which they are attached, form a heterocyclic ring;

each R$^c$ is independently H, alkyl, alkenyl, alkynyl, haloalkyl, —(C$_0$-C$_6$ alkylene)-cycloalkyl, —(C$_0$-C$_6$ alkylene)-heterocyclyl, —(C$_0$-C$_6$ alkylene)-aryl or —(C$_0$-C$_6$ alkylene)-heteroaryl; and each m is independently 0, 1 or 2.

2. The compound according to claim 1, wherein each R$^1$ is independently H, D, F, Cl, Br, I, —CN, —N$_3$, —NO$_2$, —NR$^a$R$^b$, —OR$^c$, C$_1$-C$_6$ alkyl, C$_2$-C$_6$ alkenyl or C$_2$-C$_6$ alkynyl, wherein each of C$_1$-C$_6$ alkyl, C$_2$-C$_6$ alkenyl and C$_2$-C$_6$ alkynyl is optionally and independently substituted with one or more R$^9$; or each R$^1$ is independently H, D, F, Cl, Br, —CN, —NO$_2$, —OR$^c$ or C$_1$-C$_4$ alkyl, wherein the C$_1$-C$_4$ alkyl is optionally substituted with one or more R$^9$;

each R$^2$ is independently H, D, F, Cl, Br, I, —CN, —N$_3$, —NO$_2$, —NR$^a$R$^b$, —OR$^c$, —S(=O)$_m$R$^c$, —C(=O)R$^c$, —C(=O)OR$^c$, —C(=O)NR$^a$R$^b$, —S(=O)$_2$NR$^a$R$^b$, —OC(=O)R$^c$, —N(R$^a$)C(=O)R$^c$, C$_1$-C$_6$ alkyl, C$_2$-C$_6$ alkenyl or C$_2$-C$_6$ alkynyl, wherein each of C$_1$-C$_6$ alkyl, C$_2$-C$_6$ alkenyl and C$_2$-C$_6$ alkynyl is optionally and independently substituted with one or more R$^9$; or each R$^2$ is independently H, D, F, Cl, Br, —CN, —NO$_2$, —NR$^a$R$^b$, —OR$^c$, —C(=O)OR$^c$, —C(=O)NR$^a$R$^b$ or C$_1$-C$_4$ alkyl, wherein the C$_1$-C$_4$ alkyl is optionally substituted with one or more R$^9$;

each R$^3$ and R$^4$ is independently H, D, F, Cl, Br, I, —CN, —N$_3$, —NH$_2$, —OH, C$_1$-C$_6$ alkyl, C$_2$-C$_6$ alkenyl, C$_2$-C$_6$ alkynyl, C$_1$-C$_6$ alkoxy, C$_1$-C$_6$ alkylamino, C$_3$-C$_{10}$ cycloalkyl, 3-10 membered heterocyclyl, C$_6$-C$_{10}$ aryl or 5-10 membered heteroaryl, or R$^3$ and R$^4$, together with the carbon atom to which they are attached, form a carbonyl group, a C$_3$-C$_8$ carbocyclic ring or a 3-7 membered heterocyclic ring, wherein each of C$_1$-C$_6$ alkyl, C$_2$-C$_6$ alkenyl, C$_2$-C$_6$ alkynyl, C$_1$-C$_6$ alkoxy, C$_1$-C$_6$ alkylamino, C$_3$-C$_{10}$ cycloalkyl, 3-10 membered heterocyclyl, C$_6$-C$_{10}$ aryl, 5-10 membered heteroaryl, the C$_3$-C$_8$ carbocyclic ring and the 3-7 membered heterocyclic ring is optionally and independently substituted with one or more R$^9$;

each R$^5$ and R$^6$ is independently H, D, F, Cl, Br, I, —CN, —N$_3$, —NH$_2$, —OH, C$_1$-C$_6$ alkyl, C$_2$-C$_6$ alkenyl, C$_2$-C$_6$ alkynyl, C$_1$-C$_6$ alkoxy, C$_1$-C$_6$ alkylamino, C$_3$-C$_{10}$ cycloalkyl, 3-10 membered heterocyclyl, C$_6$-C$_{10}$ aryl or 5-10 membered heteroaryl, or R$^5$ and R$^6$, together with the carbon atom to which they are attached, form a C$_3$-C$_8$ carbocyclic ring or a 3-7 membered heterocyclic ring, wherein each of C$_1$-C$_6$ alkyl, C$_2$-C$_6$ alkenyl, C$_2$-C$_6$ alkynyl, C$_1$-C$_6$ alkoxy, C$_1$-C$_6$ alkylamino, C$_3$-C$_{10}$ cycloalkyl, 3-10 membered heterocyclyl, C$_6$-C$_{10}$ aryl, 5-10 membered heteroaryl, C$_3$-C$_8$ carbocyclic ring and 3-7 membered heterocyclic ring is optionally and independently substituted with one or more R$^9$; and each R$^9$ is independently F, Cl, Br, I, —CN, —N$_3$, —NO$_2$, —OH, —SH, —NH$_2$, C$_1$-C$_6$ alkyl, C$_1$-C$_6$ haloalkyl, C$_1$-C$_6$ alkoxy, C$_1$-C$_6$ alkylthio or C$_1$-C$_6$ alkylamino.

3. The compound according to claim 1, wherein each R$^8$, R$^{8a}$, and R$^{8b}$ is independently H, D, F, Cl, Br, I, —CN, —N$_3$, —NO$_2$, —(C$_0$-C$_6$ alkylene)-NR$^a$R$^b$, —(C$_0$-C$_6$ alkylene)-OR$^c$, —(C$_0$-C$_6$ alkylene)-S(=O)$_m$R$^c$, —C(=O)R$^c$, —C(=O)OR$^c$, —C(=O)NR$^a$R$^b$, —S(=O)$_2$NR$^a$R$^b$, —OC(=O)R$^c$, —N(R$^a$)C(=O)R$^c$, C$_1$-C$_6$ alkyl, C$_2$-C$_6$ alkenyl, C$_2$-C$_6$ alkynyl, C$_3$-C$_{10}$ cycloalkyl, 3-10 membered heterocyclyl, C$_6$-C$_{10}$ aryl or 5-10 membered heteroaryl;

or two R$^8$ on two adjacent ring atoms, or two R$^{8b}$ on two adjacent ring atoms, or R$^8$ and R$^{8b}$ on two adjacent ring atoms, together with the ring atoms to which they are attached, independently form a C$_3$-C$_{10}$ carbocyclic ring, a 3-10 membered heterocyclic ring, a C$_6$-C$_{10}$ aryl ring or a 5-10 membered heteroaryl ring, wherein each of the C$_3$-C$_{10}$ carbocyclic ring, the 3-10 membered heterocyclic ring, the C$_6$-C$_{10}$ aryl ring and the 5-10 membered heteroaryl ring is optionally and independently substituted with one or more substituents independently selected from R$^x$ and R$^y$; or wherein each R$^8$, R$^{8a}$ and R$^{8b}$ is independently H, D, F, Cl, Br, —CN, —NO$_2$, —(C$_0$-C$_4$ alkylene)-OR$^c$, —(C$_0$-C$_4$ alkylene)-NR$^a$R$^b$, —C(=O)OR$^c$, —C(=O)NR$^a$R$^b$, C$_1$-C$_4$ alkyl, C$_2$-C$_4$ alkenyl or C$_2$-C$_4$ alkynyl;

or two $R^8$ on two adjacent ring atoms, or two $R^{8b}$ on two adjacent ring atoms, or $R^8$ and $R^{8b}$ on two adjacent ring atoms, together with the ring atoms to which they are attached, independently form a $C_3$-$C_8$ carbocyclic ring, a 3-7 membered heterocyclic ring, a benzene ring or a 5-6 membered heteroaryl ring, wherein each of the $C_3$-$C_8$ carbocyclic ring, the 3-7 membered heterocyclic ring, the benzene ring and the 5-6 membered heteroaryl ring is optionally and independently substituted with one or more substituents independently selected from $R^x$ and $R^y$.

4. The compound according to claim 1, wherein each $R^x$ and $R^y$ is independently H, D, F, Cl, Br, I, —CN, —$N_3$, —$NO_2$, —$NR^aR^b$, —$OR^c$, —$SR^c$, —C(═O)$NR^aR^b$, —C(═O)$OR^c$, —O—($C_0$-$C_6$ alkylnene)-C(═O)$NR^aR^b$, —O—($C_0$-$C_6$ alkylene)-C(═O)$OR^c$, $C_1$-$C_6$ alkyl or $C_1$-$C_6$ haloalkyl; or wherein each $R^x$ and $R^y$ is independently H, D, F, Cl, Br, —CN, —$NO_2$, —$NR^aR^b$, —$OR^c$, —$SR^c$, —C(═O)$NR^aR^b$, —C(═O)$OR^c$, —O—($C_0$-$C_4$ alkylnene)-C(═O)$NR^aR^b$, —O—($C_0$-$C_4$ alkylene)-C(═O)$OR^c$, $C_1$-$C_4$ alkyl or $C_1$-$C_4$ haloalkyl.

5. The compound according to claim 1 having Formula (II) or a stereoisomer, a tautomer, an N-oxide, a solvate, a metabolite, a pharmaceutically acceptable salt or a prodrug thereof, (II)

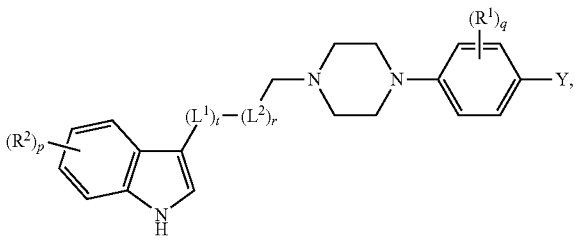

wherein p is 1, 2 or 3; and r is 1, 2, 3 or 4.

6. The compound according to claim 2, wherein each $R^1$ is independently H, D, F, Cl, Br, —CN, —$NO_2$, -Me, —$CF_3$ or —OMe; and each $R^2$ is independently H, D, F, Cl, Br, —CN, —$NO_2$, —$NH_2$, —$NMe_2$, —OH, —OMe, —O(i-Pr), -Me, -Et, -(i-Pr), —$CF_3$, —C(═O)OH, —C(═O)OMe or —$CONH_2$.

7. The compound according to claim 1, wherein each $L^1$ is —$CH_2$—, —C(═O)— or —CH(OH)—.

8. The compound according to claim 1, wherein Y is

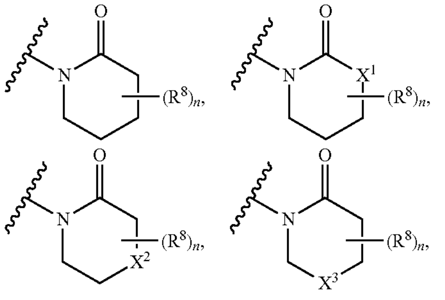

-continued

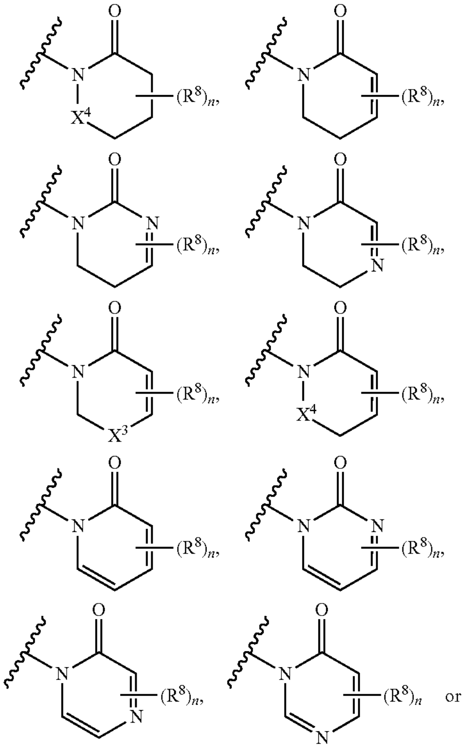

or

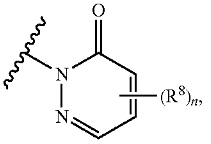

wherein each $X^1$, $X^2$, $X^3$ and $X^4$ is independently —O—, —S— or —$NR^{8b}$—; and each n is independently 1, 2, 3 or 4.

9. The compound according to claim 8, wherein Y is

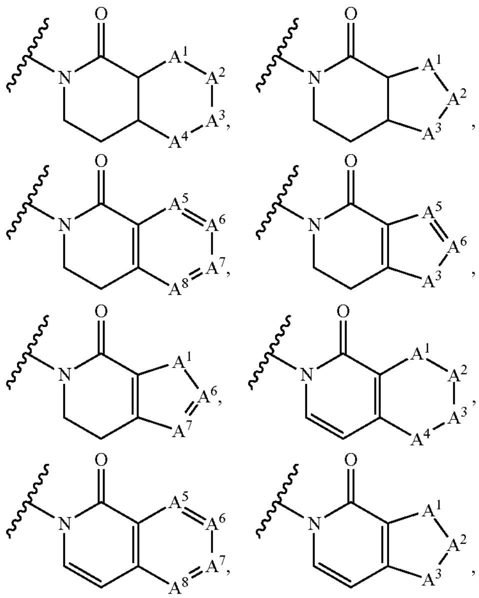

-continued

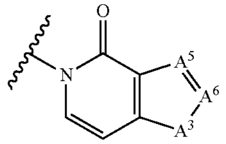

or

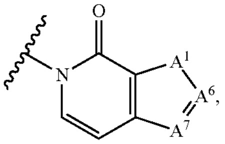

wherein each $A^1$, $A^2$, $A^3$ and $A^4$ is independently —O—, —S—, —$NR^y$— or —$CHR^x$—; and each $A^5$, $A^6$, $A^7$ and $A^8$ is independently N or $CR^x$.

10. The compound according to claim 3, wherein each $R^8$, $R^{8a}$ and $R^{8b}$ is independently H, D, F, Cl, Br, —CN, —$NO_2$, —OH, —$NH_2$, —C(═O)OMe, —C(═O)OEt, —C(═O)$NH_2$, -Me, -Et, -(i-Pr), —OMe, —O(i-Pr) or —$NMe_2$.

11. The compound according to claim 4, wherein each $R^x$ and $R^y$ is independently H, D, F, Cl, Br, —CN, —$NO_2$, —OH, —OMe, —$NH_2$, —$NMe_2$, —COOH, —C(═O)OMe, —C(═O)OEt, —C(═O)$NH_2$, —$OCH_2COOH$, —$OCH_2C$(═O)OMe, —$OCH_2C$(═O)OEt, —$OCH_2C$(═O)$NH_2$, -Me, -Et, -(i-Pr) or —$CF_3$.

12. The compound according to claim 1, wherein each $R^a$ and $R^b$ is independently H, $C_1$-$C_4$ alkyl, $C_2$-$C_4$ alkenyl, $C_2$-$C_4$ alkynyl, $C_1$-$C_4$ haloalkyl, —($C_0$-$C_4$ alkylene)-($C_3$-$C_8$ cycloalkyl), —($C_0$-$C_4$ alkylene)-(3-7 membered heterocyclyl), —($C_0$-$C_4$ alkylene)-(phenyl) or —($C_0$-$C_4$ alkylene)-(5-6 membered heteroaryl), or $R^a$ and $R^b$, together with the nitrogen atom to which they are attached, form a 3-7 membered heterocyclic ring; and each $R^c$ is independently H, $C_1$-$C_4$ alkyl, $C_2$-$C_4$ alkenyl, $C_2$-$C_4$ alkynyl, $C_1$-$C_4$ haloalkyl, —($C_0$-$C_4$ alkylene)-($C_3$-$C_8$ cycloalkyl), —($C_0$-$C_4$ alkylene)-(3-7 membered heterocyclyl), —($C_0$-$C_4$ alkylene)-(phenyl) or —($C_0$-$C_4$ alkylene)-(5-6 membered heteroaryl).

13. The compound according to claim 1 having one of the following structures:

(1)

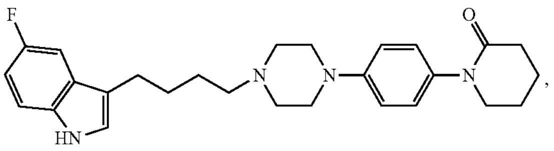

(2)

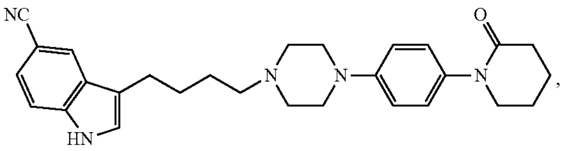

(3)

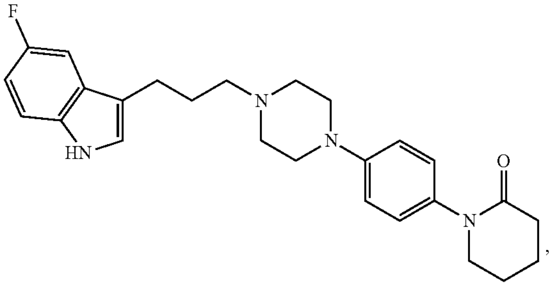

(4)

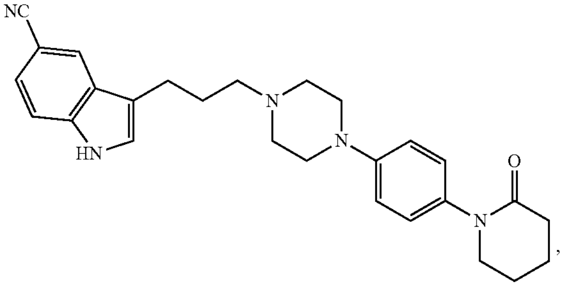

(5)

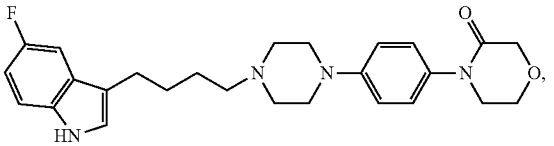

(6)

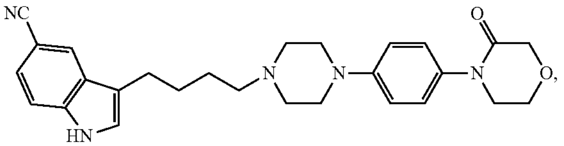

(7)

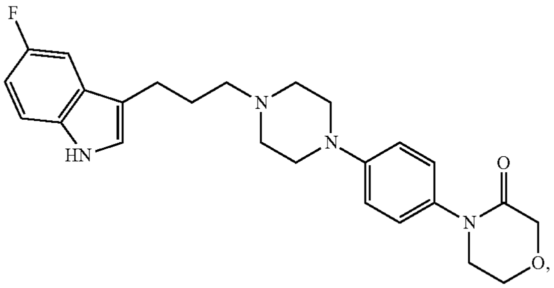

(8)

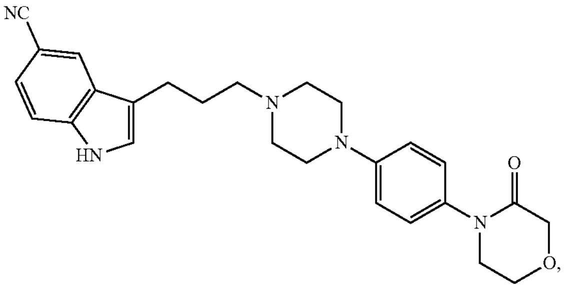

(9)

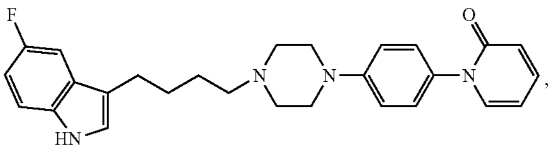

(10)

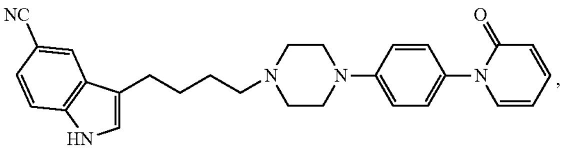

-continued
(11)
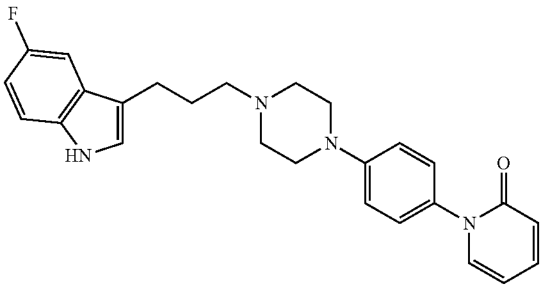
,
(12)
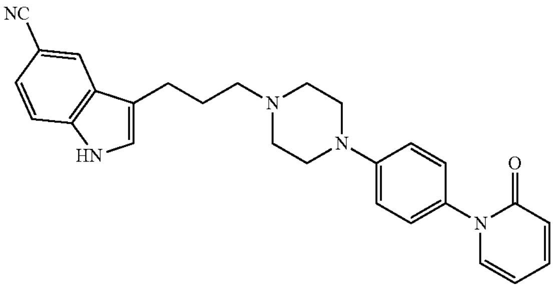
,
(13)
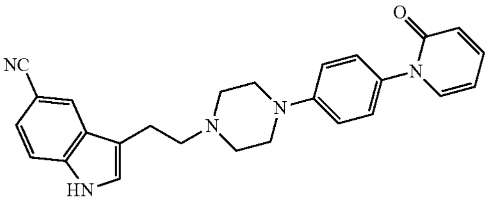
,
(14)
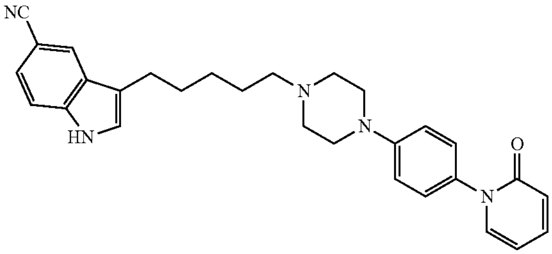
,
(15)
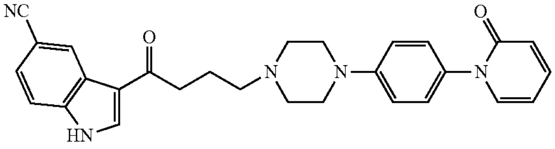
,
(16)
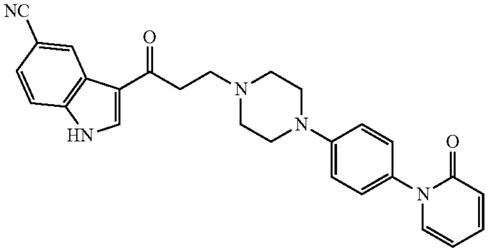
,
(17)
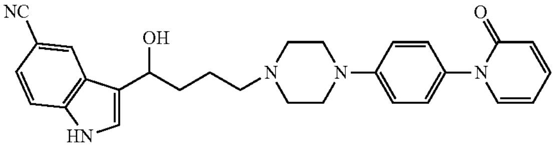
,
(18)
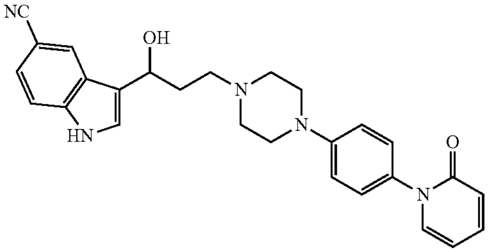
,
(19)
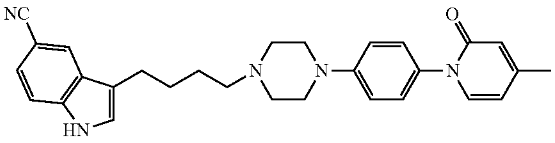
,
(20)
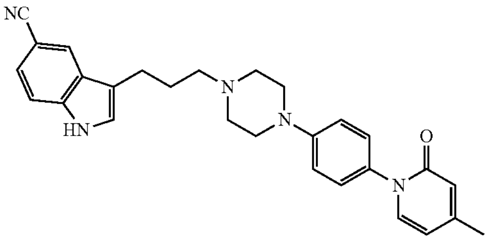
, -continued
(21)
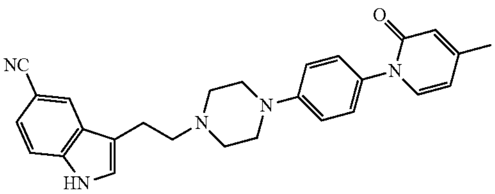
,
(22)
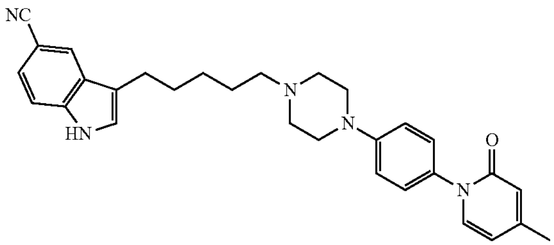
,
(23)
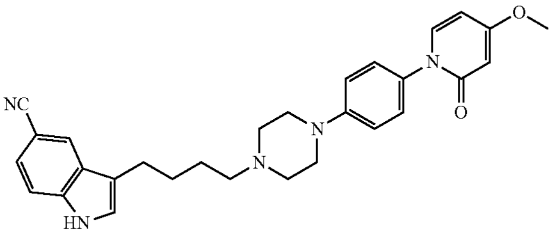
,
(24)
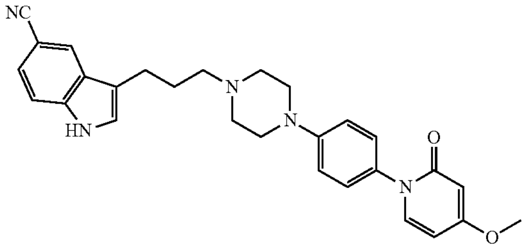
,
(25)
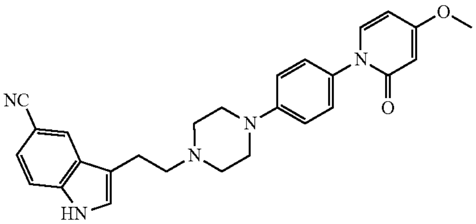
,
(26)
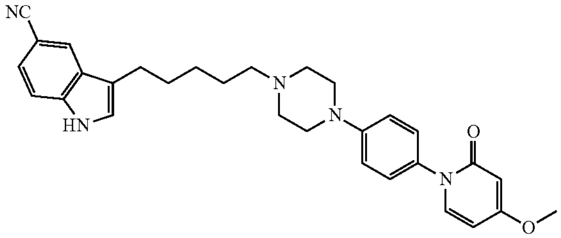
,
(27)
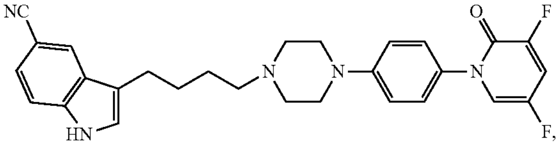
,
(28)
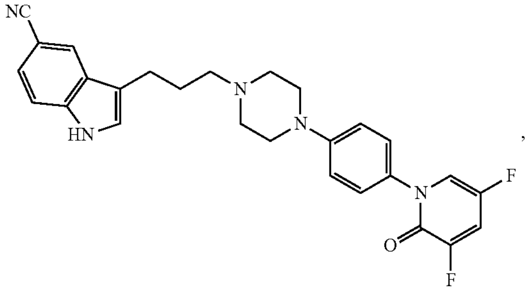
,
(29)
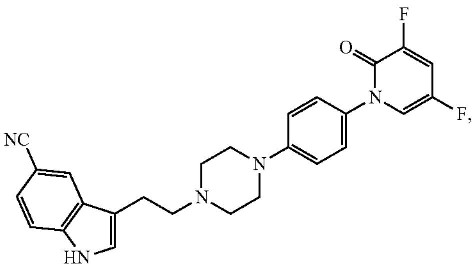
,
(30)
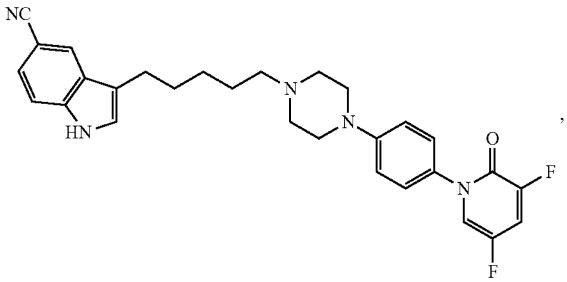
, -continued
(31)
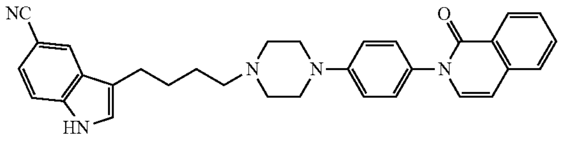,
(32)
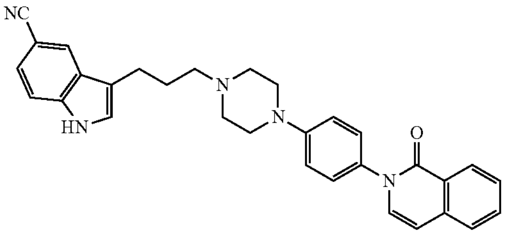,
(33)
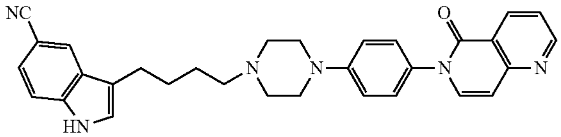,
(34)
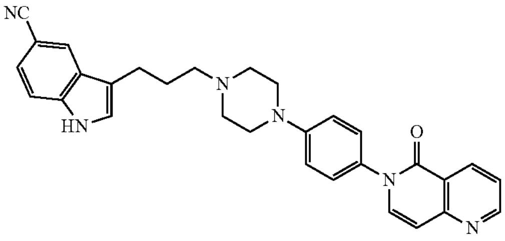,
(35)
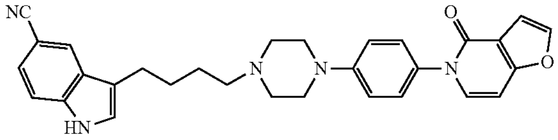,
(36)
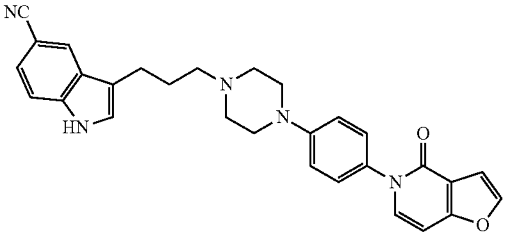,
(37)
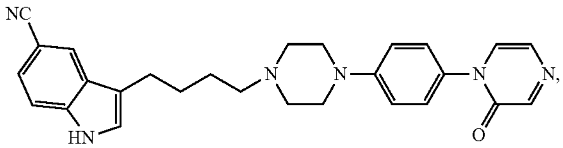,
(38)
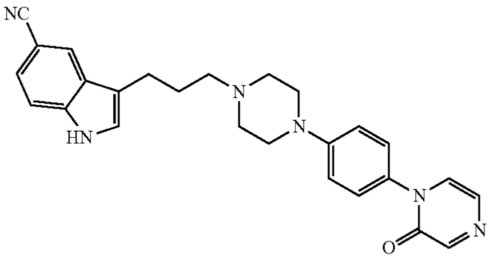,
(39)
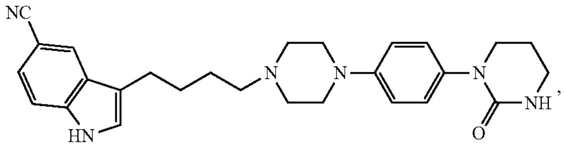,
(40)
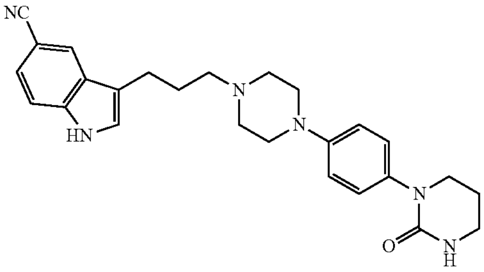,
(41)
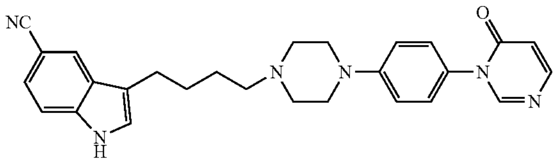,
(42)
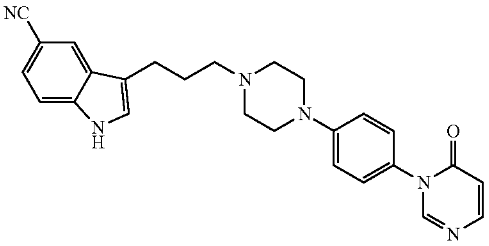, -continued
(43)
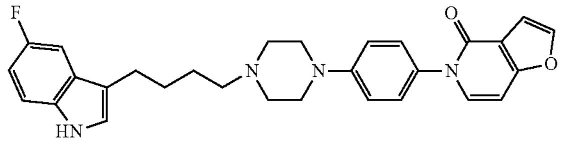
,
(44)
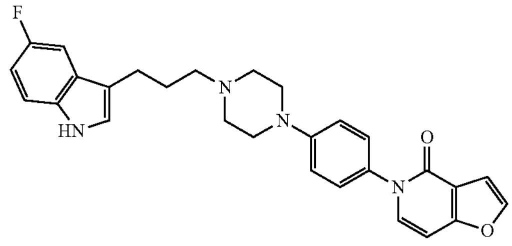
,
(45)
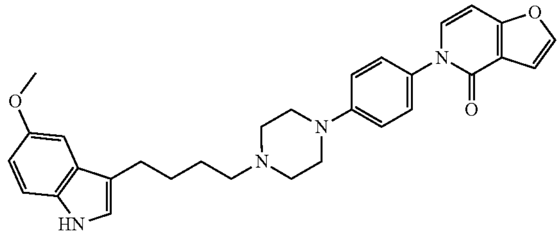
,
(46)
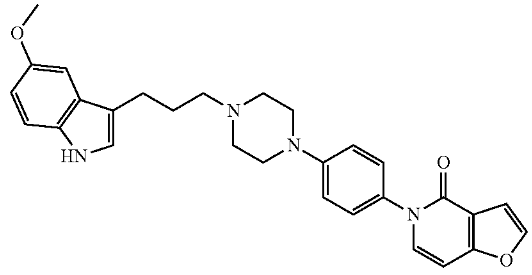
,
(47)
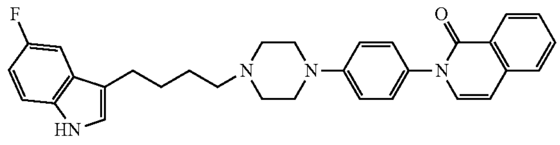
,
(48)
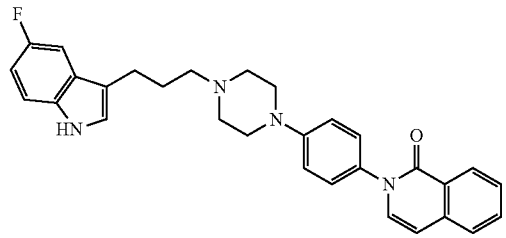
,
(49)
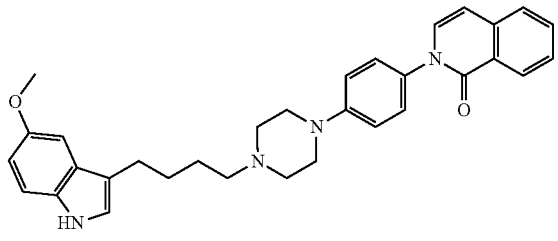
,
(50)
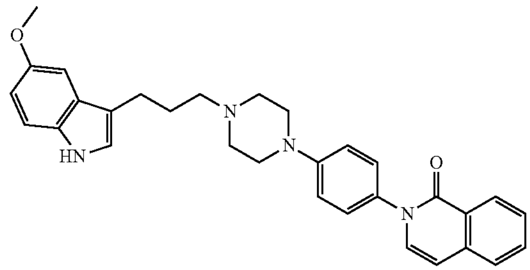
,
(51)
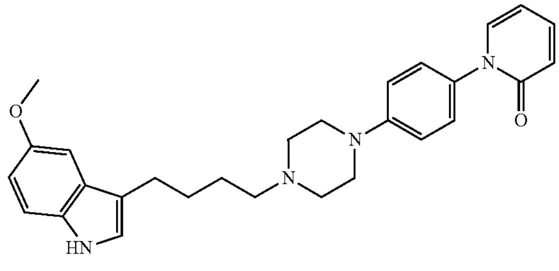
,
(52)
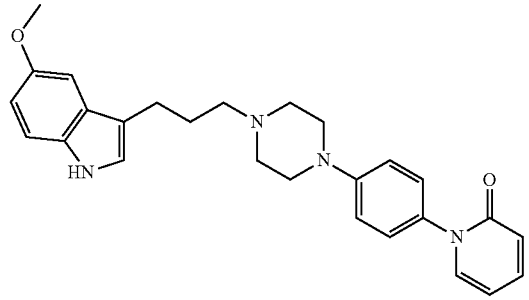
, -continued
(53)
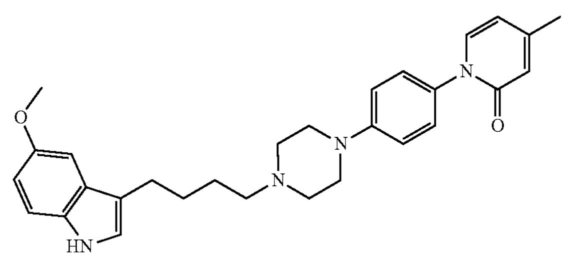
,
(54)
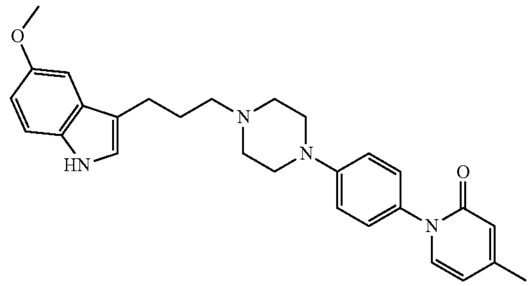
,
(55)
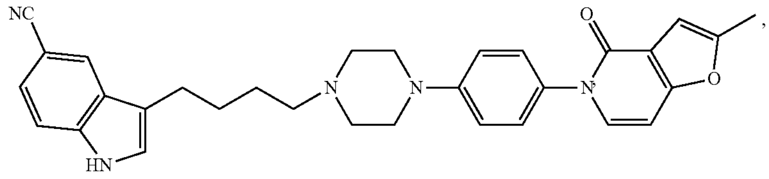
,
(56)
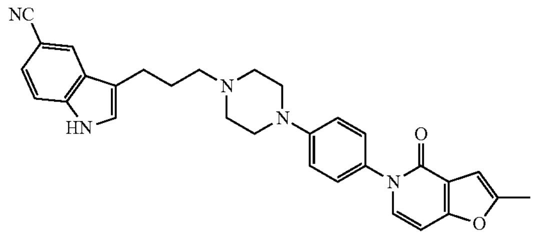
,
(57)
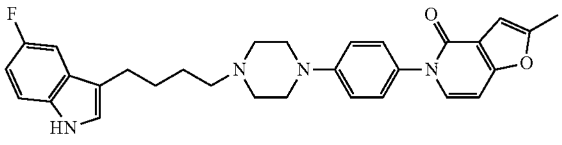
,
(58)
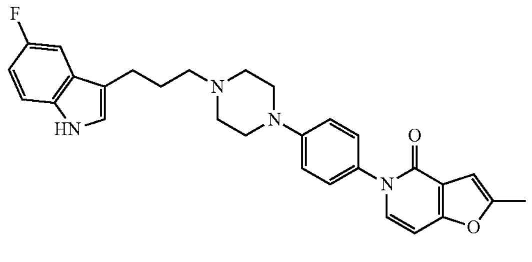
,
(59)
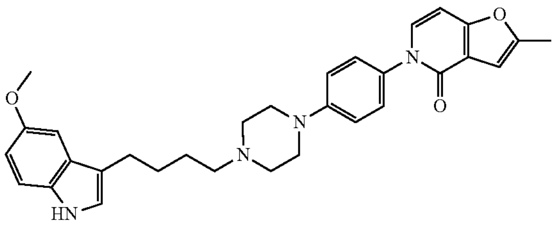
,
(60)
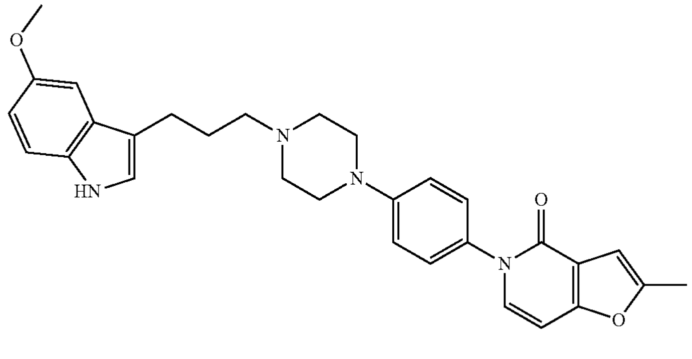
, -continued
(61)
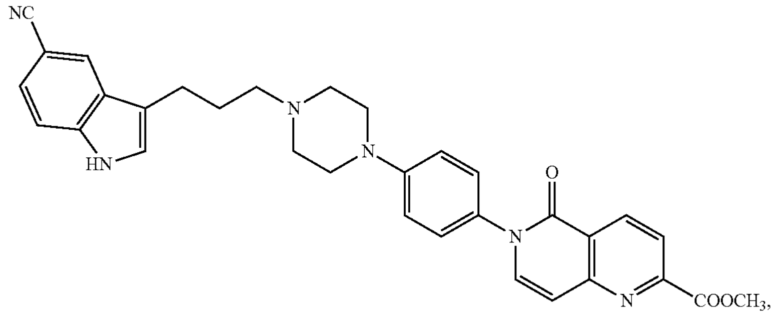
(62)
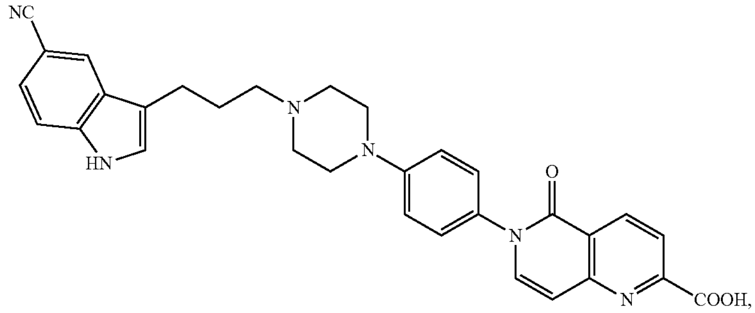
(63)
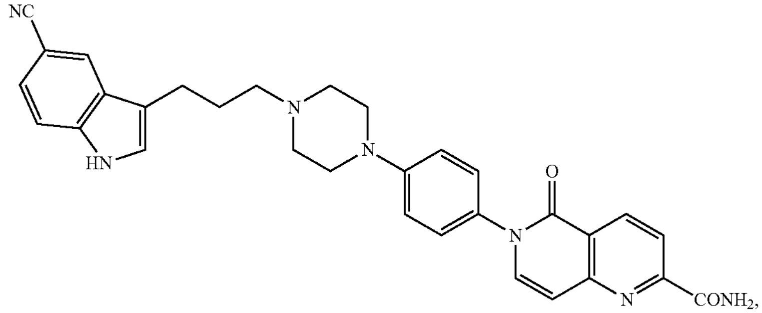
(64)
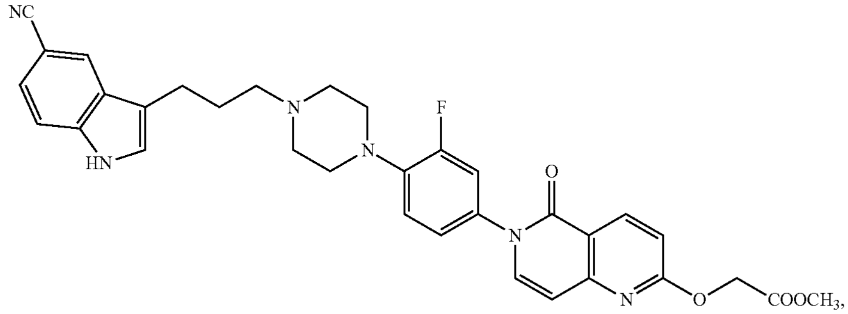
(65)
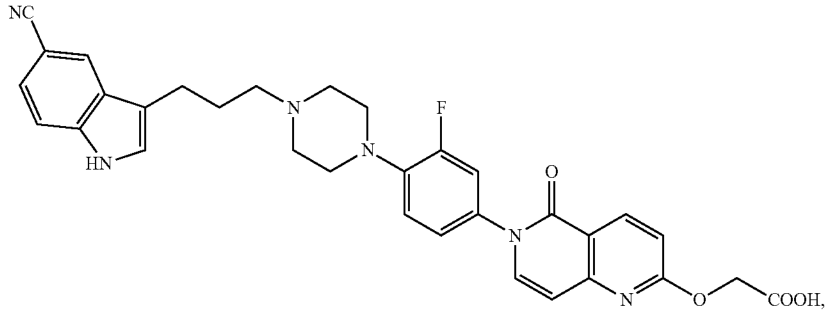

-continued (66)

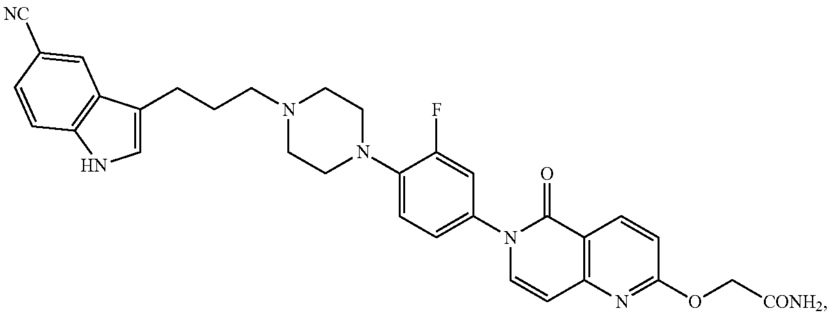

(67)

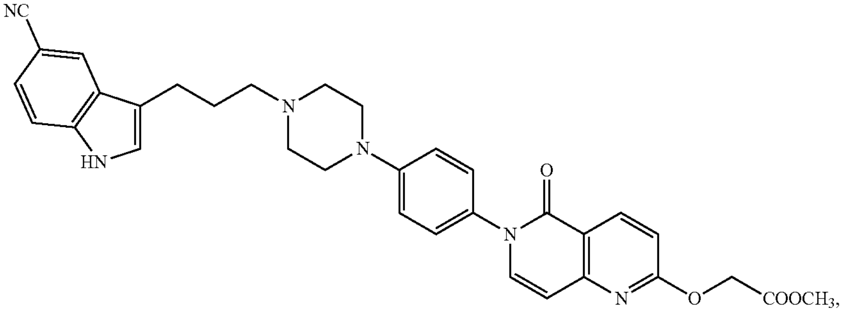

(68)

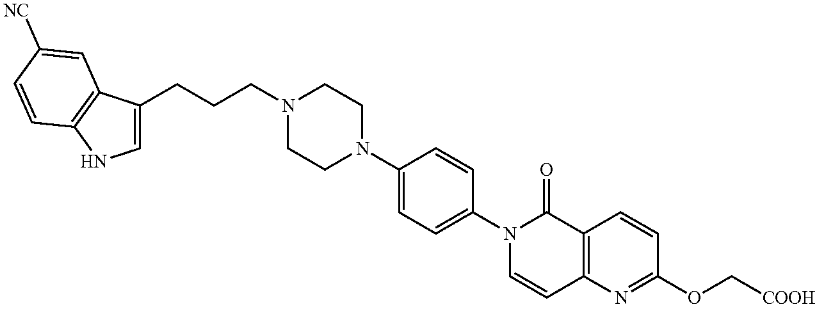

and (69)

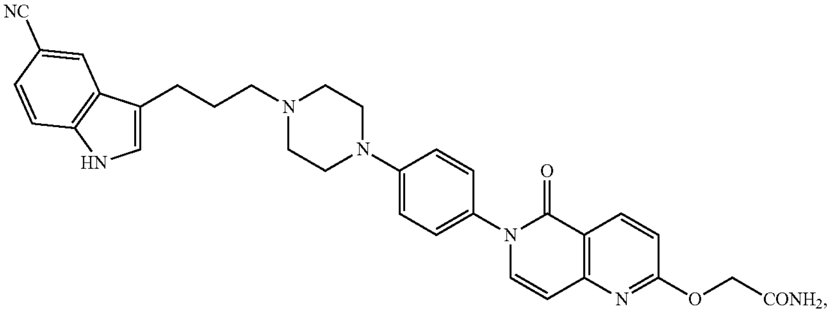

or a stereoisomer, a tautomer, an N-oxide, a solvate, a metabolite, a pharmaceutically acceptable salt or a prodrug thereof.

14. A pharmaceutical composition comprising the compound according to claim 1, and optionally further comprising a pharmaceutically acceptable excipient, carrier, adjuvant or a combination thereof.

15. The pharmaceutical composition according to claim 14 further comprising an additional therapeutic agent for central nervous system dysfunction, wherein the additional therapeutic agent is an antidepressant, an antianxiety agent, a lithium agent of a mood stabilizer, an atypical antipsychotic agent, an antiepileptic agent, an anti-Parkinson agent, a selective serotonin reuptake inhibitor, a 5-$HT_{1A}$ receptor agonist, a central nervous system stimulant, a nicotine antagonist or a combination thereof; or wherein the additional therapeutic agent is amitriptyline, desipramine, mirtazapine, bupropion, reboxetine, fluoxetine, trazodone, sertraline, duloxetine, fluvoxamine, milnacipran, levomilnacipran, desvenlafaxine, vilazodone, venlafaxine, dapoxetine, nefazodone, femoxetine, clomipramine, citalopram, escitalopram, paroxetine, lithium carbonate, buspirone, olanzapine, quetiapine, risperidone, ziprasidone, aripiprazole, perospirone, clozapine, modafinil, mecamylamine, cabergoline, adamantane, imipramine, pramipexole, thyroxine, dextromethorphan, quinidine, naltrexone, samidorphan, buprenorphine, melatonin, alprazolam, pipamperone, vestipitant, chlordiazepoxide, perphenazine or a combination thereof.

16. A method of lessening the severity of a central nervous system dysfunction through selectively inhibiting serotonin reuptake in a subject comprising administrating a therapeutically effective amount of the compound according to claim 1 to the subject.

17. A method of inhibiting serotonin reuptake with the compound according to claim 1.

18. A method of partially activating 5-$HT_{1A}$ receptor with the compound according to claim 1.

19. A method of lessening the severity of a central nervous system dysfunction through selectively inhibiting serotonin reuptake activity in a subject comprising administrating a therapeutically effective amount of the pharmaceutical composition according to claim 14 to the subject.

20. A method of inhibiting serotonin reuptake with the pharmaceutical composition according to claim 14.

21. A method of partially activating 5-$HT_{1A}$ receptor with the pharmaceutical composition according to claim 14.

* * * * *